(12) United States Patent
Alonso-Alija et al.

(10) Patent No.: US 7,781,470 B2
(45) Date of Patent: Aug. 24, 2010

(54) AMINODICARBOXYLIC ACID DERIVATIVES HAVING PHARMACEUTICAL PROPERTIES

(75) Inventors: Cristina Alonso-Alija, Haan (DE); Markus Heil, Leichlingen (DE); Dietmar Flubacher, Freiburg (DE); Paul Naab, Wuppertal (DE); Josef Pernerstorfer, Wuppertal (DE); Johannes-Peter Stasch, Solingen (DE); Frank Wunder, Wuppertal (DE); Klaus Dembowsky, Boston, MA (US); Elizabeth Perzborn, Wuppertal (DE); Elke Stahl, Bergisch Gladbach (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 12/422,763

(22) Filed: Apr. 13, 2009

(65) Prior Publication Data

US 2009/0203906 A1    Aug. 13, 2009

Related U.S. Application Data

(62) Division of application No. 11/200,455, filed on Aug. 8, 2005, now Pat. No. 7,517,896, which is a division of application No. 10/088,060, filed as application No. PCT/EP00/08469 on Aug. 31, 2000, now Pat. No. 7,087,644.

(30) Foreign Application Priority Data

Sep. 13, 1999    (DE) .................................. 199 43 635

(51) Int. Cl.
*A61K 31/41* (2006.01)
*A61K 31/277* (2006.01)
*C07D 257/00* (2006.01)

(52) U.S. Cl. ........................ 514/381; 514/521; 514/567; 514/620; 548/253; 558/410; 562/450

(58) Field of Classification Search ........................ None
See application file for complete search history.

(56) References Cited

U.S. PATENT DOCUMENTS

| 3,646,145 A | 2/1972 | Thiele |
| 4,154,837 A | 5/1979 | Heider et al. |
| 4,483,867 A | 11/1984 | Svahn et al. |
| 4,629,737 A | 12/1986 | Cantello |

FOREIGN PATENT DOCUMENTS

| DE | 19642255 | 4/2008 |
| EP | 0053434 | 9/1982 |
| EP | 0345068 | 6/1989 |
| EP | 0341551 | 11/1989 |
| WO | WO 9300359 | 1/1993 |
| WO | WO 9816223 | 4/1998 |
| WO | WO 9816507 | 4/1998 |
| WO | WO 9823619 | 6/1998 |

OTHER PUBLICATIONS

Stasch, J.-P. et al., "NO- and Haem-independent Activation of Soluble Guanylyl Cyclase: Molecular Basis and Cardiovascular Implications of a New Pharmacological Principle" Brit. J. of Pharmacol., 136: 773-783 (2002).
Weber, M. et al., "The Effect of Peroxynitrate on the Catalytic Activity of Soluble Guanylyl Cyclase.," Free Rad. Bio & Med. 31: 1360-1367 (2001).
Pryor, W. A. et al., "The Ehemistry of Peroxynitrate: A product from the Reaction of Nitric Oxide with Superoxide," Am. J. Physiol. 26: L699-L722 (1995).
Harrison, D. G., "Endothelial Function and Oxidant Stress," Clin. Cardiol. 20(II): 11-17 (1997).
Stasch, J.-P. et al., "Pharmacaolgical Actions of a Novel NO-Independent Guanylyl Cyclase Stimulator, Bay 41-8543: in vitro studies," Brit. J. of Pharmacol., 135: 333-343 (2002).
Schrammel, A. et al., "Characterization of 1H-[1,2,4]Oxadiazolo[4,3-a]quinoxalin-1-one as a Heme-Site Inhibitor of Nitric Oxide-Sensitive Guanylyl Cyclase," Mol. Pharmacology, 50: 1-5 (1996).

(Continued)

*Primary Examiner*—Kamal A Saeed
(74) *Attorney, Agent, or Firm*—Thomas C. Blankinship; Barbara A. Shimei

(57) ABSTRACT

The invention relates to compounds of formulae (II), (IV), and (VI) as shown below,

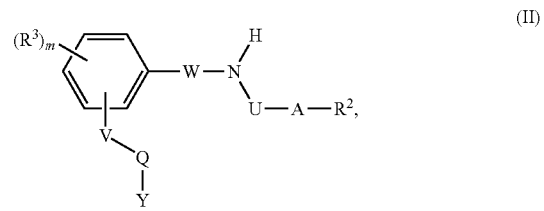

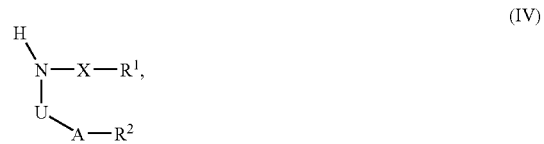

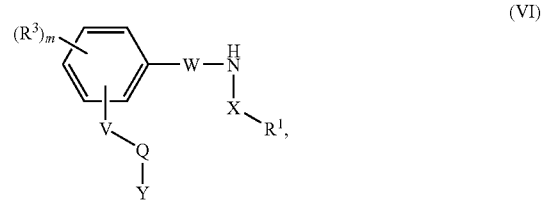

wherein the several variable groups are as defined in the specification and claims. Processes for making these materials, and methods for using them in the synthesis of compounds for treatment of cardiovascular disorders and fibrotic disorders are also disclosed.

1 Claim, No Drawings

OTHER PUBLICATIONS

Schmidt, P. et al., "Mechanisms of Nitric Oxide Independent Activiation of Soluble Guanylyl Cyclase," Eur. J. Pharmacol., 468: 167-174 (2003).

Garwaite et al., "Potent and Selective Inhibition of Nitric Oxide-Sensitive Guanylyl Cyclase by 1H-[1,2,4]Oxadiazolo[4,3-a]quinoxalin-1-one," Mol. Pharmacol., 48: 184-188 (1995).

Schmidt, P.M. et al, "Identification of Residues Crucially Involved in the Binding of the Heme Moiety of Soluble Guanylate Cyclase," J. Biol Chem. (Papers in Press in Oct. 21, 2003).

Muelsch, A. et al., "Impairement of Soluble Guanylyl Cyclase by Peroxynitrite," Abs. Scientific Sessions 2000, Basic Science, Publishing ID: 1724, AHA, Circulation, vol. 102, Supp. I, pp. 351, (2000).

Ko. F.-N. et al., "YC-1, a Novel Activator of the Platelet Guanylate Cyclase," Blood, 84(12): 4226-4233 (1994).

Mulsch, A. et al., "Effect of YC-1, and NO-independent, Superoxide-Sensitive Stimulator of Soluble GuanylylCyclase, On Smooth Muscle Responsiveness to Nitro Vasodilators," Brit. J. of Pharmacol., 120: 681-689 (1997).

Glass, D. B. et al. "Stimulation of Human Platelet Guanylate Cyclase by Fatty Acids," J. of Biol. Chem., 252(4): 1279-1285 (1977).

Pettitbone, D. J. et al., "A Structurally Novel Stimulator of Gyanylate Cyclase with Long-lasting Hypotensive Activity in the Dog," Eur. J. Pharmacol., 116:307-312 (1985).

Yu, S.-M. et al., "Vasorelaxant Effect of Isoliquiritigenin, a Novel Soluble Guanylate Cyclase Activator in Rat Aorta," Brit J. Pharmacol., 114: 1587-1594 (1995).

Gerzer, R. et al., "Soluble Gyanylate Cyclase Purified From Bovine Lung Contains Heme and Copper," BEGS Lett. 132(1): 71-74 (1981).

Hoenicka, M. et al., "Purified Soluble Guanylyl Cyclase Expressed in a Baculovirus/Sf9 System: Stimulation by YC-1, Nitric Oxide, and Carbon Monoxide," J. Mol. Med. 77: 14-23 (1999).

Ignarro, L., "Regulation of Cytosolic Guanylyl Cyclase by Porphiyrins and Metalloporphyrins," Adv. Pharmacol., 26: 35-65 (1994).

AMINODICARBOXYLIC ACID DERIVATIVES HAVING PHARMACEUTICAL PROPERTIES

This Application is a divisional of U.S. application Ser. No. 11/200,455, filed Aug. 8, 2005 now U.S. Pat. No. 7,517,896 which is a divisional of U.S. application Ser. No. 10/088,060, filed Jun. 27, 2002, now U.S. Pat. No. 7,087,644 which is a national stage filing under 35 U.S.C. §371 of PCT International Application PCT/EP00/08469, filed Aug. 31, 2000, which claims priority of German Patent Application No. 199 43 635.5 filed Sep. 13, 1999. The disclosures of the aforementioned patent applications are expressly incorporated by reference in their entireties.

The present invention relates to novel chemical compounds which stimulate soluble guanylate cyclase also via a novel mechanism of action which proceeds without participation of the haem group of the enzyme, to their preparation and to their use as medicaments, in particular as medicaments for treating cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The known representatives of this family can be classified both according to structural features and according to the type of ligands into two groups: the particular guanylate cyclases, which can be stimulated by natriuretic peptides, and the soluble guanylate cyclases, which can be stimulated by NO. The soluble guanylate cyclases consist of two subunits and, most likely, contain one haem per heterodimer, which is part of the regulatory centre. It is of central importance for the activation mechanism. NO can bind to the iron atom of the haem and thus increase the activity of the enzyme considerably. In contrast, haem-free preparations cannot be stimulated by NO. CO, too, is capable of attacking the central iron atom of haem, but the stimulation by CO is considerably lower than that by NO.

By binding cGMP, and owing to the resulting regulation of phosphodiesterases, ion channels and protein kinases, guanylate cyclase plays an important rôle in various physiological processes, in particular in the relaxation and proliferation of smooth muscle cells, in platelet aggregation and platelet adhesion and in neuronal signal transmission, and also in disorders which are based on a disturbance of the abovementioned processes. Under pathophysiological conditions, the NO/cGMP system can be suppressed, which may lead, for example, to hypertension, platelet activation, increased cell proliferation, endothelial dysfunction, atherosclerosis, angina pectoris, cardiac insufficiency, thromboses, stroke and myocardial infarct.

Owing to the expected high efficiency and few side effects, a treatment of such disorders which targets the influence of the cGMP signal path in organisms and is NO-independent is a promising approach.

Hitherto, for the therapeutic stimulation of soluble guanylate cyclase use has exclusively been made of compounds such as organic nitrates whose effect is based on NO. This is formed by bioconversion and activates soluble guanylate cyclase by attack at the central iron atom of haem. In addition to the side effects, the development of tolerance is one of the decisive disadvantages of this treatment.

Within the last few years, some substances have been described which stimulate soluble guanylate cyclase directly, i.e. without prior release of NO, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmacol. 116 (1985), 307), isoliquiritigenin (Yu et al., Brit. J. Pharmacol. 114 (1995), 1587), and various substituted pyrazole derivatives (WO 98/16223, WO 98/16507 and WO 98/23619).

The known stimulators of soluble guanylate cyclases stimulate the enzyme either directly via the haem group (carbon monoxide, nitrogen monoxide or diphenyliodoniumhexafluorophosphate) by interaction with the iron centre of the haem group and a resulting change in conformation which leads to an increase in enzyme activity (Gerzer et al., FEBS Lett. 132 (1981), 71), or via a haem-dependent mechanism which is independent of NO but leads to a potentiation of the stimulating effect of NO or CO (for example YC-1, Hoenicka et al., J. Mol. Med. (1999) 14; or the pyrazole derivatives described in WO 98/16223, WO 98/16507 and WO 98/23619).

The stimulating effect, asserted in the literature, of isoliquiritigenin and of fatty acids, such as, for example, arachidonic acid, prostaglandin endoperoxides and fatty acid hydroperoxides, on soluble guanylate cyclase could not be confirmed (cf., for example, Hoenicka et al., J. Mol. Med. 77 (1999), 14).

If the haem group of soluble guanylate cyclase is removed, the enzyme still shows a detectable catalytic basal activity, i.e. as before, cGMP is formed. The remaining catalytic basal activity of the haem-free enzyme cannot be stimulated by any of the abovementioned known stimulators.

Stimulation of haem-free soluble guanylate cyclase by protoporphyrin IX has been described (Ignarro et al., Adv. Pharmacol. 26 (1994), 35). However, protoporphyrin IX can be considered to be a mimic of the NO-haem adduct, owing to which the addition of protoporphyrin IX to soluble guanylate cyclase should result in the formation of an enzyme structure which corresponds to the haem-containing soluble guanylate cyclase which is stimulated by NO. This is also confirmed by the fact that the stimulating effect of protoporphyrin IX is increased by the NO-independent, but haem-dependent, stimulator YC-1 described above (Mülsch et al., Naunyn Schmiedebergs Arch. Pharmacol. 355, R47).

Thus, hitherto no compounds have been described which are capable of stimulating soluble guanylate cyclase independently of the haem group present in the enzyme.

It was an object of the present invention to develop medicaments for the treatment of cardiovascular disorders or other disorders which can be treated by influencing the cGMP signal path in organisms.

The abovementioned object is achieved by using, for the preparation of medicaments, compounds which are capable of stimulating soluble guanylate cyclase also independently of NO and the haem group present in the enzyme.

Surprisingly, it has been found that there are compounds which are capable of stimulating soluble guanylate cyclase also independently of the haem group present in the enzyme. The biological activity of these stimulators is based on an entirely novel mechanism for stimulating soluble guanylate cyclase. In contrast to the above-described compounds which are known from the prior art as stimulators of soluble guanylate cyclase, the compounds according to the invention are capable of stimulating both the haem-containing and the haem-free form of soluble guanylate cyclase. In the case of these novel stimulators, the stimulation of the enzyme is therefore effected via a haem-independent route, which is also confirmed by the fact that, on the one hand, the novel stimulators do not show any synergistic action with NO at the haem-containing enzyme and, on the other hand, the action of these novel stimulators cannot be blocked by the haem-dependent inhibitor of soluble guanylate cyclase, 1H-1,2,4-oxadiazol-(4,3a)-quinoxalin-1-one (ODQ).

This is a novel therapeutic approach for the treatment of cardiovascular disorders and other disorders which can be treated by influencing the cGMP signal path in organisms.

EP-A-0 345 068 describes, inter alia, the aminoalkanecarboxylic acid (1) as an intermediate in the synthesis of GABA antagonists:

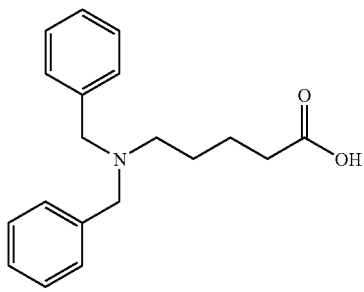

(1)

WO 93/00359 describes the aminoalkanecarboxylic acid (2) as an intermediate in peptide synthesis and its use as an active compound for treating disorders of the central nervous system:

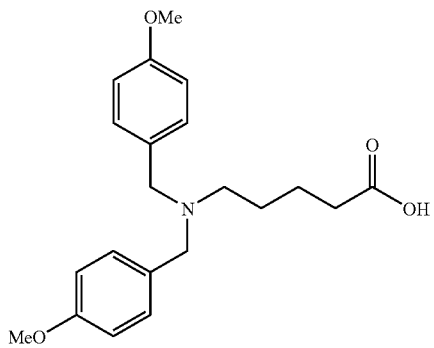

(2)

However, neither of these two publications mentions that such aminoalkanecarboxylic acids can have a stimulating effect on soluble guanylate cyclase which is independent of the haem group present in the enzyme.

According to a preferred embodiment of the present invention, for stimulating soluble guanylate cyclase independently of the haem group present in the enzyme, aminoalkanecarboxylic acids of the formula (I) are used:

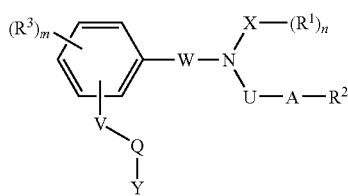

(I)

in which
V is absent, O, $NR^4$, $NR^4CONR^4$, $NR^4CO$, $NR^4SO_2$, COO, $CONR^4$ or $S(O)_o$,
in which
$R^4$, independently of any other radical $R^4$ which may be present, is hydrogen, straight-chain or branched alkyl having up to 8 carbon atoms, cycloalkyl having 3 to 8 carbon atoms, aryl having 6 to 10 carbon atoms or arylalkyl having 7 to 18 carbon atoms, where the aryl radical for its part may be mono- or polysubstituted by halogen, alkyl, alkoxy having up to 6 carbon atoms,
o is 0, 1 or 2,
Q is absent, straight-chain or branched alkylene, straight-chain or branched alkenediyl or straight-chain or branched alkinediyl having in each case up to 12 carbon atoms, which may in each case contain one or more groups from the group consisting of O, $S(O)_p$, $NR^5$, CO, $NR^5SO_2$ or $CONR^5$ and which may be mono- or polysubstituted by halogen, hydroxyl or alkoxy having up to 4 carbon atoms, where optionally any two atoms of the abovementioned chain may be attached to one another forming a three- to eight-membered ring,
in which
$R^5$ is hydrogen, straight-chain or branched alkyl having up to 8 carbon atoms or cycloalkyl having 3 to 8 carbon atoms which may be substituted by halogen or alkoxy having up to 4 carbon atoms,
p is 0, 1 or 2,
Y is hydrogen, $NR^8R^9$, aryl having 6 to 10 carbon atoms, an aromatic or saturated heterocycle having 1 to 9 carbon atoms and up to 3 heteroatoms from the group consisting of S, N and O or straight-chain or branched cycloalkyl having 3 to 8 carbon atoms, which may also be attached via N,
where the cyclic radicals may in each case be mono- to trisubstituted by straight-chain or branched alkyl, straight-chain or branched alkenyl, straight-chain or branched alkinyl, straight-chain or branched alkoxy, straight-chain or branched alkoxyalkoxy, straight-chain or branched halogenoalkyl, straight-chain or branched halogenoalkoxy having in each case up to 8 carbon atoms, straight-chain or branched cycloalkyl having 3 to 8 carbon atoms, halogen, hydroxyl, CN, $SR^6$, $NO_2$, $NR^8R^9$, $NR^7COR^{10}$, $NR^7CONR^7R^{10}$ or $CONR^{11}R^{12}$,
in which
$R^6$ is hydrogen, straight-chain or branched alkyl having up to 8 carbon atoms, straight-chain or branched halogenoalkyl having up to 8 carbon atoms or cycloalkyl having 3 to 8 carbon atoms,
$R^7$ independently of any other radical $R^7$ which may be present is hydrogen, straight-chain or branched alkyl having up to 8 carbon atoms or cycloalkyl having 3 to 8 carbon atoms,
$R^8$, $R^9$, $R^{11}$ and $R^{12}$ independently of one another are hydrogen, straight-chain or branched alkyl, straight-chain or branched alkenyl having up to 8 carbon atoms, aryl having 6 to 10 carbon atoms, an aromatic heterocycle having 1 to 9 carbon atoms and up to 3 heteroatoms from the group consisting of S, N and O, arylalkyl having 8 to 18 carbon atoms, cycloalkyl having 3 to 8 carbon atoms or a radical of the formula $SO_2R^{13}$,
where the aryl radical for its part may be mono- or polysubstituted by halogen, hydroxyl, CN, $NO_2$, $NH_2$, $NHCOR^7$, alkyl, alkoxy, halogenoalkyl or halogenoalkoxy having up to 6 carbon atoms, or two substituents $R^8$ and $R^9$ or $R^{11}$ and $R^{12}$ may be attached to one another forming a five- or six-membered ring which may contain O or N, in which, $R^{13}$ is straight-chain or branched alkyl having up to 4 carbon atoms or aryl having 6 to 10 carbon atoms, where the aryl radical for its part may be mono- or polysubstituted by halogen, CN, $NO_2$, alkyl, alkoxy, halogenoalkyl or halogenoalkoxy having up to 6 carbon atoms, $R^{10}$ is hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may furthermore optionally be substituted by halogen, hydroxyl, CN, $NO_2$, $NH_2$, $NHCOR^7$, alkyl, alkoxy, halogenoalkyl or halogenoalkoxy having up to 6 carbon atoms;

and/or the cyclic radicals may in each case be mono- to trisubstituted by aryl having 6 to 10 carbon atoms, an aromatic or saturated heterocycle having 1 to 9 carbon atoms and up to 3 heteroatoms from the group consisting of S, N and O, which may also be attached via N, which may be attached directly or via a group O, S, SO, $SO_2$, $NR^7$, $SO_2NR^7$, $CONR^7$, straight-chain or branched alkylene, straight-chain or branched alkenediyl, straight-chain or branched alkyloxy, straight-chain or branched oxyalkyloxy, straight-chain or branched sulphonylalkyl, straight-chain or branched thioalkyl having in each case up to 8 carbon atoms and which may be mono- to trisubstituted by straight-chain or branched alkyl, straight-chain or branched alkoxy, straight-chain or branched alkoxyalkoxy, straight-chain or branched halogenoalkyl, straight-chain or branched halogenoalkoxy, carbonylalkyl or straight-chain or branched alkenyl having in each case up to 6 carbon atoms, halogen, $SR^6$, CN, $NO_2$, $NR^8R^9$, $CONR^{15}R^{16}$ or $NR^{14}COR^{17}$, in which $R^{14}$ is hydrogen, straight-chain or branched alkyl having up to 8 carbon atoms or cycloalkyl having 3 to 8 carbon atoms, $R^{15}R^{16}$ independently of one another are hydrogen, straight-chain or branched alkyl having up to 8 carbon atoms, cycloalkyl having 3 to 8 carbon atoms, aryl having 6 to 10 carbon atoms or a radical of the formula $SO_2R^{18}$, where the aryl radical for its part may be mono- or polysubstituted by halogen, hydroxyl, CN, $NO_2$, $NH_2$, $NHCOR^7$, alkyl, alkoxy, halogenoalkyl or halogenoalkoxy having up to 6 carbon atoms, in which $R^{18}$ is straight-chain or branched alkyl having up to 4 carbon atoms or aryl having 6 to 10 carbon atoms, where the aryl radical for its part may be mono- or polysubstituted by halogen, hydroxyl, CN, $NO_2$, $NH_2$, $NHCOR^7$, alkyl, alkoxy, halogenoalkyl or halogenoalkoxy having up to 6 carbon atoms, and $R^{17}$ is hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may furthermore optionally be substituted by halogen, hydroxyl, CN, $NO_2$, $NH_2$, $NHCOR^7$, alkyl, alkoxy, halogenoalkyl or halogenoalkoxy having up to 6 carbon atoms;

and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O, $R^3$ is hydrogen, halogen, straight-chain or branched alkyl, straight-chain or branched halogenoalkyl, straight-chain or branched alkoxy, or alkoxycarbonyl having in each case up to 4 carbon atoms, CN, $NO_2$ or $NR^{19}R^{20}$, in which $R^{19}$ and $R^{20}$ independently of one another are hydrogen, straight-chain or branched alkyl having up to 4 carbon atoms or cycloalkyl having 3 to 8 carbon atoms, m is an integer from 1 to 4, W is straight-chain or branched alkylene having up to 6 carbon atoms or straight-chain or branched alkenediyl having up to 6 carbon atoms which may in each case contain a group from the group consisting of O, $S(O)_q$, $NR^{21}$, CO and $CONR^{21}$, or is CO, NHCO or OCO, in which q is 0, 1 or 2, $R^{21}$ is hydrogen, straight-chain or branched alkyl having up to 8 carbon atoms or cycloalkyl having 3 to 8 carbon atoms, U is straight-chain or branched alkyl having up to 4 carbon atoms, A is aryl having 6 to 10 carbon atoms or an aromatic heterocycle having 1 to 9 carbon atoms and up to 3 heteroatoms from the group consisting of S, N and O, which may optionally be mono- to trisubstituted by halogen, straight-chain or branched alkyl, straight-chain or branched halogenoalkyl, straight-chain or branched alkoxy, halogenoalkoxy or alkoxycarbonyl having up to 4 carbon atoms, CN, $NO_2$ or $NR^{22}R^{23}$, in which $R^{22}$ and $R^{23}$ independently of one another are each hydrogen, straight-chain or branched alkyl having up to 8 carbon atoms or cycloalkyl having 3 to 8 carbon atoms, carbonylalkyl or sulphonylalkyl, $R^2$ is tetrazolyl, $COOR^{24}$ or $CONR^{25}R^{26}$, in which $R^{24}$ is hydrogen, alkyl having 1 to 8 carbon atoms or cycloalkyl having 3 to 8 carbon atoms, $R^{25}$ and $R^{26}$ independently of one another are each hydrogen, straight-chain or branched alkyl having up to 8 carbon atoms, cycloalkyl having 3 to 8 carbon atoms or a radical of the formula $SO_2R^{27}$, or $R^{25}$ and $R^{26}$ together form a five- or six-membered ring which may contain N or O, in which $R^{27}$ is straight-chain or branched alkyl having up to 4 carbon atoms or aryl having 6 to 10 carbon atoms, where the aryl radical for its part may be mono- or polysubstituted by halogen, CN, $NO_2$, alkyl, alkoxy, halogenoalkyl or halogenoalkoxy having up to 6 carbon atoms, X is straight-chain or branched alkylene having up to 12 carbon atoms or straight-chain or branched alkenediyl having up to 12 carbon atoms which may in each case contain one to three groups from the group consisting of O, $S(O)_r$, $NR^{28}$, CO or $CONR^{29}$, aryl or aryloxy having 6 to 10 carbon atoms, where the aryl radical for its part may be mono- or polysubstituted by halogen, CN, $NO_2$, alkyl, alkoxy, halogenoalkyl or halogenoalkoxy having up to 6 carbon atoms, where optionally any two atoms of the abovementioned chains are attached to one another via an alkyl chain, forming a three- to eight-membered ring,
in which
r is 0, 1 or 2,
$R^{28}$ is hydrogen, alkyl having 1 to 8 carbon atoms or cycloalkyl having 3 to 8 carbon atoms,
$R^{29}$ is hydrogen, straight-chain or branched alkyl having up to 8 carbon atoms or cycloalkyl having 3 to 8 carbon atoms,
n is 1 or 2,
$R^1$ is tetrazolyl, $COOR^{30}$ or $CONR^{31}R^{32}$,
in which
$R^{30}$ is hydrogen, alkyl having 1 to 8 carbon atoms or cycloalkyl having 3 to 8 carbon atoms,
$R^{31}$ and $R^{32}$ independently of one another are each hydrogen, straight-chain or branched alkyl having up to 8 carbon atoms, cycloalkyl having 3 to 8 carbon atoms or a radical of the formula $SO_2R^{33}$,
in which
$R^{33}$ is straight-chain or branched alkyl having up to 4 carbon atoms or aryl having 6 to 10 carbon atoms, where the aryl radical for its part may be mono- or polysubstituted by halogen, CN, $NO_2$, alkyl, alkoxy, halogenoalkyl or halogenoalkoxy having up to 6 carbon atoms,
and its stereoisomers and salts.

Preference is given here to compounds of the formula (I)
in which
V is absent, O, $NR^4$, $NR^4CONR^4$, $NR^4CO$, $NR^4SO_2$, COO, $CONR^4$ or $S(O)_o$,
in which
$R^4$, independently of any other radical $R^4$ which may be present, is hydrogen, straight-chain or branched alkyl having up to 8 carbon atoms, cycloalkyl having 3 to 8 carbon atoms, aryl having 6 to 10 carbon atoms or arylalkyl having 7 to 18 carbon atoms, where the aryl radical for its part may be mono- or polysubstituted by halogen, alkyl, alkoxy having up to 6 carbon atoms,
o is 0, 1 or 2,
Q is absent, straight-chain or branched alkylene, straight-chain or branched alkenediyl or straight-chain or branched alkinediyl having in each case up to 12 carbon atoms, which may in each case contain one or more groups from the group consisting of O, $S(O)_p$, $NR^5$, CO, $NR^5SO_2$ or $CONR^5$ and which may be mono- or polysubstituted by halogen, hydroxyl or alkoxy having up to 4 carbon atoms, where optionally any two atoms of the abovementioned chain may be attached to one another forming a three- to eight-membered ring,
in which
$R^5$ is hydrogen, straight-chain or branched alkyl having up to 8 carbon atoms or cycloalkyl having 3 to 8 carbon atoms which may be substituted by halogen or alkoxy having up to 4 carbon atoms,
p is 0, 1 or 2,
Y is hydrogen, $NR^8R^9$, aryl having 6 to 10 carbon atoms, an aromatic or saturated heterocycle having 1 to 9 carbon atoms and up to 3 heteroatoms from the group consisting of S, N and O or straight-chain or branched cycloalkyl having 3 to 8 carbon atoms, which may also be attached via N,
where the cyclic radicals may in each case be mono- to trisubstituted by straight-chain or branched alkyl, straight-chain or branched alkenyl, straight-chain or branched alkinyl, straight-chain or branched alkoxy, straight-chain or branched alkoxyalkoxy, straight-chain or branched halogenoalkyl, straight-chain or branched halogenoalkoxy having in each case up to 8 carbon atoms, straight-chain or branched cycloalkyl having 3 to 8 carbon atoms, halogen, hydroxyl, CN, $SR^6$, NO, $NR^8R^9$, $NR^7COR^{10}$, $NR^7CONR^7R^{10}$ or $CONR^{11}R^{12}$,
in which
$R^6$ is hydrogen, straight-chain or branched alkyl having up to 8 carbon atoms, straight-chain or branched halogenoalkyl having up to 8 carbon atoms or cycloalkyl having 3 to 8 carbon atoms,
$R^7$ independently of any other radical $R^7$ which may be present is hydrogen, straight-chain or branched alkyl having up to 8 carbon atoms or cycloalkyl having 3 to 8 carbon atoms,
$R^8$, $R^9$, $R^{11}$ and $R^{12}$ independently of one another are hydrogen, straight-chain or branched alkyl, straight-chain or branched alkenyl having up to 8 carbon atoms, aryl having 6 to 10 carbon atoms, an aromatic heterocycle having 1 to 9 carbon atoms and up to 3 heteroatoms from the group consisting of S, N and O, arylalkyl having 8 to 18 carbon atoms, cycloalkyl having 3 to 8 carbon atoms or a radical of the formula $SO_2R^{13}$,
where the alkyl radical for its part may be mono- or polysubstituted by halogen, hydroxyl, CN, $NO_2$, $NH_2$, $NHCOR^7$, alkyl, alkoxy, halogenoalkyl or halogenoalkoxy having up to 6 carbon atoms,
or two substituents $R^8$ and $R^9$ or $R^{11}$ and $R^{12}$ may be attached to one another forming a five- or six-membered ring which may contain O or N,
in which,
$R^{13}$ is straight-chain or branched alkyl having up to 4 carbon atoms or aryl having 6 to 10 carbon atoms, where the aryl radical for its part may be mono- or polysubstituted by halogen, CN, $NO_2$, alkyl, alkoxy, halogenoalkyl or halogenoalkoxy having up to 6 carbon atoms,
$R^{10}$ is hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may furthermore optionally be substituted by halogen, hydroxyl, CN, $NO_2$, $NH_2$, $NHCOR^7$, alkyl, alkoxy, halogenoalkyl or halogenoalkoxy having up to 6 carbon atoms;
and/or the cyclic radicals may in each case be mono- to trisubstituted by aryl having 6 to 10 carbon atoms, an aromatic or saturated heterocycle having 1 to 9 carbon atoms and up to 3 heteroatoms from the group consisting of S, N and O, which may also be attached via N, which may be attached directly or via a group O, S, SO, $SO_2$, $NR^7$, $SO_2NR^7$, $CONR^7$, straight-chain or branched alkylene, straight-chain or branched alkenediyl, straight-chain or branched alkyloxy, straight-chain or branched oxyalkyloxy, straight-chain or branched sulphonylalkyl, straight-chain or branched thioalkyl having in each case up to 8 carbon atoms and which may be mono- to trisubstituted by straight-chain or branched alkyl, straight-chain or branched alkoxy, straight-chain or branched alkoxyalkoxy, straight-chain or branched halogenoalkyl, straight-chain or branched halogenoalkoxy, carbonylalkyl or straight-chain or branched alkenyl having in each case up to 6 carbon atoms, halogen, $SR^6$, CN, $NO_2$, $NR^8R^9$, $CONR^{15}R^{16}$ or $NR^{14}COR^{17}$,
in which
$R^{14}$ is hydrogen, straight-chain or branched alkyl having up to 8 carbon atoms or cycloalkyl having 3 to 8 carbon atoms,
$R^{15}$, $R^{16}$ independently of one another are hydrogen, straight-chain or branched alkyl having up to 8 carbon atoms, cycloalkyl having 3 to 8 carbon atoms or a radical of the formula $SO_2R^{18}$,
in which
$R^{18}$ is straight-chain or branched alkyl having up to 4 carbon atoms or aryl having 6 to 10 carbon atoms, where the aryl radical for its part may be mono- or polysubstituted by halogen, CN, $NO_2$, alkyl, alkoxy, halogenoalkyl or halogenoalkoxy having up to 6 carbon atoms,
and
$R^{17}$ is hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may furthermore optionally be substituted by halogen, CN, $NO_2$, alkyl, alkoxy, halogenoalkyl or halogenoalkoxy having up to 6 carbon atoms, %
and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O,
$R^3$ is hydrogen, halogen, straight-chain or branched alkyl, straight-chain or branched halogenoalkyl or straight-chain or branched alkoxy having in each case up to 4 carbon atoms,
m is an integer from 1 to 4,
W is straight-chain or branched alkylene or straight-chain or branched alkenediyl having in each case up to 4 carbon atoms,
U is —$CH_2$—,
A is phenyl or an aromatic heterocycle having 1 to 9 carbon atoms and up to 3 heteroatoms from the group consisting of S, N and O, which may optionally be mono- to trisubstituted by halogen, straight-chain or branched alkyl, straight-chain or branched halogenoalkyl or straight-chain or branched alkoxy having up to 4 carbon atoms,
$R^2$ is $COOR^{24}$,
in which
$R^{24}$ is hydrogen or straight-chain or branched alkyl having up to 6 carbon atoms,
X is straight-chain or branched alkylene having up to 8 carbon atoms or straight-chain or branched alkenediyl having up to 8 carbon atoms which may in each case contain one to three groups from the group consisting of phenyl, phenyloxy, O, CO and $CONR^{29}$,
in which
$R^{29}$ is hydrogen, straight-chain or branched alkyl having up to 6 carbon atoms or cycloalkyl having 3 to 6 carbon atoms,
n is 1 or 2,
$R^1$ is $COOR^{30}$,
in which
$R^{30}$ is hydrogen or straight-chain or branched alkyl having up to 6 carbon atoms.

Particular preference is given to compounds of the formula (I)
in which
V is absent, O, S or $NR^4$,
in which
$R^4$ is hydrogen or methyl,
Q is absent, straight-chain or branched alkylene having up to 9 carbon atoms or straight-chain or branched alkenediyl or straight-chain or branched alkinediyl having up to 4 carbon atoms which may be monosubstituted by halogen,
Y is H, $NR^8R^9$, cyclohexyl, phenyl, naphtyl or a heterocycle from the group consisting of

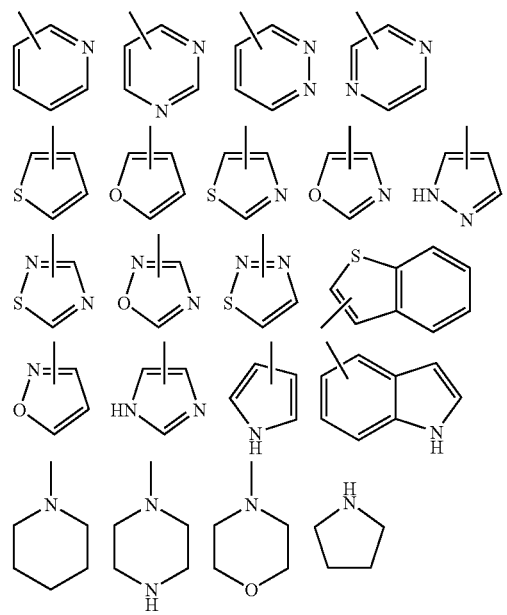

which may also be attached via N,
where the cyclic radicals may in each case be mono- to trisubstituted by straight-chain or branched alkyl, straight-chain or branched alkenyl, straight-chain or branched alkinyl, straight-chain or branched alkoxy, straight-chain or branched alkoxyalkoxy, straight-chain or branched halogenoalkyl, straight-chain or branched halogenoalkoxy having in each case up to 4 carbon atoms, straight-chain or branched cycloalkyl having 3 to 6 carbon atoms, F, Cl, Br, I, $NO_2$, $SR^6$, $NR^8R^9$, $NR^7COR^{10}$ or $CONR^{11}R^{12}$,
in which
$R^6$ is hydrogen, straight-chain or branched alkyl having up to 8 carbon atoms, or straight-chain or branched halogenoalkyl having up to 4 carbon atoms,
$R^7$ is hydrogen, or straight-chain or branched alkyl having up to 4 carbon atoms,
$R^8$, $R^9$, $R^{11}$ and $R^{12}$ independently of one another are hydrogen, straight-chain or branched alkyl having up to 4 carbon atoms or phenyl,
where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN, or two substituents R⁸ and R⁹ or R¹¹ and R¹² may be attached to one another forming a five- or six-membered ring which may be interrupted by O or N, R¹⁰ is hydrogen, straight-chain or branched alkyl having up to 4 carbon atoms or phenyl,
  where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, NO₂, CF₃, OCF₃ or CN;

and/or the cyclic radicals may in each case be mono- to trisubstituted by phenyl or a heterocycle from the group consisting of

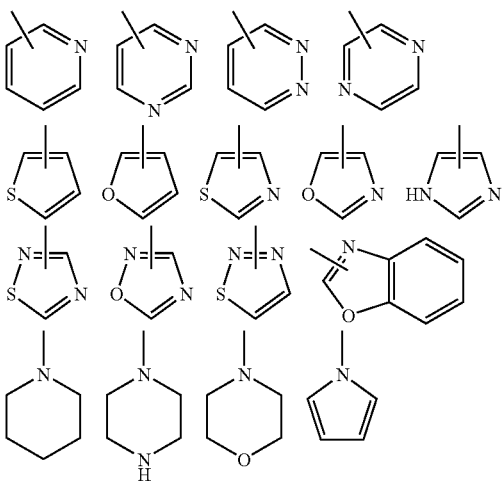

which may be attached directly or via a group O, S, SO, SO₂, NR⁴, SO₂NR⁷, CONR⁷, straight-chain or branched alkylene, straight-chain or branched alkenediyl, straight-chain or branched alkyloxy, straight-chain or branched oxyalkyloxy, straight-chain or branched sulphonylalkyl, straight-chain or branched thioalkyl having in each case 4 carbon atoms and which may be mono- to trisubstituted by straight-chain or branched alkyl, straight-chain or branched alkoxy, straight-chain or branched alkoxyalkoxy, straight-chain or branched halogenoalkyl or straight-chain or branched alkenyl having in each case up to 4 carbon atoms, F, Cl, Br, I, CN, SCH₃, OCF₃, NO₂, NR⁸R⁹ or NR¹⁴COR¹⁷,
in which
R¹⁴ is hydrogen, straight-chain or branched alkyl having up to 8 carbon atoms, or cycloalkyl having 3 to 8 carbon atoms,
and
R¹⁷ is hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may furthermore optionally be substituted by F, Cl Br, hydroxyl, methyl, ethyl, n-propyl, i-propyl, n-butyl, s-butyl, i-butyl, t-butyl, methoxy, ethoxy, amino, acetylamino, NO₂, CF₃, OCF₃ or CN;
and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O, R³ is hydrogen or fluorine,
m is an integer from 1 to 4,
W is CH₂, —CH₂CH₂—, CH₂CH₂CH₂, CH=CHCH₂,
U is —CH₂—,
A is phenyl, pyridyl, thienyl or thiazolyl which may optionally be mono- to trisubstituted by methyl, ethyl, n-propyl, i-propyl, n-butyl, i-butyl, s-butyl, t-butyl, CF₃, methoxy, ethoxy, F, Cl, Br,
R² is COOR²⁴,
in which
  R²⁴ is hydrogen or straight-chain or branched alkyl having up to 4 carbon atoms,
X is straight-chain or branched alkylene having up to 8 carbon atoms or straight-chain or branched alkenediyl having up to 8 carbon atoms which may in each case contain one to three groups from the group consisting of phenyl, phenyloxy, O, CO and CONR³⁰,
in which
  R³⁰ is hydrogen, straight-chain or branched alkyl having up to 6 carbon atoms or cycloalkyl having 3 to 6 carbon atoms,
n is 1 or 2,
R¹ is COOR³⁵,
in which
  R³⁵ is hydrogen or straight-chain or branched alkyl having up to 6 carbon atoms.

Very particular preference is given here to compounds of the formula (I),
in which
V is O,
Q is straight-chain or branched alkylene having up to 9 carbon atoms or straight-chain or branched alkenediyl or straight-chain or branched alkinediyl having up to 4 carbon atoms which may be monosubstituted by halogen,
Y is H, cyclohexyl, phenyl or a heterocycle from the group consisting of

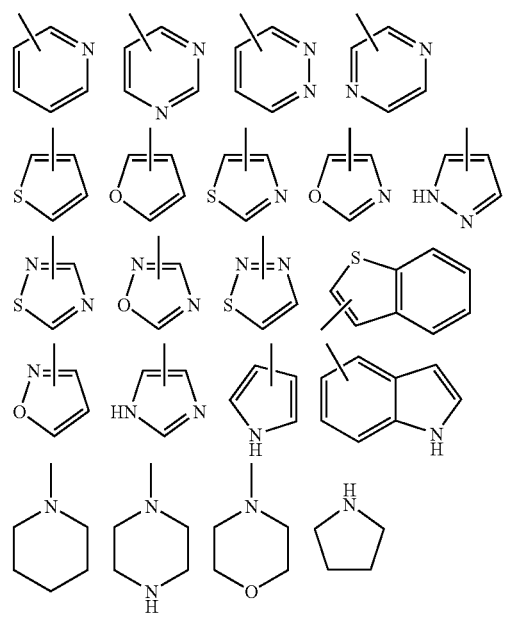

where the cyclic radicals may in each case be mono- to trisubstituted by straight-chain or branched alkyl, straight-chain or branched alkenyl, straight-chain or branched alkinyl, straight-chain or branched alkoxy, straight-chain or branched alkoxyalkoxy, straight-chain or branched halogenoalkyl, straight-chain or branched halogenoalkoxy having in each case up to 4 carbon atoms, straight-chain or branched cycloalkyl having 3 to 6 carbon atoms, F, Cl, Br, I, $NO_2$, $SR^6$, $NR^8R^9$, $NR^7COR^{10}$ or $CONR^{11}R^{12}$, in which $R^6$ is hydrogen, straight-chain or branched alkyl having up to 4 carbon atoms or straight-chain or branched halogenoalkyl having up to 4 carbon atoms, $R^7$ is hydrogen, or straight-chain or branched alkyl having up to 4 carbon atoms, $R^8$, $R^9$, $R^{11}$ and $R^{12}$ independently of one another are hydrogen, straight-chain or branched alkyl having up to 4 carbon atoms or phenyl, where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN, or two substituents $R^8$ and $R^9$ or $R^{11}$ and $R^{12}$ may be attached to one another forming a five- or six-membered ring which may be interrupted by O or N, $R^{10}$ is hydrogen, straight-chain or branched alkyl having up to 4 carbon atoms or phenyl, where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;

and/or the cyclic radicals may in each case be mono- to trisubstituted by phenyl or a heterocycle from the group consisting of

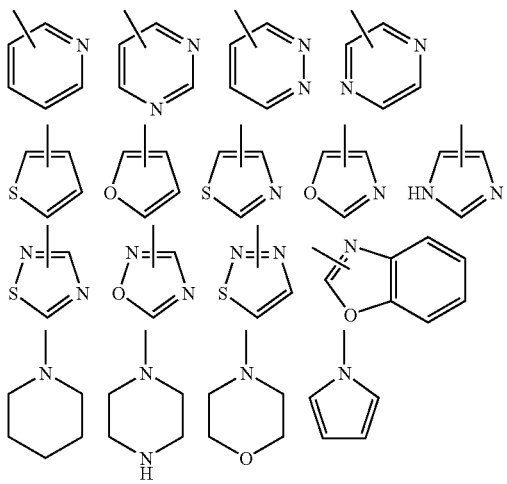

which may be attached directly or via a group O, S, SO, $SO_2$, straight-chain or branched alkylene, straight-chain or branched alkenediyl, straight-chain or branched alkyloxy, straight-chain or branched oxyalkyloxy, straight-chain or branched sulphonylalkyl, straight-chain or branched thioalkyl having in each case up to 4 carbon atoms and which may be mono- to trisubstituted by straight-chain or branched alkyl, straight-chain or branched alkoxy, straight-chain or branched alkoxyalkoxy, straight-chain or branched halogenoalkyl or straight-chain or branched alkenyl having in each case up to 4 carbon atoms, F, Cl, Br, I, CN, $SCH_3$, $OCF_3$, $NO_2$, $NR^8R^9$ or $NR^{14}COR^{17}$, in which $R^{14}$ is hydrogen, straight-chain or branched alkyl having up to 6 carbon atoms or cycloalkyl having 3 to 6 carbon atoms, and $R^{17}$ is hydrogen, straight-chain or branched alkyl having up to 6 carbon atoms, straight-chain or branched alkenyl having up to 6 carbon atoms, aryl having 6 to 10 carbon atoms, an aromatic heterocycle having 1 to 9 carbon atoms and up to 3 heteroatoms from the group consisting of S, N and O or cycloalkyl having 3 to 6 carbon atoms, which may furthermore optionally be substituted by F, Cl, Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;

and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O, $R^3$ is hydrogen or fluorine, m is an integer from 1 to 2, W is —$CH_2$— or —$CH_2CH_2$—, U is —$CH_2$—, A is phenyl which may optionally be mono- to trisubstituted by methyl, ethyl, n-propyl, i-propyl, n-butyl, i-butyl, s-butyl, t-butyl, $CF_3$, methoxy, ethoxy, F, Cl, Br, $R^2$ is $COOR^{24}$, in which $R^{24}$ is hydrogen or straight-chain or branched alkyl having up to 4 carbon atoms, X is straight-chain or branched alkylene having up to 6 carbon atoms or straight-chain or branched alkenediyl having up to 6 carbon atoms, which may each contain one to three groups from the group consisting of phenyloxy, O, CO and $CONR^{30}$, in which $R^{30}$ is hydrogen, straight-chain or branched alkyl having up to 6 carbon atoms or cycloalkyl having 3 to 6 carbon atoms, n is 1 or 2, $R^1$ is $COOR^{35}$, in which $R^{35}$ is hydrogen or straight-chain or branched alkyl having up to 4 carbon atoms.

Particular preference according to the invention is given to compounds of the formula (I), in which $R^1$ and $R^2$ are each COOH.

Very particular preference according to the present invention is given to compounds in which V is O, Q is $CH_2$, Y is phenyl which is substituted by a radical selected from the group consisting of 2-phenylethyl, cyclohexyl, 4-chlorophenyl, 4-methoxyphenyl, 4-trifluoromethylphenyl, 4-cyanophenyl, 4-chlorophenoxy, 4-methoxyphenoxy, 4-trifluoromethylphenoxy, 4-cyanophenoxy, 4-methylphenyl, $R^3$ is hydrogen or fluorine, m is an integer from 1 to 2, W is —$CH_2CH_2$—, U is —CH$_2$—, A is phenyl, R$^2$ is COOH, where R$^2$ is located in the 4-position to the radical U, X is (CH$_2$)$_4$, R$^1$ is COOH.

The compounds of the general formula (I) according to the invention may also be present in the form of their salts. In general, salts with organic or inorganic bases or acids may be mentioned here.

In the context of the present invention, preference is given to physiologically acceptable salts. Physiologically acceptable salts of the compounds according to the invention may be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, p-toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts may also be the metal or ammonium salts of the compounds according to the invention which have a free carboxyl group. Particular preference is given, for example, to sodium, potassium, magnesium or calcium salts, and to ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

The compounds according to the invention may exist in stereoisomeric forms which are either like image and mirror image (enantiomers) or which are not like image and mirror image (diastereomers). The invention relates both to the enantiomers or diastereomers and to their respective mixtures. The racemates, like the diastereomers, can be separated into stereoisomerically uniform components in a known manner, for example by optical resolution or chromatographic separation. Any double bonds present in the compounds according to the invention can be present in the cis or trans configuration (Z or E form).

In the context of the present invention, the substituents generally have, unless indicated otherwise, the following meanings:

Alkyl generally represents a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodecyl, eicosyl.

Alkylene generally represents a straight-chain or branched hydrocarbon bridge having 1 to 20 carbon atoms. Examples which may be mentioned are methylene, ethylene, propylene, α-methylethylene, β-methylethylene, α-ethylethylene, β-ethylethylene, butylene, α-methylpropylene, β-methylpropylene, γ-methylpropylene, α-ethylpropylene, β-ethylpropylene, γ-ethylpropylene, pentylene, hexylene, heptylene, octylene, nonylene, decylene, dodecylene and eicosylene.

Alkenyl generally represents a straight-chain or branched hydrocarbon radical having 2 to 20 carbon atoms and one or more, preferably one or two, double bonds. Examples which may be mentioned are allyl, propenyl, isopropenyl, butenyl, isobutenyl, pentenyl, isopentenyl, hexenyl, isohexenyl, heptenyl, isoheptenyl, octenyl, isooctenyl.

Alkinyl generally represents a straight-chain or branched hydrocarbon radical having 2 to 20 carbon atoms and one or more, preferably one or two, triple bonds. Examples which may be mentioned are ethinyl, 2-butinyl, 2-pentinyl and 2-hexinyl.

Alkenediyl generally represents a straight-chain or branched hydrocarbon bridge having 2 to 20 carbon atoms and one or more, preferably one or two, double bonds. Examples which may be mentioned are ethene-1,2-diyl, propene-1,3-diyl, propene-1,2-diyl, 1-butene-1,4-diyl, 1-butene-1,3-diyl, 1-butene-1,2-diyl, 2-butene-1,4-diyl, 2-butene-1,3-diyl, 2-butene-2,3-diyl.

Alkinediyl generally represents a straight-chain or branched hydrocarbon bridge having 2 to 20 carbon atoms and one or more, preferably one or two, triple bonds. Examples which may be mentioned are ethine-1,2-diyl, propine-1,3-diyl, 1-butine-1,4-diyl, 1-butine-1,3-diyl, 2-butene-1,4-diyl.

Acyl generally represents straight-chain or branched lower alkyl having 1 to 9 carbon atoms which is attached via a carbonyl group. Examples which may be mentioned are: acetyl, ethylcarbonyl, propylcarbonyl, isopropylcarbonyl, butylcarbonyl and isobutylcarbonyl.

Alkoxy generally represents a straight-chain or branched hydrocarbon radical having 1 to 14 carbon atoms which is attached via an oxygen atom. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy. The terms "alkoxy" and "alkyloxy" are used synonymously.

Alkoxyalkyl generally represents an alkyl radical having up to 8 carbon atoms which is substituted by an alkoxy radical having up to 8 carbon atoms.

Alkoxycarbonyl can be depicted, for example, by the formula

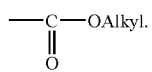

Alkyl here generally represents a straight-chain or branched hydrocarbon radical having 1 to 13 carbon atoms. The following alkoxycarbonyl radicals may be mentioned as examples: methoxycarbonyl, ethoxycarbonyl, propoxycarbonyl, isopropoxycarbonyl, butoxycarbonyl or isobutoxycarbonyl.

Cycloalkyl generally represents a cyclic hydrocarbon radical having 3 to 8 carbon atoms. Preference is given to cyclopropyl, cyclopentyl and cyclohexyl. Examples which may be mentioned are cyclopentyl, cyclohexyl, cycloheptyl and cyclooctyl.

Cycloalkoxy represents, in the context of the invention, an alkoxy radical whose hydrocarbon radical is a cycloalkyl radical. The cycloalkyl radical generally has up to 8 carbon atoms. Examples which may be mentioned are: cyclopropyloxy and cyclohexyloxy. The terms "cycloalkoxy" and "cycloalkyloxy" are used synonymously.

Aryl generally represents an aromatic radical having 6 to 10 carbon atoms. Preferred aryl radicals are phenyl and naphthyl.

Halogen represents, in the context of the invention, fluorine, chlorine, bromine and iodine.

Heterocycle generally represents, in the context of the invention, a saturated, unsaturated or aromatic 3- to 10-membered, for example 5- or 6-membered, heterocycle which may contain up to 3 heteroatoms from the group consisting of S, N and O and which, in the case of a nitrogen atom, may also be attached via this nitrogen atom. Examples which may be mentioned are: oxadiazolyl, thiadiazolyl, pyrazolyl, pyridyl, pyrimidinyl, pyridazinyl, pyrazinyl, thienyl, furyl, pyrrolyl, pyrrolidinyl, piperazinyl, tetrahydropyranyl, tetrahydrofuranyl, 1,2,3-triazolyl, thiazolyl, oxazolyl, imidazolyl, morpholinyl or piperidyl. Preference is given to thiazolyl, furyl, oxazolyl, pyrazolyl, triazolyl, pyridyl, pyrimidinyl, pyridazinyl and tetrahydropyranyl. The term "heteroaryl" (or "hetaryl") represents an aromatic heterocyclic radical.

In the heterocycle structures shown in the present application, in each case only one bond to the adjacent group is indicated, for example in the heterocycle structures suitable for Y the bond to the unit Q. However, as indicated, these heterocycle structures may, independently of this, carry further substituents.

The present invention furthermore relates to a process for preparing compounds of the formula (I), characterized in that
[A] compounds of the formula (II)

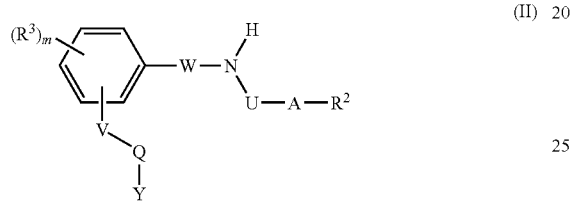

are reacted with compounds of the formula (III)

in which
R$^1$, R$^2$, R$^3$, V, Q, Y, W, X, U, A and m are as defined above,
E is either a leaving group which is substituted in the presence of a base or is an optionally activated hydroxyl function;
or
[B] compounds of the formula (IV)

are reacted with compounds of the formula (V)

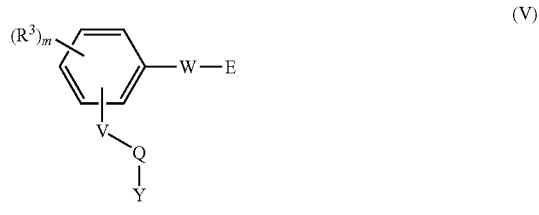

in which
R$^1$, R$^2$, R$^3$, V, Q, Y, W, X, U, A and m are as defined above,
E is either a leaving group which is substituted in the presence of a base or is an optionally activated hydroxyl function;

or
[C] compounds of the formula (VI)

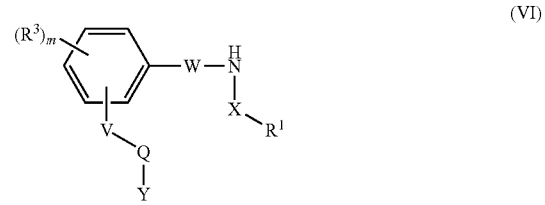

are reacted with compounds of the formula (VII)

E-U-A-R$^2$ (VII)

in which
R$^1$, R$^2$, R$^3$, V, Q, Y, W, X, U, A and m are as defined above,
E is either a leaving group which is substituted in the presence of a base or is an optionally activated hydroxyl function,
or
[D] compounds of the formula (VIII),

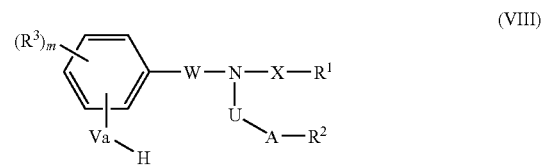

in which
Va is O or S and
R$^1$, R$^2$R$^3$, Y, Q, W, U, A, X and m are as defined in Claim 3,
are reacted with compounds of the formula (IX)

in which
Q, Y are as defined above,
E is either a leaving group which is substituted in the presence of a base or is an optionally activated hydroxyl function;
or
[E] compounds of the formula (X)

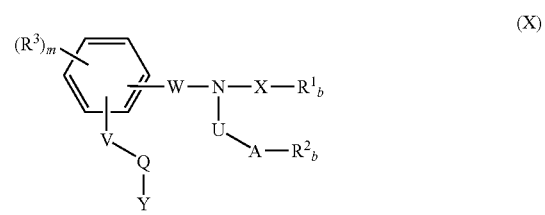

in which
R$^3$, V, Q, Y, W, X, U, A and m are as defined above,
R$^1_b$ and R$^2_b$ independently each represent CN or COOAlk, where Alk represents a straight-chain or branched alkyl radical having up to 6 carbon atoms, are converted with aqueous solutions of strong acids or strong bases into the corresponding free carboxylic acids;

or

[F] compounds of the formula (XI)

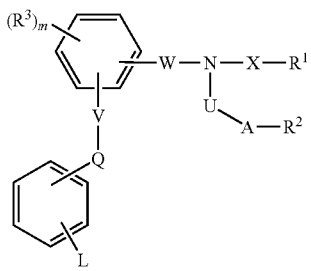

(XI)

in which

R$^1$, R$^2$, R$^3$, V, Q, X, W, U, A and m are as defined above,

L represents Br, I or the group CF$_3$SO$_2$—O, are reacted with compounds of the formula (XII)

M-Z (XII)

in which

M represents an aryl or heteroaryl radical, a straight-chain or branched alkyl, alkenyl or alkinyl radical or cycloalkyl radical or represents an arylalkyl, an arylalkenyl or an arylalkinyl radical, Z represents the groupings —B(OH)$_2$, —CH═CH, —CH═CH$_2$ or —Sn(nBu)$_3$, in the presence of a palladium compound, if appropriate additionally in the presence of a reducing agent and further additives and in the presence of a base;

or

[G] compounds of the formula (XIII)

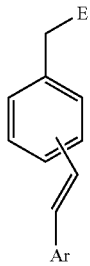

(XIII)

in which

Ar represents an aryl or heteroaryl radical,

E is a leaving group which is substituted in the presence of a base, are reacted according to process D with compounds of the formula (VIII) and the resulting compounds of the formula (XIV)

(XIV)

are hydrogenated with hydrogen in the presence of a catalyst.

The processes according to the invention for preparing compounds of the formula (I) are illustrated below using exemplary, non-limiting embodiments:

Example of the Reaction Sequence According to Processes A/E:

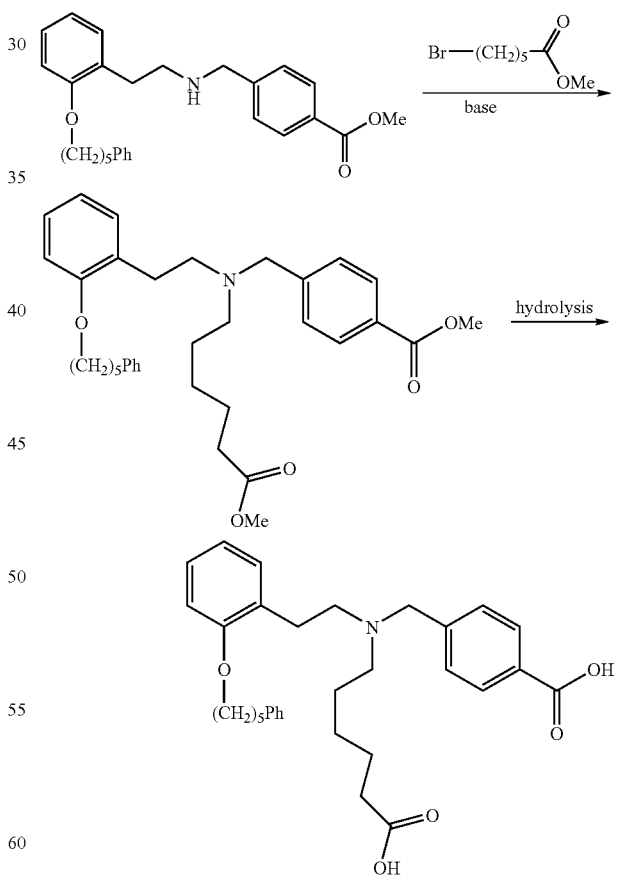

If (VIII) represents, for example, methyl 4-{[(2-methoxyphenethyl)amino]-methyl}benzoate and (IX) represents 2-chlorophenylmethyl chloride, processes D and E can be represented as shown in the scheme below:

Example of the Reaction Sequence According to Processes D/E:

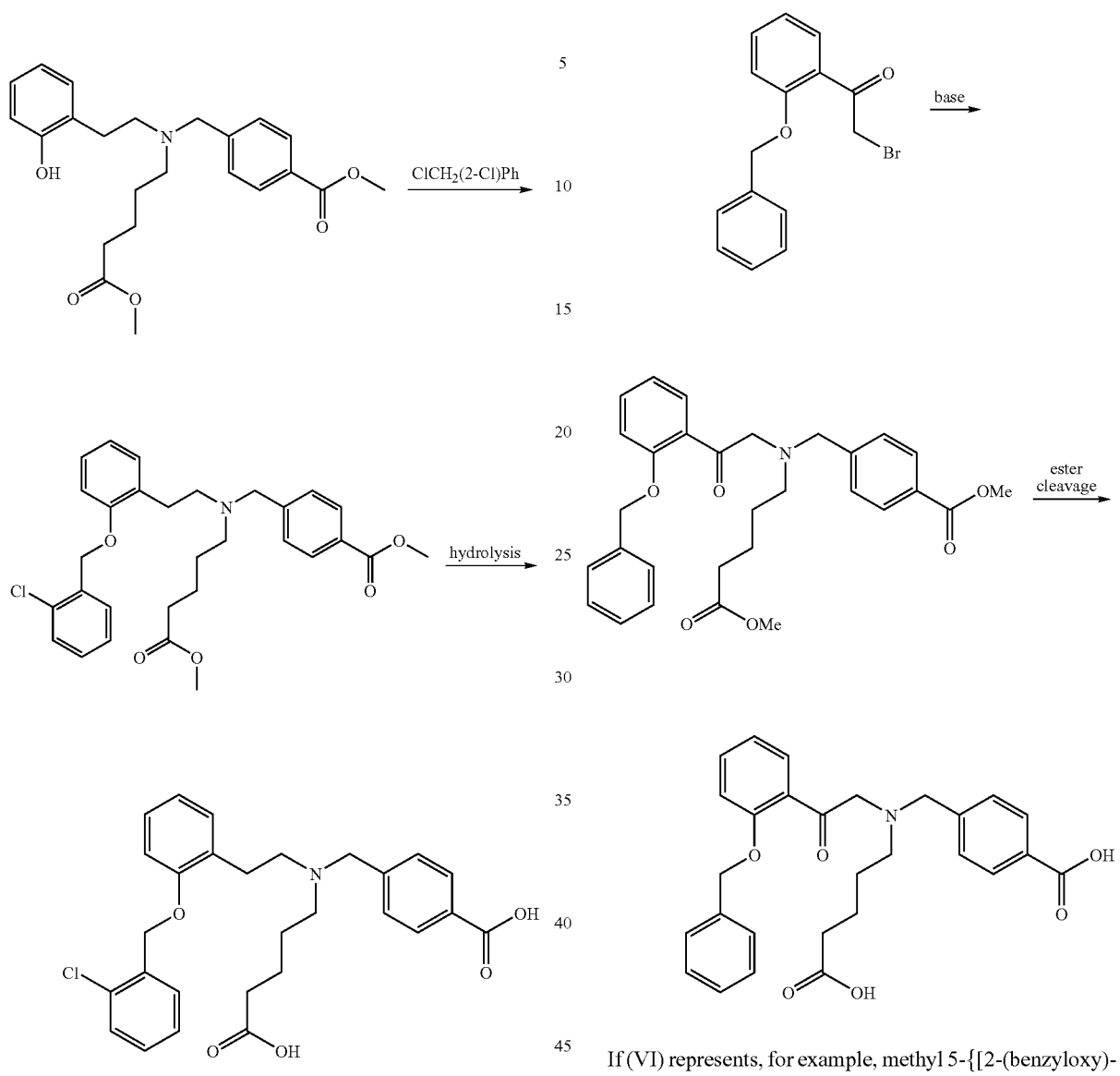

If (IV) represents, for example, methyl 4-{[(5-methoxy-5-oxypentyl)amino]-methyl}benzoate and (V) represents 1-[2-(benzyloxy)phenyl]-2-bromo-1-ethanone, processes B and E can be represented as shown in the scheme below:

Example of the Reaction Sequence According to Processes B/E:

If (VI) represents, for example, methyl 5-{[2-(benzyloxy)-phenethyl]amino}pentanoate and (VII) represents methyl 4-(bromomethyl)-benzoate, processes C and E can be represented as shown in the scheme below:

Example of the Reaction Sequence According to Processes C/E:

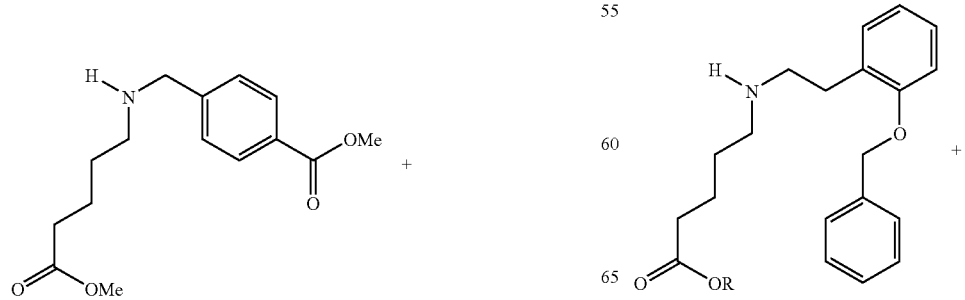

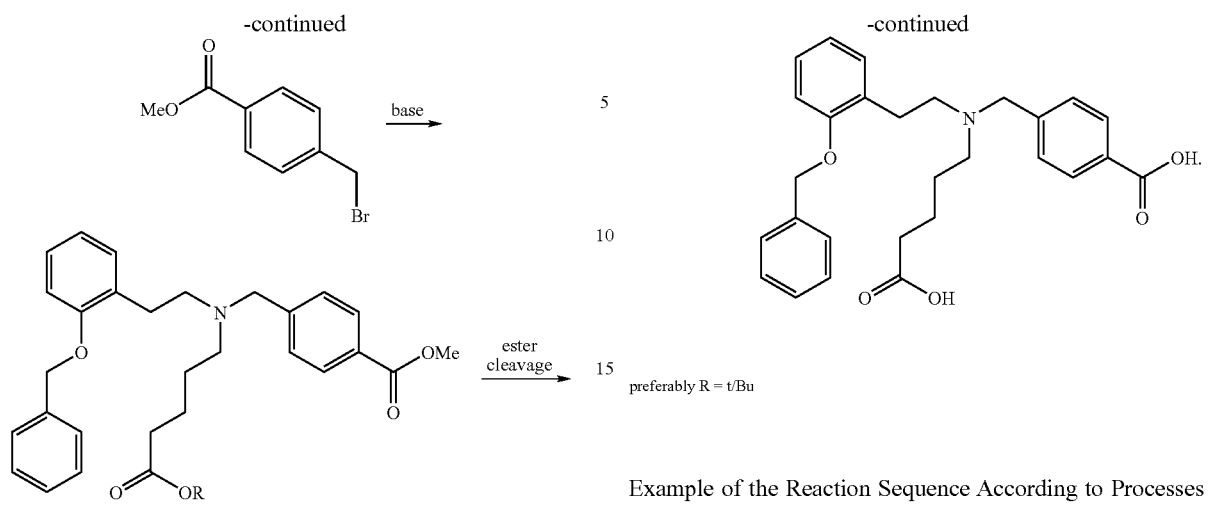
Example of the Reaction Sequence According to Processes D/F/E
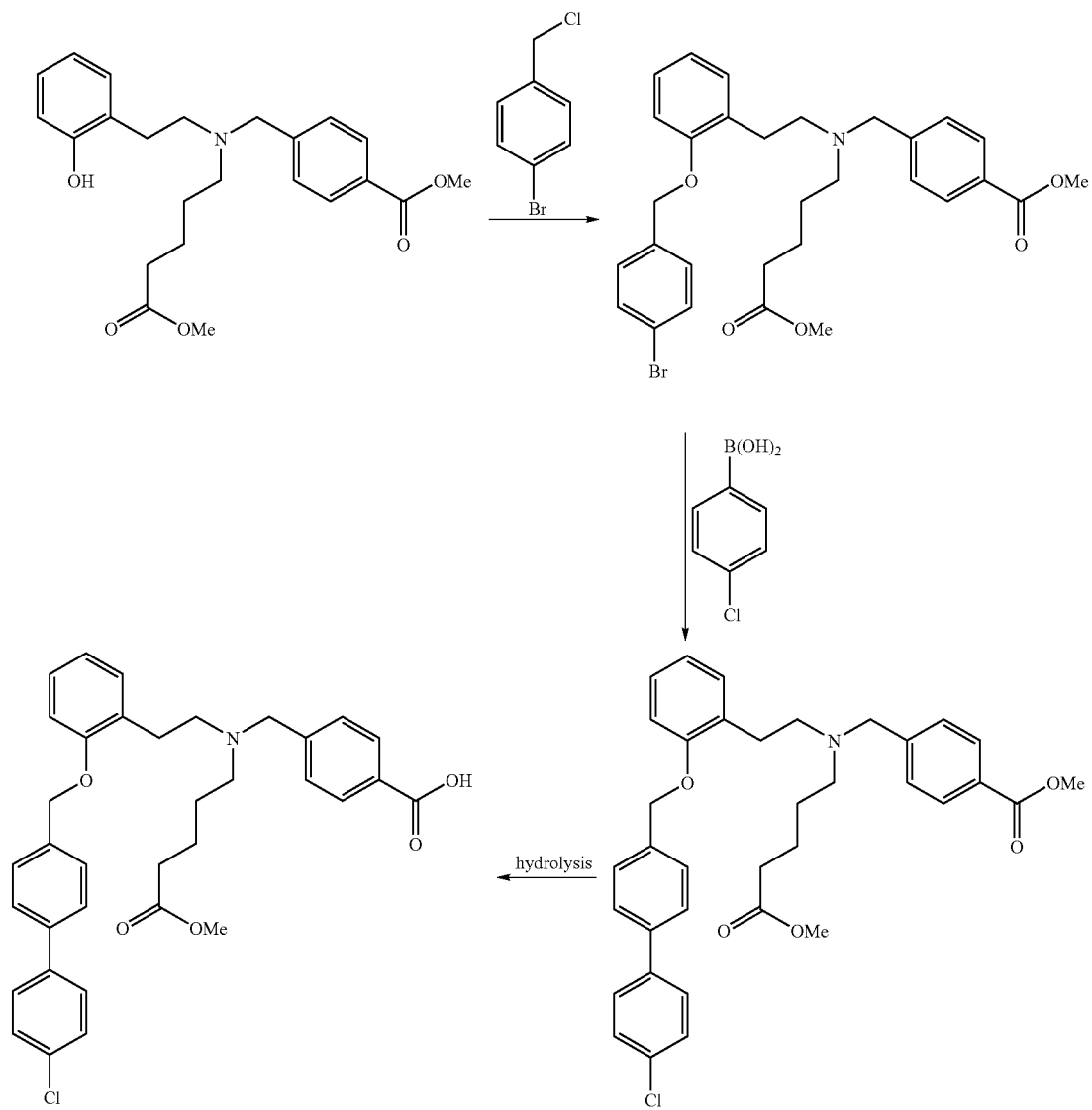

Example of the Reaction Sequence According to Processes D/G/E

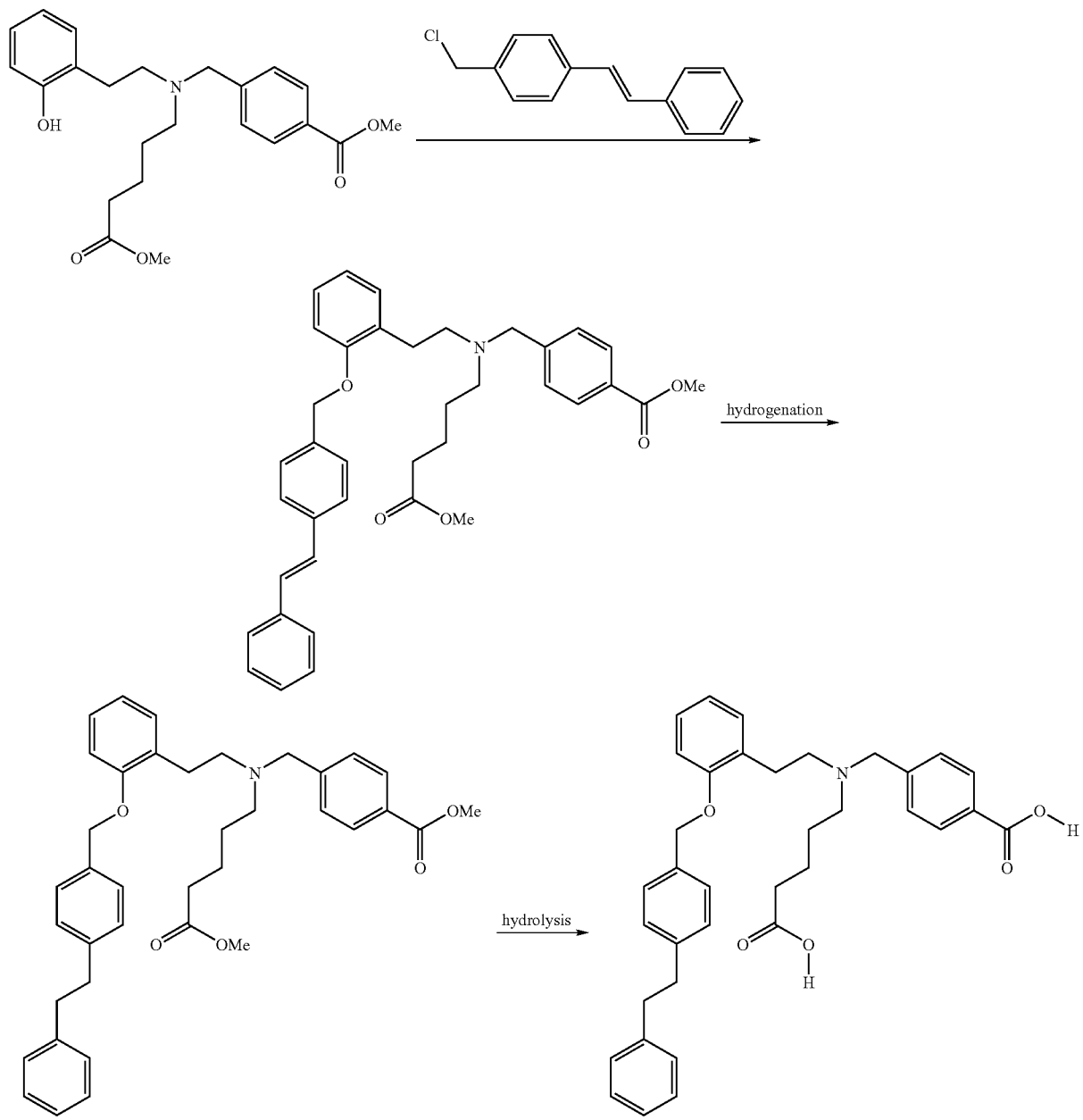

The solvents which are preferred for the processes according to the invention are customary organic solvents which do not change under the reaction conditions, or water. Preference may be given to using, for the processes according to the invention, ethers, such as diethyl ether, butyl methyl ether, dioxane, tetrahydrofuran, glycol dimethyl ether or diethylene glycol dimethyl ether, or hydrocarbons, such as benzene, toluene, xylene or petroleum ether, or amides, such as dimethylformamide or hexamethylphosphoric triamide, or 1,3-dimethyl-imidazolidin-2-one, 1,3-dimethyl-tetrahydropyrimidin-2-one, acetonitrile, ethyl acetate or dimethyl sulphoxide. It is, of course, also possible to use mixtures of the abovementioned solvents.

The bases which are preferred for the processes according to the invention include basic compounds which are customarily used for basic reactions. Preference may be given to using alkali metal hydrides, such as, for example, sodium hydride or potassium hydride, or alkali metal alkoxides, such as sodium methoxide, sodium ethoxide, potassium methoxide, potassium ethoxide or potassium t-butoxide, or carbonates, such as sodium carbonate, caesium carbonate or potassium carbonate, or amides, such as sodium amide or lithium diisopropylamide, or organolithium compounds, such as phenyllithium, butyllithium or methyllithium, or sodium hexamethyldisilazane.

The processes A to C according to the invention can preferably be carried out in acetonitrile, in each case by reacting the compounds (II) and (III), (IV) and (V) and (VI) and (VII), respectively, in the presence of a base, such as sodium carbonate, $Et_3N$, DABCO, $K_2CO_3$, KOH, NaOH or NaH. The reaction can generally be carried out in a temperature range of from −20° C. to +90° C., preferably from 0° C. to +70° C. The reaction can be carried out at atmospheric pressure, elevated or reduced pressure (for example in a range of from 0.5 to 5 bar). In general, the reaction is carried out at atmospheric pressure.

In the processes A to C according to the invention, a compound of the formula (I) is prepared by nucleophilic substitution of a leaving group E in one of the compounds of the formula (III), (V) or (VII) by the amine function of one of the compounds of the formula (II), (IV) or (VI). Suitable leaving groups E are, for example: halogen, tosylate, mesylate, or a hydroxyl function which is activated by reagents such as diisopropyl azodicarboxylate/$PPh_3$ (Mitsonobu reaction).

The process D according to the invention can preferably be carried out in acetonitrile by reacting the compounds (VIII) and (IX) in the presence of a base, such as sodium carbonate, potassium carbonate, $Et_3N$, DABCO, $K_2CO_3$, KOH, NaOH or NaH. The reaction can generally be carried out in a temperature range of from −20° C. to +90° C., preferably from 0° C. to +90° C. The reaction can be carried out at atmospheric pressure, elevated or reduced pressure (for example in a range of from 0.5 to 5 bar). In general, the reaction is carried out at atmospheric pressure.

In the process D according to the invention, a compound of the formula (I) is prepared by nucleophilic substitution of a leaving group E in the compound of the formula (IX) by the hydroxyl or thiol function of the compound of the formula (VIII). Suitable leaving groups E are, for example: halogen, tosylate, mesylate, or a hydroxyl function which is activated by reagents such as diisopropyl azodicarboxylate/$PPh_3$ (Mitsonobu reaction).

In the process E according to the invention, a compound of the formula (I), where $R^1$ and $R^2$ each represent a free carboxyl function, is obtained by converting ester and/or nitrile functions of the compound (X) into the corresponding free carboxyl functions. This reaction can be carried out, for example, by adding aqueous solutions of strong acids, such as, for example, HCl or $H_2SO_4$, or strong bases, such as, for example, NaOH, KOH or LiOH. The reaction can be carried out in one of the abovementioned organic solvents, in water or in mixtures of organic solvents or in mixtures of organic solvents with water. Preference according to the invention is given, for example, to carrying out the reaction in a mixture of water and methanol or dioxane. The reaction can generally be carried out in a temperature range of from −20° C. to +90° C., preferably from 0° C. to +90° C. The reaction can be carried out at atmospheric pressure, elevated or reduced pressure (for example in a range of from 0.5 to 5 bar). In general, the reaction is carried out at atmospheric pressure.

In the process F according to the invention, a compound of the formula (I) is prepared by reacting a compound of the formula (XI), which contains a substitutable group L, with a compound of the group (XII) in the presence of a palladium compound and, if appropriate, a reducing agent and further additives in basic medium. Formally, the reaction is a reductive coupling of the compounds of the formulae (XI) and (XII), as described, for example, in L. S. Hegedus, Organometallics in Synthesis, M. Schlosser, Ed., Wiley & Sons, 1994.

In the compounds of the formula (XI), the substitutable group L can, for example, be a halogen radical, such as Br or I, or a customary leaving group, such as, for example, a triflate radical.

The compounds of the formula (XII) contain a reactive group Z which can be selected from the group consisting of —$B(OH)_2$, —CH≡CH, —CH=$CH_2$ or —$Sn(nBu)_3$.

The palladium compound used can be a palladium (II) compound, such as, for example, $Cl_2Pd(PPh_3)_2$ or $Pd(OAc)_2$, or a palladium (0) compound, such as, for example, $Pd(PPh_3)_4$ or $Pd_2(dba)_3$. If required, it is possible to add additionally a reducing agent, such as, for example, triphenylphosphine, or other additives, such as, for example, Cu(I) Br, $NBu_4NCl$, LiCl or $Ag_3PO_4$, to the reaction mixture (cf. T. Jeffery, Tetrahedron Lett. 1985, 26, 2667-2670; T. Jeffery, J. Chem. Soc., Chem. Commun. 1984, 1287-1289; S. Bräse, A. deMejiere in "Metal-catalyzed cross-coupling reactions", Ed. F. Diederich, P. J. Stang, Wiley-VCH, Weinheim 1998, 99-166).

The reaction is carried out in the presence of a customary base, such as, for example, $Na_2CO_3$, NaOH or triethylamine. Suitable solvents are the organic solvents mentioned above, and particular preference is given to ethers, such as, for example, dimethoxyethane. The reaction can, in general, be carried out in a temperature range of from −20° C. to +90° C., preferably from 0° C. to +90° C. The reaction can be carried out at atmospheric pressure, elevated or reduced pressure (for example in a range of from 0.5 to 5 bar). In general, the reaction is carried out at atmospheric pressure.

In the process G according to the invention, compounds of the formula (I) are obtained by reacting compounds of the formula (XIII), which contain a leaving group E, with compounds of the formula (VIII) according to the process D according to the invention, followed by hydrogenation of the resulting compounds of the formula (XIV).

Thus, the first step of the process G proceeds analogously to the process D, but instead of the compounds of the formula (IX), compounds of the formula (XIII) are reacted here with the alcohols or thiols of the formula (XIII). This gives the unsaturated compounds of the formula (XIV), which can be converted by customary hydrogenation processes into the compounds of the formula (I).

Preference according to the invention is given to the hydrogenation of compounds of the formula (XIV) with hydrogen in the presence of a catalyst, such as, for example, Pd/carbon or PtO.

The process G can be carried out in one of the abovementioned organic solvents. Preference is given here to ethyl acetate. In general, the reaction can be carried out in a temperature range of from −20° C. to +90° C., preferably from 0° C. to +90° C. The reaction can be carried out at atmospheric pressure, elevated or reduced pressure (for example in a range of from 0.5 to 5 bar). In general, the reaction is carried out at atmospheric pressure.

The amines of the formulae II, IV and VI are novel and also form part of the subject-matter of the invention.

The novel compounds of the formulae II, IV and VI can be obtained in a generally known manner by the following methods:

a) by reacting amines of the formulae (XV), (XVI) and (XVII)

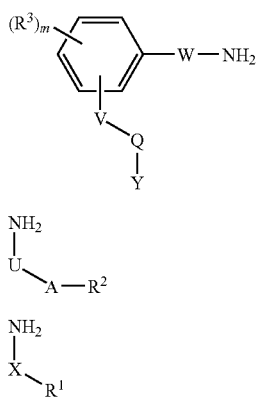

(XV)

(XVI)

(XVII)

where the radicals $R^1$, $R^2$, $R^3$, m, V, Q, U, W, X, Y and A are as defined above;

with carbonyl compounds of the formulae (XVIII), (XIX), (XX)

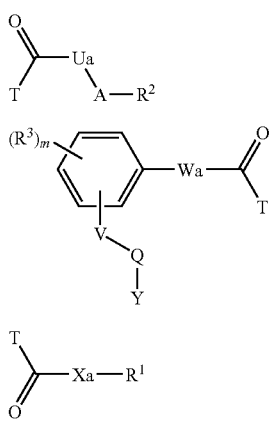

(XVIII)

(XIX)

(XX)

where

Ua, Wa and Xa have the meanings of U, W and X, respectively, but are one carbon unit shorter, and T represents hydrogen or a $C_1$-$C_4$-alkyl function, which can also be attached to Ua or Xa to form a cycle, and the other radicals are as defined above, initially to give a Schiff base which is then reduced with customary reducing agents, such as, for example, $NaBH_4$, $H_2/Pd/C$, etc., or converted directly under the conditions of a reductive alkylation in the presence of a reducing agent, such as, for example, $H_2/Pd/C$, $NaCNBH_3$, $NaH(OAc)_3$ (cf. Patai, Ed., The Chemistry of the Carbon-Nitrogen Double Bond, pp. 276-293 and literature cited therein);

b) by reacting amines of the formulae (XV), (XVI) and (XVII) with compounds of the formulae (III), (V), (VII) (cf., for example, J. March, Advanced Organic Chemistry, fourth Edition, Wiley, 1992, page 411 and the literature cited therein).

Amines of the formula (IIa) and compounds of the formula (VIII),

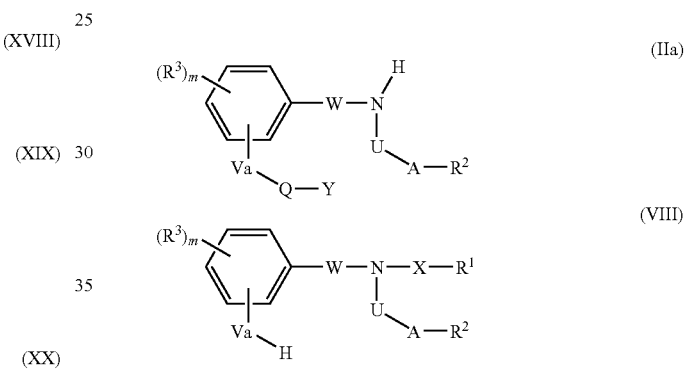

where Va represents O or S can be obtained in a generally known manner by the following reaction scheme:

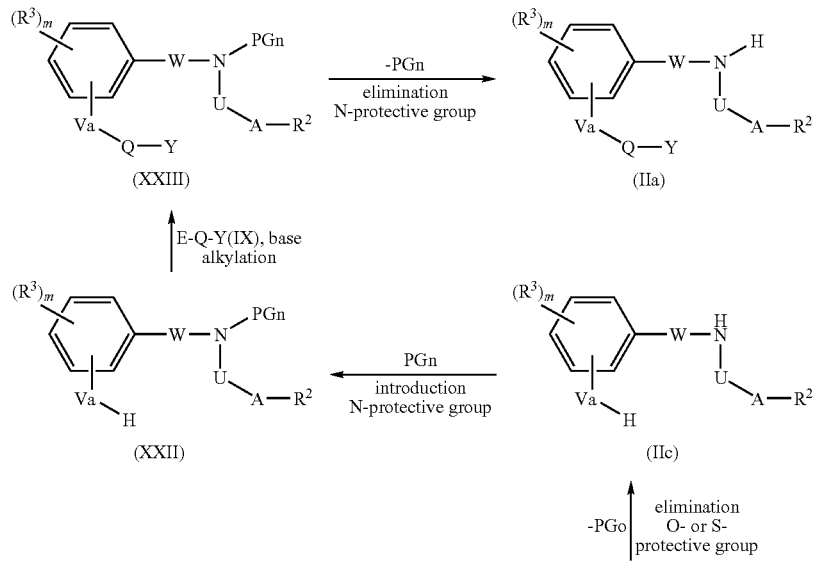

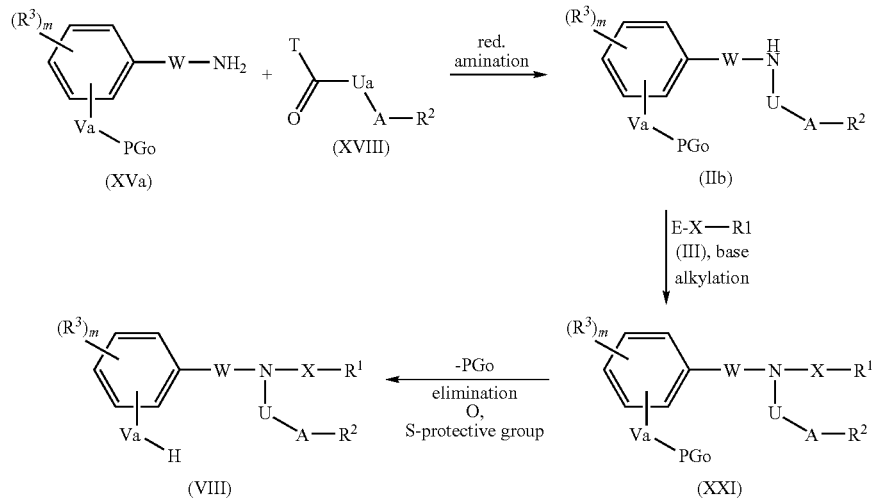

In the above scheme, PGo represents a customary phenol or thiophenol protective group, such as, for example, $CH_3$, $CH_2Ph$, $CH_2CH=CH_2$, $CH_2OCH_3$, $CH_2OCH_2SiMe_3$, $SiMe_3$, PGn represents an amine protective group, such as, for example, tBuOCO, T represents hydrogen or a $C_1$-$C_4$-alkyl function which can also be attached to Ua to form a cycle, and Ua has the meaning of U but is one $CH_2$ group shorter. The other radicals are as defined above.

(IIb) is obtained, for example, by initially reacting (XVa) with (XVIII) to give a Schiff base which is then reduced with customary reducing agents, such as, for example, $NaBH_4$, $H_2$/Pd/C, etc., or directly reacted under the conditions of a reductive alkylation in the presence of a reducing agent, such as, for example, $H_2$/Pd/C, $NaCNBH_3$ or $NaH(OAc)_3$. The compound (IIb) can be converted by reaction with a compound of the formula (III) in the presence of a base into a compound of the formula (XXI) (cf. process A).

An O- or S-protective group in (IIb) or (XXI) can be eliminated using a suitable reagent (cf. T. W. Greene, P. G. M. Wuts, Protective Groups in Organic Synthesis, second edition, New York, 1991). If, for example, in formula (IIb) or (XXI) -Va-PGo represents —O—$CH_3$, the methyl group can be eliminated with formation of the phenol using boron tribromide in methylene chloride at from −70 to 20° C., using trimethylsilyl iodide in chloroform at 25-50° C. or using sodium ethylthiolate in DMF at 150° C.

From the resulting compound of the formula (IIc), a compound of the formula (XXIII) can be obtained by protecting the amino function (cf. T. W. Greene, P. G. M. Wuts, Protective Groups in Organic Synthesis, second edition, New York, 1991) and subsequent reaction of the resulting amine-protected compound of the formula (XXII) with a compound of the formula (IX) (cf. process D).

An N-protective group such as in (XXII) can be introduced and removed again by customary methods (cf. T. W. Greene, P. G. M. Wuts, Protective Groups in Organic Synthesis, second edition, New York, 1991). If PGn in the formula (XXII) represents, for example, tBuOCO, the protective group can be introduced by reacting the amine with tert-butyl pyrocarbonate in polar or nonpolar solvents at from 0° C. to 25° C. Removal of the protective group to (IIa) can be carried out with numerous acids, such as, for example, HCl, $H_2SO_4$ or $CF_3COOH$, at from 0° to 25° C. (cf. the literature cited above).

Substances of the formula (III) are commercially available, known from the literature or synthesizable by processes known from the literature (cf. for example, J. Chem. Soc. 1958, 3065).

Substances of the formula (V) are known from the literature or synthesizable analogously to processes known from the literature (cf., for example, J. Med. Chem. 1989, 32, 1757; Indian J. Chem. Sect. B 1985, 24, 1015; Recl. Trav. Chim. Pays-Bas 1973, 92, 1281; Tetrahedron Lett. 1986, 37, 4327).

Substances of the formula (VII) are commercially available, known from the literature or synthesizable analogously to processes known from the literature (cf., for example, J. Org. Chem. 1959, 24, 1952; Collect Czech. Chem. Commun 1974, 39, 3527; Helv. Chim. Acta 1975, 58, 682; Liebigs Ann. Chem. 1981, 623).

Substances of the formula (IX) are commercially available, known from the literature or synthesizable analogously to processes known from the literature (cf., for example, J. prakt. Chem. 1960, 341; Farmaco Ed. Sci. 1956, 378; Eur. J. Med. Chem. Chim. Ther. 1984, 19, 205; Bull. Soc. Chim. Fr. 1951, 97. Liebigs Ann. Chem. 1954, 586, 52; EP-A-0 334 137). In particular, 4-chloromethylbiphenyl compounds which carry a further substituent in the 4'-position can be prepared by coupling 4-$(B(OH)_2)$-Ph-CHO with the corresponding 4-substituted bromophenyl compounds in the presence of palladium catalysts, such as, for example, $Pd(PPh_3)_4$ or $PdCl_2(PPh_3)_2$ and sodium carbonate to give the corresponding biphenyl compounds, followed by reduction to give the alcohol using $NaBH_4$ and conversion into the corresponding chloride using, for example, $SOCl_2$.

If E in the formulae (III), (V), (VII) and (IX) represents halogen, the compounds can also be prepared by generally known processes, for example by reaction of an alcohol with a chlorinating agent, such as, for example, thionyl chloride or sulphuryl chloride, (cf., for example, J. March, Advanced Organic Chemistry, fourth Edition, Wiley, 1992, page 1274 and the literature cited therein).

Amines of the formula (XV) are commercially available, known from the literature or synthesizable analogously to processes known from the literature (cf., for example, Tetrahedron 1997, 53, 2075; J. Med. Chem. 1984, 27, 1321; WO97/29079; J. Org. Chem. 1982, 47, 5396). These compounds can be obtained, for example, from the corresponding halide compounds and in particular chloride compounds where, instead of the radicals W—$NH_2$ of the compounds of the formula (XV), a group W'-Hal is present in which W' is a radical W which is shortened by one C atom, by substitution of the halide radical by a cyano group, giving the corresponding nitrile compounds, and reduction of the nitrile group, or by reaction of the corresponding aldehyde compounds in which, instead of the radicals W—$NH_2$ of the compounds of the formula (XV), a group W'—CHO is present where W' is a radical W which is shortened by one C atom, with nitromethane, and subsequent reduction.

Amines of the formula (XVI) are commercially available, known from the literature or synthesizable analogously to processes known from the literature (cf., for example, J. Am. Chem. Soc. 1982, 104, 6801; Chem. Lett. 1984, 1733; J. Med. Chem. 1998, 41, 5219; DE-2059922).

Amines of the formula (XVII) are commercially available, known from the literature or synthesizable analogously to processes known from the literature (cf., for example, J. Org. Chem. 1968, 33, 1581; Bull. Chem. Soc. Jpn. 1973, 46, 968; J. Am. Chem. Soc. 1958, 80, 1510; J. Org. Chem. 1961, 26, 2507; Synth. Commun. 1989, 19, 1787).

Amines of the formulae (XV), (XVI) and (XVII) can also be prepared by generally known processes, for example by reduction of a corresponding nitrile, by reacting a corresponding halide with phthalimide and subsequent reaction with hydrazine or by the rearrangement of acyl azides in the presence of water (cf., for example, J. March, Advanced Organic Chemistry, fourth Edition, Wiley, 1992, page 1276 and the literature cited therein).

Carbonyl compounds of the formula (XVIII) are commercially available, known from the literature or synthesizable analogously to processes known from the literature (cf., for example, J. Med. Chem. 1989, 32, 1277; Chem. Ber. 1938, 71, 335; Bull. Soc. Chim. Fr. 1996, 123, 679).

Carbonyl compounds of the formula (XIX) are commercially available, known from the literature or synthesizable analogously to processes known from the literature (cf., for example, WO96/11902; DE-2209128; Synthesis 1995, 1135; Bull. Chem. Soc. Jpn. 1985, 58, 2192).

Carbonyl compounds of the formula (XX) are commercially available, known from the literature or synthesizable analogously to processes known from the literature (cf., for example, Synthesis 1983, 942; J. Am. Chem. Soc. 1992, 114, 8158).

Carbonyl compounds of the formulae (XVIII), (XIX) and (XX) can also be prepared by generally known processes, for example by oxidation of alcohols, reduction of acyl chlorides or reduction of nitrites (cf., for example, J. March, Advanced Organic Chemistry, fourth Edition, Wiley, 1992, page 1270 and the literature cited therein).

Compounds of the formula (XII) are commercially available, known from the literature or synthesizable analogously to processes known from the literature (cf., for example, for aromatic boronic acids: J. Chem. Soc. C 1966, 566. J. Org. Chem., 38, 1973, 4016; or for tributyltin compounds: Tetrahedron Lett. 31, 1990, 1347).

Compounds of the formula (XIII) are commercially available, known from the literature or synthesizable analogously to processes known from the literature (cf., for example, J. Chem. Soc. Chem. Commun., 17, 1994, 1919).

The compounds according to the invention, in particular the compounds of the general formula (I), have an unforeseeable useful pharmacological activity spectrum.

The compounds according to the invention, in particular the compounds of the general formula (I), effect a relaxation of the vessels, inhibit platelet aggregation and lower the blood pressure, and also increase coronary blood flow. These effects are mediated via direct stimulation of soluble guanylate cyclase and intracellular cGMP increase.

They can therefore be employed in medicaments for the treatment of cardiovascular disorders, such as, for example, for the treatment of hypertension and cardiac insufficiency, stable and unstable angina pectoris, peripheral and cardiac vascular disorders, arrhythmias, for the treatment of thromboembolic disorders and ischaemias, such as myocardial infarct, stroke, transitory and ischaemic attacks, peripheral circulatory disorders, prevention of restenoses such as after thrombolysis therapy, percutaneous transluminal angioplasty (PTA), percutaneous transluminal coronary angioplasty (PTCA), bypass and also for the treatment of arteriosclerosis, fibrotic disorders, such as hepatic fibrosis or pulmonary fibrosis, asthmatic disorders and disorders of the urogenital system, such as, for example, prostate hypertrophy, erectile dysfunction, female sexual dysfunction and incontinence, and also for the treatment of glaucoma.

The compounds described in the present invention, in particular the compounds of the general formula (I), are also active compounds for controlling disorders in the central nervous system which are characterized by disturbances of the NO/cGMP system. In particular, they are suitable for eliminating cognitive deficits, for improving learning and memory performance and for treating Alzheimer's disease. They are also suitable for the treatment of disorders of the central nervous system, such as states of anxiety, tension and depression, sleeping disorders and sexual dysfunction caused by the central nervous system, and for regulating pathological eating disorders or disorders associated with the use of stimulants and drugs.

Furthermore, the active compounds are also suitable for regulating cerebral circulation, and they are therefore effective agents for controlling migraine.

They are also suitable for the prophylaxis and control of sequelae of cerebral infarct (Apoplexia cerebri) such as stroke, cerebral ischaemias and skull-brain trauma. The compounds according to the invention, in particular the compounds of the general formula (I), can also be employed for controlling pain.

Additionally, the compounds according to the invention have antiinflammatory action and can therefore be employed as antiinflammatories.

Vasal Relaxant Action In Vitro

Rabbits are anaesthetized by intravenous injection of thiopental sodium or killed (about 50 mg/kg) and exsanguinated. The arteria saphena is removed and divided into 3 mm wide rings. The rings are individually mounted on in each case one triangular pair of hooks, open at the end, made of 0.3 mm strong special wire (Remanium®). Under a pretension, each ring is transferred into 5 ml organ baths containing a warm, carbogen-aerated Krebs-Henseleit solution at 37° C. having the following composition (mM): NaCl: 119; KCl: 4.8; $CaCl_2 \times 2H_2O$: 1; $MgSO_4 \times 7\ H_2O$: 1.4; $KH_2PO_4$: 1.2; $NaHCO_3$: 25; glucose: 10; bovine serum albumin: 0.001%. The contractility is detected using Statham UC2 cells, amplified and digitalized by means of A/D converters (DAS-1802 HC, Keithley Instruments Munich), and recorded in parallel on linear recorders. Contractions are induced by addition of phenylephrin.

After several (in general 4) control cycles, the substance to be investigated is added in each further passage in increasing dosage, and the height of the contraction achieved under the influence of the test substance is compared with the height of the contraction achieved in the last preliminary passage. From this, the concentration which is necessary in order to reduce the contraction achieved in the preliminary control by 50% (($IC_{50}$) is calculated. The standard administration volume is 5 μl. The proportion of DMSO in the bath solution corresponds to 0.1%.

The results are shown in Table 1:

TABLE 1 vasorelaxant action in vitro

| Example | $IC_{50}$ (nM) |
|---|---|
| 8 | 0.4 |
| 28 | 2.8 |
| 30 | 17 |
| 32 | 6.5 |
| 33 | 0.5 |
| 37 | 830 |
| 56 | 73 |
| 70 | 0.2 |
| 72 | 29 |
| 76 | 29 |
| 86 | 0.4 |
| 87 | 0.5 |
| 88 | 0.4 |
| 98 | 3.4 |
| 102 | 0.2 |
| 103 | 3.9 |
| 186 | 0.90 |

Stimulation of Recombinant Soluble Guanylate Cyclase (sGC) In Vitro

The investigations on the stimulation of recombinant soluble guanylate cyclase (sGC) and the compounds according to the invention with and without sodium nitroprusside and with and without the haem-dependent sGC inhibitor 1H-1,2,4-oxadiazole-(4,3a)-quinoxalin-1-one (ODQ) were carried out by the method described in detail in the following literature reference: M. Hoenicka, E. M. Becker, H. Apeler, T. Sirichoke, H. Schroeder, R. Gerzer and J.-P. Stasch: Purified soluble guanylyl cyclase expressed in a baculovirus/Sf9 system: stimulation by YC-1, nitric oxide, and carbon oxide. J. Mol. Med. 77 (1999): 14-23.

Haem-free guanylate cyclase was obtained by adding Tween 20 to the sample buffer (final concentration 0.5%).

Activation of sGC by a test substance is stated as n-fold stimulation of basal activity.

The results are shown in Table 2.

TABLE 2

Stimulation of recombinant soluble guanylate cyclase (sGC) in vitro

| Ex. 87 concentration (μM) | Stimulation (n-fold) Haem-containing sGC | | | Haem-free sGC | |
|---|---|---|---|---|---|
| | basal | +SNP (0.1 μM) | +ODQ (10 μM) | basal | +ODQ (10 μM) |
| 0 | 1 | 15 | 1 | 1 | 1 |
| 0.1 | 15 | 41 | 132 | 353 | 361 |
| 1.0 | 18 | 47 | 115 | 491 | 457 |
| 10 | 24 | 60 | 181 | 529 | 477 |

It can be seen from Table 2 that stimulation both of the haem-containing and of the haem-free enzyme is achieved. Furthermore, a combination of sGC stimulator and sodium nitroprusside (SNP), an NO donor, does not show any synergistic effect, i.e. the effect of SNP is not potentiated, as would be expected for an sGC stimulator acting via a haem-dependent mechanism. In addition, the effect of the sGC stimulator according to the invention is not blocked by the haem-dependent inhibitor of soluble guanylate cyclase, ODQ. Thus, the results in Table 2 demonstrate the novel mechanism of action of the stimulators according to the invention of soluble guanylate cyclase.

The present invention includes pharmaceutical preparations which, in addition to non-toxic, inert, pharmaceutically acceptable excipients, contain the compounds according to the invention, in particular the compounds of the general formula (I), and also processes for the production of these preparations.

The active compounds can optionally be present in one or more of the excipients indicated above and also in microencapsulated form.

The therapeutically active compounds, in particular the compounds of the general formula (I), should be present in the abovementioned pharmaceutical preparations in a concentration from approximately 0.1 to 99.5, preferably from approximately 0.5 to 95, % by weight of the total mix.

In addition to the compounds according to the invention, in particular the compounds of the general formula (I), the abovementioned pharmaceutical preparations can also contain other pharmaceutically active compounds.

In general, it has proved advantageous both in human and in veterinary medicine to administer the active compound(s) according to the invention in total amounts of from approximately 0.5 to approximately 500, preferably 5 to 100, mg/kg of bodyweight every 24 hours, if appropriate in the form of several individual doses, to achieve the desired results. An individual dose contains the active compound(s) according to the invention preferably in amounts from approximately 1 to approximately 80, in particular 3 to 30, mg/kg of bodyweight.

Below, the present invention is illustrated in more detail using non-limiting, preferred examples. Unless indicated otherwise, all amounts given refer to percent by weight.

EXAMPLES

Abbreviations

RT: Room temperature
EA: Ethyl acetate
BABA: n-Butyl acetate/n-butanol/glacial acetic acid/phosphate buffer pH 6 (50:9:25.15; org. phase)

Mobile Phases for Thin-Layer Chromatography:
Ti E1: Toluene/ethyl acetate (1:1)
TI EtOH 1: Toluene/methanol (1:1)
C1 E1: Cyclohexane/ethyl acetate (1:1)
C1 E2: Cyclohexane/ethyl acetate (1:2)

Starting Materials

Examples I-IV

Compounds of the Formula VIII

I.1. Methyl 4-{[(2-methoxyphenethyl)amino]methyl}benzoate

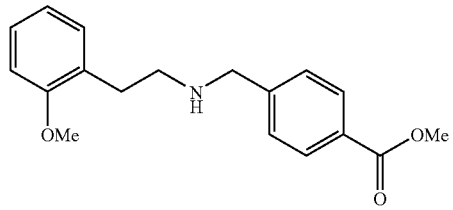

A solution of 9.23 g (56.16 mmol) of 2-methoxyphenethylamine and 9.219 g (56.16 mmol) of methyl 4-formylbenzoate in 35 ml of ethanol is heated at reflux for two hours. The solvent is distilled off under reduced pressure, giving 17.5 g of the imine which is reacted further without further purification.

17.5 g (58.85 mmol) of the imine are dissolved in 200 ml of methanol and, a little at a time, admixed with 4.45 g (117.7 mmol) of sodium borohydride. The reaction mixture is stirred at room temperature for two hours and then poured into water and extracted with ethyl acetate, and the organic phases are washed with saturated sodium chloride solution and dried. Distillative removal of the solvent under reduced pressure gives the product as an oil.

Yield: 16.04 g (91% of theory).

$^1$H-NMR (200 MHz, d$^6$-DMSO): δ=2.70 (m, 4H), 3.80 (s, 3H), 3.85 (s, 3H), 6.90 (m, 2H), 7.15 (m, 2H), 7.45 (d, 2H), 7.90 (s, 2H).

I.2. Methyl 4-{[(5-ethoxy-5-oxopentyl)(2-methoxyphenethyl)amino]methyl}benzoate

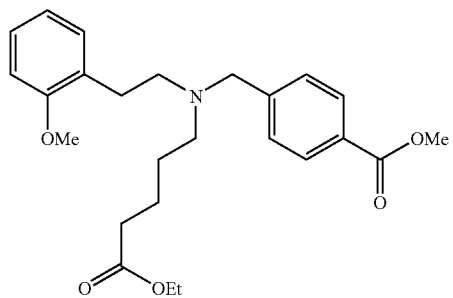

15.0 g (50.0 mmol) of methyl 4-{[(2-methoxyphenethyl)amino]methyl}benzoate from Example I.1., 11.52 g (55.0 mmol) of ethyl 5-bromovalerate and 6.37 g (106.0 mmol) of sodium carbonate are dissolved in 30 ml of acetonitrile and heated at reflux for 18 hours. After cooling, most of the solvent is distilled off under reduced pressure and the residues are mixed with water. The mixture is extracted repeatedly with ethyl acetate, the organic phases are washed with saturated sodium chloride solution and, after drying over magnesium sulphate, the solvent is removed under reduced pressure. The crude product is purified by flash chromatography over silica gel (0.04-0.063 nm) using the mobile phase cyclohexane/ethyl acetate 4/1.

Yield: 17.77 g (80.4% of theory)

$^1$H-NMR (200 MHz, d$^6$-DMSO): δ=1.13 (t, 3H), 1.45 (m, 4H), 2.20 (t, 2H), 2.45 (t, 2H), 2.58 (m, 2H), 2.70 (m, 2H), 3.70 (s, 3H), 3.85 (s, 3H), 4.05 (q, 2H), 6.8-6.9 (m, 2H), 7.0-7.2 (m, 2H), 7.40 (d, 2H), 7.86 (d, 2H).

I. Methyl 4-{[(2-hydroxyphenethyl)(5-methoxy-5-oxopentyl)amino]methyl}-benzoate

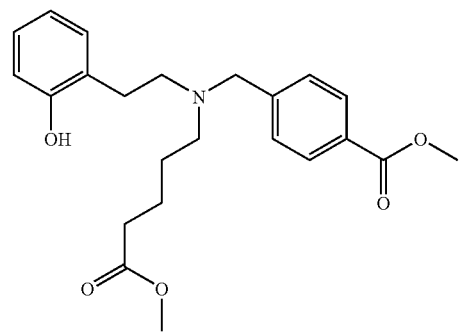

A solution of 3.00 g (7.02 mmol) of methyl 4-{[(5-ethoxy-5-oxopentyl)(2-methoxy-phenethyl)amino]methyl}benzoate from Example 1.2 in 60 ml of methylene chloride is cooled to 0° C., and 23.16 ml (23.16 mmol) of a 1N boron tribromide solution in methylene chloride are added dropwise. The solution is stirred at 0° C. for one hour. After addition of 30 ml of dry methanol, the batch is heated at 60° C. for one hour. After cooling, the solvent is removed under reduced pressure and the residue is taken up in a mixture of 57 ml of ethyl acetate and 3 ml of methanol and made alkaline using 10% sodium carbonate solution. The aqueous phase is extracted repeatedly with ethyl acetate/methanol 9/1 and the combined organic phases are washed using saturated sodium chloride solution. After drying over magnesium sulphate and distillative removal of the solvent under reduced pressure, the crude product is purified by flash chromatography over silica gel (0.04-0.063 nm) using the mobile phase cyclohexane/ethyl acetate 2/1.

Yield: 1.89 g (64.2% of theory)

$^1$H-NMR (200 MHz, d$^6$-DMSO): δ=1.46 (m, 4H), 2.23 (t, 2H), 2.45 (t, 2H), 2.60 (m, 2H), 2.70 (m, 2H), 3.60 (s, 3H), 3.70 (s, 2H), 3.85 (s, 3H), 6.70 (m, 2H), 7.01 (m, 2H), 7.45 (d, 2H), 7.90 (d, 2H), 9.50 (s, 1H).

The following compounds were obtained in the same manner:

II. Methyl 4-{[(5-ethoxy-5-oxopentyl)(2-hydroxybenzyl)amino]methyl}benzoate

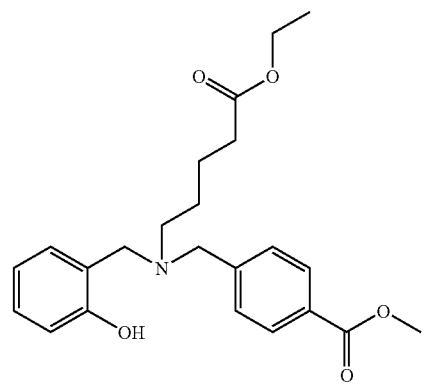

This compound can be obtained analogously to Example I starting from 2-methoxybenzylamine instead of 2-methoxyphenethylamine.

$^1$H-NMR (200 MHz, d$^6$-DMSO): δ=1.15 (t, 3H), 1.50 (m, 4H), 2.15 (m, 2H), 2.40 (m, 2H), 3.65 (s, 4H), 3.85 (s, 3H), 4.01 (q, 2H), 6.75 (t, 2H), 7.0-7.2 (m, 2H), 7.45 (d, 2H), 7.94 (d, 2H), 10.0 (br. s, 1H)

III. Methyl 4-{[(5-ethoxy-5-oxopentyl)(3-hydroxyphenethyl)amino]methyl}benzoate

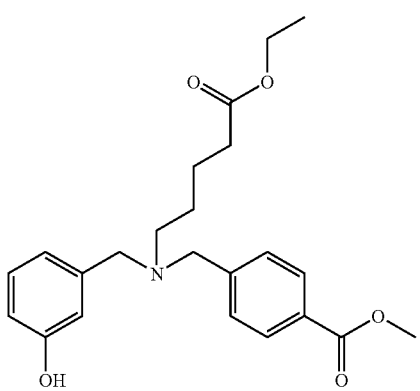

This compound can be obtained analogously to Example I starting from 3-methoxyphenethylamine instead of 2-methoxyphenethylamine.

$^1$H-NMR (200 MHz, d$^6$-DMSO): δ=1.46 (m, 4H), 2.23 (t, 2H), 2.45 (t, 2H), 2.60 (m, 2H), 2.70 (m, 2H), 3.60 (s, 3H), 3.70 (s, 2H), 3.85 (s, 3H), 6.70 (m, 2H), 7.01 (m, 2H), 7.45 (d, 2H), 7.90 (d, 2H), 9.50 (s, 1H).

IV. Methyl 3-{[(5-ethoxy-5-oxopentyl)(2-hydroxyphenethyl)amino]methyl}benzoate

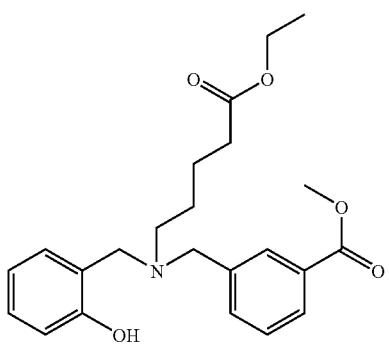

This compound can be obtained analogously to Example I starting from methyl 3-formylbenzoate instead of methyl 4-formylbenzoate.

$^1$H-NMR (200 MHz, d$^6$-DMSO): δ 1.48 (m, 4H), 2.21 (t, 2H), 2.47 (t, 2H), 2.64 (m, 2H), 2.71 (m, 2H), 3.60 (s, 3H), 3.70 (s, 2H), 3.85 (s, 3H), 6.70 (m, 2H), 7.0-7.7 (d, 8H), 9.50 (s, 1H).

Examples V-VIII

Compounds of the Formula II

V.1. Methyl 4-{[(2-hydroxyphenethyl)amino]methyl}benzoate

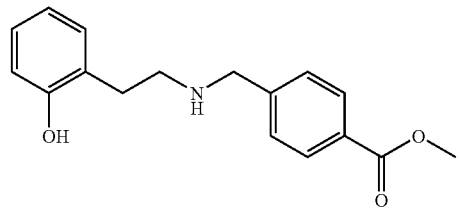

At 0° C., 176.8 ml (176.8 mmol) of a 1N boron tribromide solution in methylene chloride are added dropwise to 16.03 g (53.561 mmol) of methyl 4-{[(2-methoxyphenethyl)amino]methyl}benzoate from Example. I.1 in 100 ml of methylene chloride. After one hour of stirring at 0° C., 150 ml of methanol are added and the solution is heated at reflux for 4 hours. The solvent is distilled off under reduced pressure and the residue is taken up in a mixture of 190 ml of ethyl acetate and 10 ml of methanol. Using 10% strength sodium carbonate solution, the mixture is made alkaline and extracted with ethyl acetate/methanol 9/1. The combined organic phases are washed with saturated sodium chloride solution and dried over magnesium sulphate, and the solvent is distilled off under reduced pressure. The crude product is purified by chromatography over silica gel (0.04-0.063 nm) using the mobile phase methylene chloride/methanol 100/2.

Yield: 6.80 g (42.9% of theory)

$^1$H-NMR (200 MHz, d$^6$-DMSO): δ=2.73 (s, 4H), 3.82 (s, 2H), 3.85 (s, 3H), 6.7 (m, 2H), 7.0 (d, 2H), 7.48 (d, 2H), 7.92 (d, 2H).

V.2. Methyl 4-{[(tert-butoxycarbonyl)(2-hydroxyphenethyl)amino]methyl}-benzoate

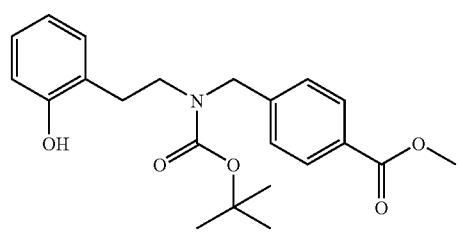

6.80 g (23.82 mmol) of methyl 4-{[(2-methoxyphenethyl)amino]methyl}benzoate from Ex. V.1. are initially charged in 25 ml of methylene chloride and a solution of 5.46 g (25.02 mmol) of tert-butyl pyrocarbonate in 25 ml of methylene chloride is added dropwise at 0° C. After 18 hours of stirring at 22° C., the solvent is distilled off under reduced pressure.

Yield: 9.56 g (99% of theory)

$^1$H-NMR (200 MHz, d$^6$-DMSO): δ=1.32 (s, 9H), 2.70 (t, 2H), 3.35 (m, 2H), 3.83 (s, 3H), 4.42 (s, 2H), 6.6-6.8 (m, 2H), 7.0 (m, 2H), 7.35 (d, 2H), 7.92 (d, 2H).

V.3. Methyl 4[((tert-butoxycarbonyl){2-[(5-phenyl-pentyl)oxy]-phenethyl}amino)-methyl]benzoate

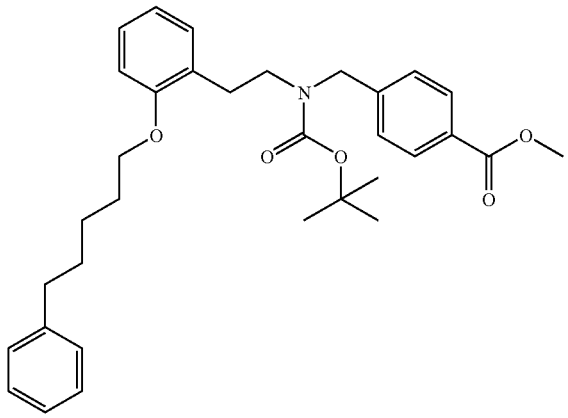

1.78 g (4.63 mmol) of methyl 4-{[(tert-butoxycarbonyl)-(2-hydroxyphenethyl)-amino]methyl}benzoate from Ex. V.2, 1.05 g (4.63 mmol) of 5-phenyl-1-bromopentane and 0.77 g (5.55 mmol) of potassium carbonate in 15 ml of acetonitrile are heated at reflux for 18 hours. The reaction mixture is poured into water, extracted with ethyl acetate and dried over magnesium sulphate and the solvent is distilled off under reduced pressure. A solid is obtained which is reacted further without purification.

Yield: 2.42 g (88.8% of theory)
$^1$H-NMR (200 MHz, d$^6$-DMSO): δ=1.32 (s, 9H), 1.55 (m, 4H), 1.65 (m, 2H), 2.70 (m, 2H), 3.36 (m, 2H), 3.79 (s, 3H), 3.90 (t, 2H), 4.40 (s, 2H) 6.8-6.9 (m, 2H), 7.1-7.3 (m, 9H), 7.94 (d, 2H)

V.4 Methyl 4-[({2-[(5-phenylpentyl)oxy]phenethyl}amino)methyl]benzoate

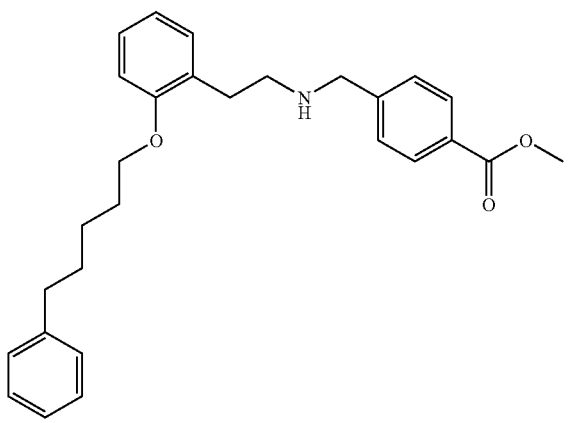

2.42 g (4.54 mmol) of methyl 4-[((tert-butoxycarbonyl){2-[(5-phenylpentyl)oxy]-phenethyl}amino)methyl]benzoate from Ex. V.3 are introduced into a mixture of 4 ml of trifluoroacetic acid and 12 ml of methylene chloride, and the mixture is stirred at 22° C. for 18 hours. The solvent is distilled off completely using a rotary evaporator, the residue is taken up in water and the product is extracted repeatedly with ethyl acetate. The combined organic phases are washed twice with 2N aqueous sodium hydroxide solution, dried over magnesium sulphate and concentrated under reduced pressure.

Yield: 8.25 g (77% of theory)
$^1$H-NMR (200 MHz, d$^6$-DMSO): δ=1.40 (m, 2H), 1.65 (m, 4H), 2.55 (t, 2H), 2.70 (m, 2H), 3.80 (s, 3H), 3.84 (s, 3H), 3.90 (t, 2H), 6.8-6.9 (m, 2H), 7.1-7.3 (m, 7H), 7.45 (d, 2H), 7.90 (d, 2H)

The following compounds were obtained in the same manner:

VI. Methyl 4-({[2-(heptyloxy)phenethyl]amino}methyl)benzoate

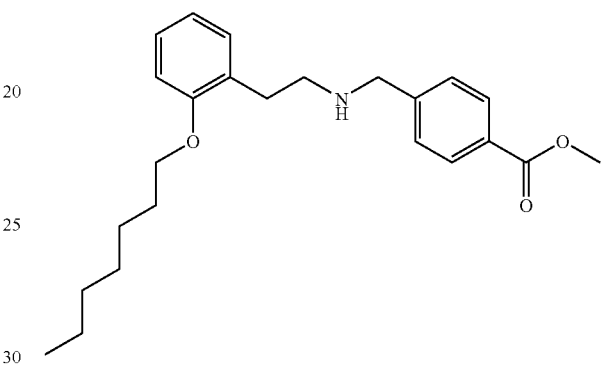

This compound can be obtained analogously to Example V starting from heptyl bromide instead of 5-phenyl-1-bromopentane.

$^1$H-NMR (300 MHz, d$^6$-DMSO): δ=0.85 (t, 3H), 1.2-1.4 (m, 8H), 1.65 (m, 2H), 2.70 (s, 4H), 3.80 (s, 2H), 3.82 (s, 3H), 3.91 (t, 2H), 6.7-6.9 (m, 2H), 7.13 (d, 2H), 7.45 (d, 2H), 7.90 (d, 2H).

VII. Methyl 4-({[2-([1,1'-biphenyl]-4-ylmethoxy)phenethyl]amino}methyl)benzoate

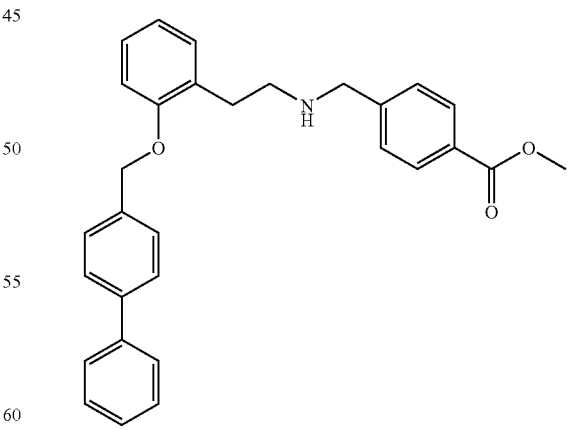

This compound can be obtained analogously to Example V starting from 4-phenylbenzyl bromide instead of 5-phenyl-1-bromopentane.

$^1$H-NMR (200 MHz, d$^6$-DMSO): δ=2.75 (m, 4H), 3.80 (s, 3H), 3.82 (s, 2H), 5.13 (s, 2H), 6.7-7.6 (m, 15H), 7.85 (d, 2H)

VIII. Methyl 4-[({2-[(4-bromobenzyl)oxy]phenethyl}amino)methyl]benzoate

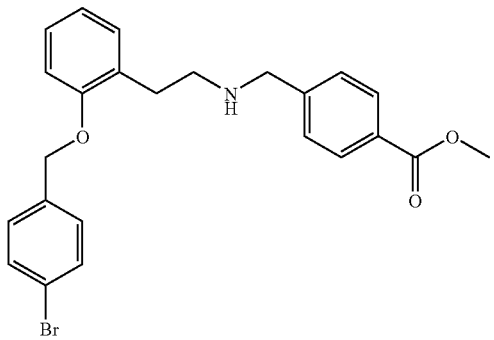

This compound can be obtained analogously to Example V starting from 4-bromobenzyl bromide instead of 5-phenyl-1-bromopentane.

$^1$H-NMR (200 MHz, d$^6$-DMSO): δ 2.75 (m, 4H), 3.80 (s, 3H), 3.82 (s, 2H), 5.13 (s, 2H), 6.7-7.6 (m, 10H), 7.85 (d, 2H)

IX. Methyl 4-([{2-[4-(ethoxycarbonyl)phenoxy]ethyl}(2-hydroxyphenethyl)amino]-methyl Benzoate

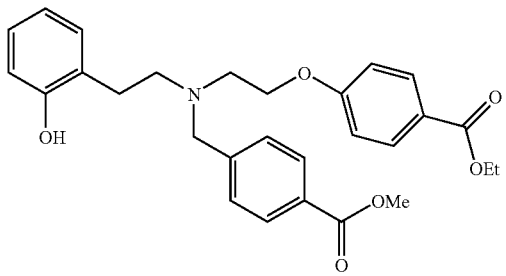

250 mg (0.88 mmol) of methyl 4-{[(2-hydroxyphenethyl)amino]methyl}benzoate from Example V.1., 311 mg (1.14 mmol) of ethyl 4-(2-bromoethoxy)benzoate (Eastman Kodak CO, U.S. Pat. No. 279,082), and 250 mg (2.37 mmol) of sodium carbonate are dissolved in 3 ml of acetonitrile, and the mixture is heated at reflux for 18 hours. After cooling, the solvent is distilled off under reduced pressure and the residue is purified over silica gel (0.04-0.063 nm) using the mobile phase cyclohexane/ethyl acetate 9/1.

Yield: 274 mg (65.5% of theory)

$^1$H-NMR (200 MHz, CDCl$_3$): δ=1.13 (t, 3H), 2.80-3.05 (m, 6H), 3.80-4.35 (m, 9H), 6.70-8.00 (m, 12H), 11.40 (bs, 1H).

X: Methyl 4-({(5-ethoxy-5-oxopentyl)[2-(2-hydroxyphenyl)ethyl]amino}methyl)-benzoate

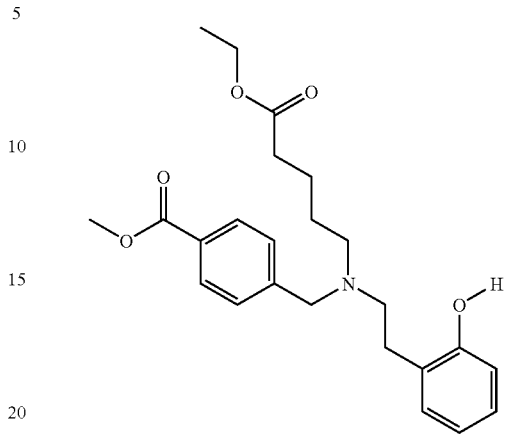

This compound was prepared analogously to Ex. IX, except that the alkylating agent used was ethyl bromovalerate instead of ethyl 4-(2-bromoethoxy)benzoate.

$^1$H-NMR (400 MHz, CDCl$_3$): 1.20 (t, 3H), 1.60 (m, 4H), 2.20 (t, 2H), 2.50 (m, 2H), 2.80 (m, 4H), 3.80 (s, 2H), 3.90 (s, 3H), 4.10 (q, 2H), 6.70 (m, 1H), 6.90 (d, 1H), 6.95 (m, 1H), 7.10 (m, 1H), 7.40 (d, 2H), 8.00 (d, 2H), 12.1 (bs, 1H)

XI: Methyl 2-bromo-4-({(5-ethoxy-5-oxopentyl)[2-(2-hydroxyphenyl)ethyl]amino}methyl)benzoate

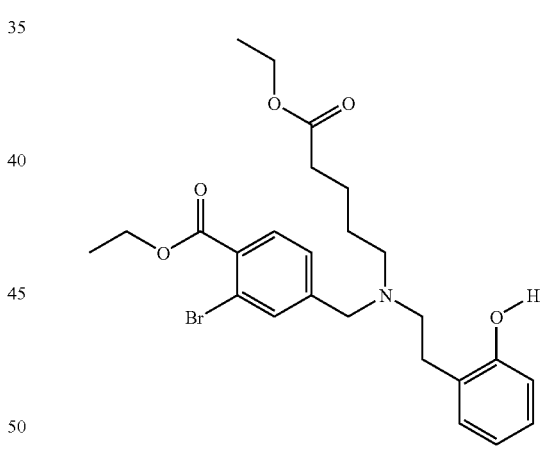

This compound was prepared analogously to Ex. IX, except that the alkylating agent used was ethyl bromovalerate instead of ethyl 4-(2-bromoethoxy)benzoate and that the reaction was carried out using methyl 2-bromo-4-{[(2-hydroxyphenyl)-ethyl]amino}methyl)benzoate (obtained from 2-methoxyphenethylamine and ethyl 3-bromo-4-formylbenzoate analogously to Ex. V.1 [ethyl 3-bromo-4-formylbenzoate can be prepared from diethyl 2-bromoterephthalate by reduction with 1 eq. of lithium aluminium chloride and oxidation of the resulting alcohol with manganese dioxide]).

$^1$H-NMR (200 MHz, CDCl$_3$): 1.20 (t, 3H), 1.40 (t, 3H), 1.60 (m, 4H), 2.20 (t, 2H), 2.50 (m, 2H), 2.80 (m, 4H), 3.80 (s, 2H), 4.10 (q, 2H), 4.40 (q, 2H), 6.70 (m, 1H), 6.90 (m, 2H), 7.10 (m, 1H), 7.40 (m, 1H), 7.60 (m, 1H), 7.70 (m, 1H), 11.70 (bs, 1H).

XII: Methyl 4-({(5-methoxy-5-oxopentyl)[2-(5-fluoro-2-hydroxyphenyl)ethyl]amino}methyl)benzoate

XII. 1. 5-Fluoro-2-methoxybenzaldehyde

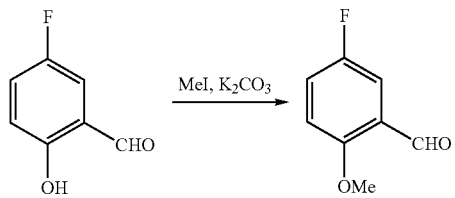

20.0 g (0.143 mol) of 5-fluoro-2-hydroxybenzaldehyde are dissolved in 250 ml of acetonitrile. 81.04 g (0.57 mol) of iodomethane and 39.5 g (285 mol) of potassium carbonate are added, and the suspension is heated at reflux for 3 hours. The suspension is filtered and the mother liquor is diluted with ethyl acetate, washed twice with water, dried over magnesium sulphate and filtered, and the solvents are evaporated under reduced pressure.

Yield: 20.0 g (90.9% of theory)

$^1$H-NMR: (200 MHz, CDCl$_3$): 3.90 (s, 3H), 6.90 (dd, J=10 Hz, J=5 Hz, 1H), 7.25 (m, 1H), 7.50 (dd, J=10 Hz, J=4 Hz, 1H), 10.40 (d, J=4 Hz, 1H)

XII.2. (5-Fluoro-2-methoxyphenyl)methanol

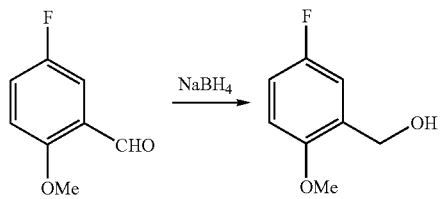

20.0 g (0.13 mol) of 5-fluoro-2-methoxybenzaldehyde are dissolved in 205 ml of methanol. Under argon, 2.45 g (54.9 mol) of sodium borohydride are added in small portions. The solution is stirred at RT for 4 hours. The solution is concentrated and the residue is taken up in water and stirred for 30 min. The aqueous phase is extracted with ethyl acetate and the organic phase is dried over magnesium sulphate, filtered and evaporated under reduced pressure.

Yield: 19.0 g (93.8% of theory)

$^1$H-NMR: (300 MHz, CDCl$_3$): 3.80 (s, 3H), 4.60 (d, J=7 Hz, 2H), 6.80 (dd, J=14 Hz, J=6 Hz, 1H), 6.95 (m, 1H), 7.05 (dd, J=6 Hz, J=4 Hz, 1H)

XII.3. 2-(Chloromethyl)-4-fluoro-1-methoxybenzene

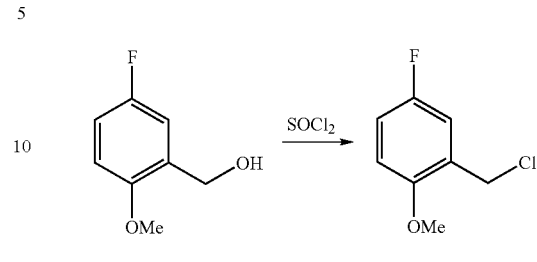

19.0 g (0.12 mol) of (5-fluoro-2-methoxyphenyl)methanol are dissolved in 105 ml of dichloromethane. One drop of DMF is added, and 26.6 ml (0.37 mol) of thionyl chloride are then added slowly. The solution is stirred at RT for 2 hours and evaporated under reduced pressure. The residue is taken up in ethyl acetate, the mixture is cooled and admixed with water and then washed with saturated sodium bicarbonate solution and water, dried over magnesium sulphate and evaporated under reduced pressure.

Yield: 18.0 g (84.5% of theory)

$^1$H-NMR: (200 MHz, CDCl$_3$): 3.85 (s, 3H), 4.60 (s, 2H), 6.80 (dd, J=14 Hz, J=6 Hz, 1H), 7.00 (m, 1H), 7.10 (dd, J=6 Hz, J=4 Hz, 1H)

XII.4. (5-Fluoro-2-methoxyphenyl)acetonitrile

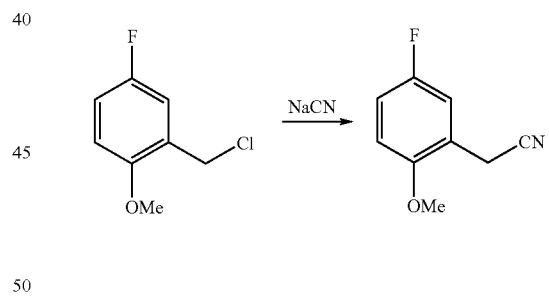

18.0 g (0.103 mol) of 2-(chloromethyl)-4-fluoro-1-methoxybenzene are dissolved in DMF:water (5:1) and 30.3 g (0.62 mol) of sodium cyanide and a spatula tip of potassium iodide are added. The solution is stirred overnight at 120° C. The solution is then cooled to RT, water is added, the solution is extracted with ethyl acetate and the extract is dried over magnesium sulphate, filtered and evaporated under reduced pressure. The residue is chromatographed over silica gel using the mobile phase cyclohexane:ethyl acetate (7:3).

Yield: 14.5 g (85.2% of theory)

$^1$H-NMR: (200 MHz, CDCl$_3$): 3.70 (s, 2H), 3.85 (s, 3H), 6.80 (dd, J=14 Hz, J=6 Hz, 1H), 7.00 (m, 1H), 7.10 (dd, J=6 Hz, J=4 Hz, 1H)

XII. 5. 2-(5-Fluoro-2-methoxyphenyl)ethylamine

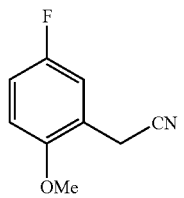 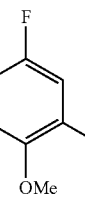

Under argon, 17.6 g (132 mmol) of aluminium trichloride are dissolved in THF, and the mixture is cooled to 0° C. 87 ml of lithium aluminium hydride solution (1M in THF) are slowly added dropwise. A solution of 14.5 g (87.8 mmol) of (5-fluoro-2-methoxyphenyl)acetonitrile in 100 ml is added slowly. The reaction mixture is stirred at RT for 2 hours. At 0° C., ice/water is then added, the mixture is made alkaline using sodium hydroxide solution and extracted with ethyl acetate and the extract is dried and concentrated using a rotary evaporator.

Yield: 10.2 g (68.7% of theory)

$^1$H-NMR: (200 MHz, CDCl$_3$): 1.30 (bs, 2H), 2.70 (t, J=6 Hz, 2H), 2.90 (t, J=6 Hz, 2H), 3.80 (s, 3H), 6.70-6.90 (m, 3H)

XII.6. Methyl 4-({[2-(5-fluoro-2-methoxyphenyl)ethyl]imino}methyl)benzoate

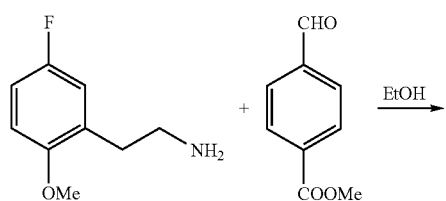

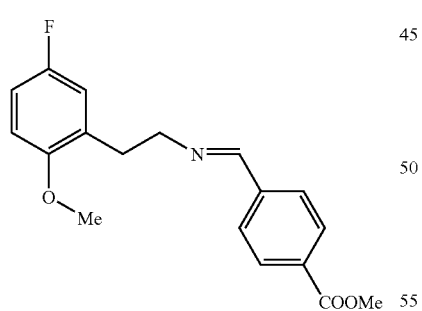

9.00 g (53 mmol) of 2-(5-fluoro-2-methoxyphenyl)ethylamine and 8.73 g (53 mmol) of methyl 4-formylbenzoate are dissolved in 450 ml of ethanol, the mixture is heated at reflux for 2 hours and the solvents are then evaporated under reduced pressure.

Yield: 17.0 g (100% of theory)

$^1$H-NMR: (300 MHz, CDCl$_3$): 3.00 (t, J=6 Hz, 2H), 3.80 (s, 3H), 3.85 (t, 2H), 3.90 (s, 3H), 6.70-6.90 (m, 3H), 7.75 (d, 2H), 8.10 (d, 2H), 8.20 (s, 1H)

XII.7. Methyl 4-({[2-(5-fluoro-2-methoxyphenyl)ethyl]amino}methyl)benzoate

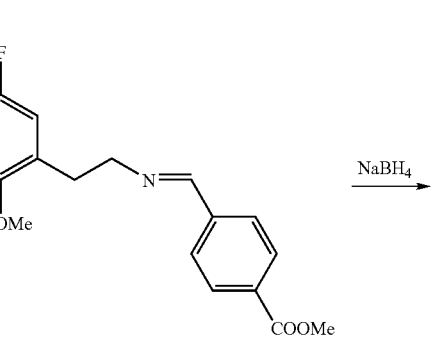

5.30 g (16.8 mmol) of methyl 4-({[2-(5-fluoro-2-methoxyphenyl)ethyl]imino}-methyl)benzoate are dissolved in 48.4 ml of methanol, and 1.27 g (33.6 mmol) of sodium borohydride are added. The solution is stirred at RT for 2 hours, and water is then added and the solution is extracted with ethyl acetate. The organic phase is dried over magnesium sulphate, filtered and concentrated under reduced pressure. The residue is taken up in ethyl acetate and extracted with diluted HCl. The aqueous phase is made alkaline and extracted with ethyl acetate, and the extract is dried over magnesium sulphate, filtered and concentrated under reduced pressure.

Yield: 4.79 g (89.8% of theory)

$^1$H-NMR: (200 MHz, CDCl$_3$): 3.00 (bs, 4H), 3.70 (s, 3H), 3.85 (s, 3H), 4.10 (bs, 2H), 6.70 (m, 1H), 6.90 (m, 2H), 7.70 (d, 2H), 8.00 (d, 2H), 10.20 (bs, 1H)

XII.8. Methyl 4-({(5-ethoxy-5-oxopentyl)[2-(5-fluoro-2-methoxyphenyl)ethyl]-amino}methyl)benzoate

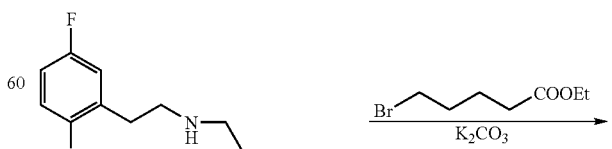 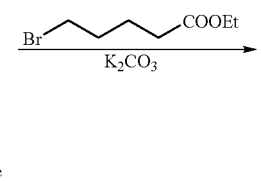

-continued

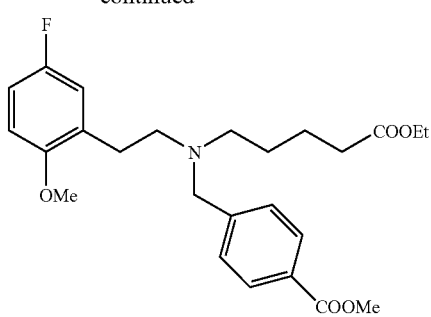

Under argon, 4.70 g (14.8 mmol) of methyl 4-({[2-(5-fluoro-2-methoxyphenyl)-ethyl]amino}methyl)benzoate are dissolved in 25 ml of acetonitrile. 3.25 g (15.6 mmol) of ethyl bromovalerate, 7.24 g (22.2 mmol) of caesium carbonate and a spatula tip of potassium iodide are added, and the suspension is heated at reflux overnight. The solid is filtered off, the solution is concentrated and the residue is chromatographed over silica gel (cyclohexane:ethyl acetate (4:1)).

Yield: 3.8 g (576% of theory)

$^1$H-NMR (300 MHz, CDCl$_3$): 1.20 (t, 3H), 1.50 (m, 4H), 2.30 (t, 2H), 2.50 (t, 2H), 2.60-2.80 (m, 4H), 3.65 (s, 2H), 3.70 (s, 3H), 3.90 (s, 3H), 4.10 (q, 2H), 6.70 (m, 1H), 6.80 (m, 2H), 7.35 (d, 2H), 7.90 (d, 2H)

XII: Methyl 4-({(5-methoxy-5-oxopentyl) [2-(5-fluoro-2-hydroxyphenyl)-ethyl]amino}methyl)benzoate

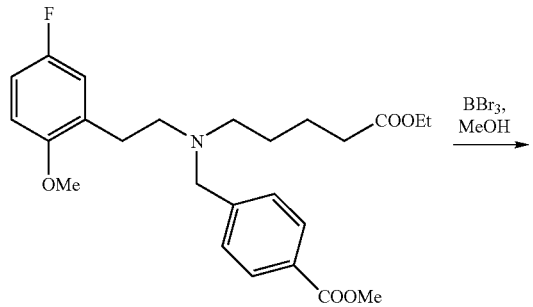

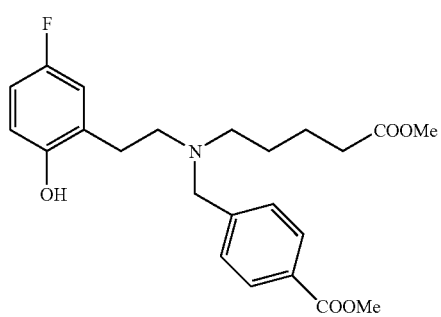

2.6 g (5.84 µmmol) of methyl 4-({(5-ethoxy-5-oxopentyl) [2-(5-fluoro-2-methoxy-phenyl)ethyl]amino}methyl)benzoate are dissolved in 50 ml of dichloromethane, the mixture is cooled to 0° C., and 19.3 ml (19.3 mmol) of a 1N solution of boron tribromide in dichloromethane are added dropwise. The solution is stirred at 0° C. for one hour. 50 ml of methanol are slowly added dropwise at 0° C., and the reaction mixture is heated at reflux overnight. The mixture is cooled and the solvents are evaporated under reduced pressure. The residue is taken up in ethyl acetate and washed with sodium carbonate, the aqueous phase is extracted three times with ethyl acetate and the combined organic phases are washed with saturated sodium chloride solution, dried over magnesium sulphate, filtered and concentrated. The residue is chromatographed over silica gel (cyclohexane:ethyl acetate (5:1) to ethyl acetate:methanol (9:1)).

Yield: 840 mg (34.5% of theory)

$^1$H-NMR (200 MHz, CDCl$_3$): 1.60 (m, 4H), 2.20 (m, 2H), 2.50 (m, 2H), 2.80 (m, 4H), 3.60 (s, 3H), 3.80 (s, 2H), 3.90 (s, 3H), 6.65 (m, 1H), 6.80 (m, 2H), 7.40 (d, 2H), 7.90 (d, 2H), 11.90 (bs, 1H)

XIII: Tert-butyl 4-({[2-(2-{[4-(2-phenylethyl)benzyl]oxy}phenyl)ethyl]amino}-methyl)benzoate

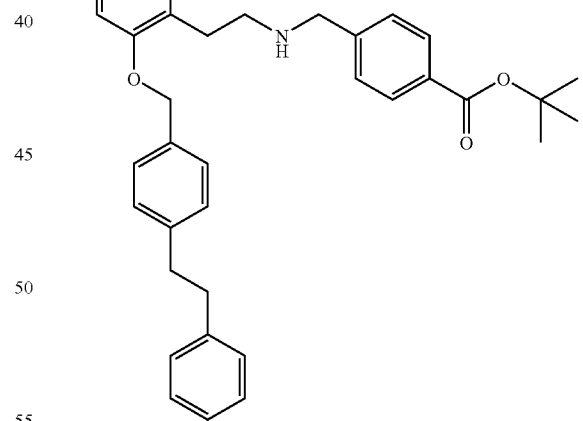

This compound was prepared analogously to Ex. 1.1 from 2-(2-{[4-(2-phenylethyl)-benzyl]oxy}phenyl)ethylamine and tert-butyl 4-formylbenzoate.

$^1$H-NMR (400 MHz, DMSO): 1.50 (s, 9H), 2.60 (m, 4H), 2.80 (m, 4H), 3.80 (s, 2H), 5.00 (s, 2H), 6.80 (m, 1H), 6.90 (d, 1H), 7.10-7.40 (m, 13H), 7.80 (d, 2H)

XIV: 4'-(Trifluoromethyl)-1,1'-biphenyl-4-carbaldehyde

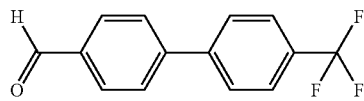

1 g (4.45 mmol) of 1-bromo-4-(trifluoromethyl)benzene and 0.73 g (4.9 mmol) of 4-formylbenzoic acid are added to 30 ml of dimethoxyethane and mixed with 15 ml of 1M sodium carbonate solution. 110 mg of tetrakis (triphenylphosphine)palladium(II) are added, and the mixture is then heated at reflux temperature for 18 hours. The reaction solution is cooled, dichloromethane and water are added, the mixture is filtered through Extrelut and the solvent is distilled off under reduced pressure.

Yield: 87%

$^1$H-NMR (400 MHz, CDCl$_3$): 7.70 (m, 6H), 8.00 (d, 2H), 10.00 (s, 1H).

XV: [4'-(Trifluoromethyl)-1,1'-biphenyl-4-yl]methanol

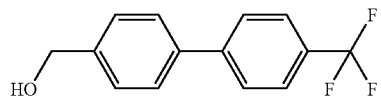

970 mg (3.88 mmol) of the aldehyde XIV are dissolved in methanol and 150 mg (3.88 mmol) of sodium hydride are added, the mixture is stirred at room temperature for 2 hours and concentrated, and water is added. The mixture is stirred for 30 min and the solid is filtered off.

Yield: 90%

$^1$H-NMR (400 MHz, CDCl$_3$): 1.75 (t, 1H), 4.80 (d, 2H), 7.40-7.90 (m, 8H).

XVI: 4-(Chloromethyl)-4'-(trifluoromethyl)-1,1'-biphenyl

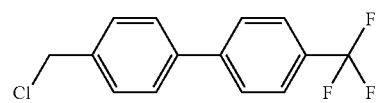

883 mg (3.49 mmol) of the alcohol XV are dissolved in dichloromethane, 2.5 ml (35 mmol) of POCl$_3$ are added and the solution is stirred at room temperature for 2 hours. The solution is washed with water, dried and concentrated.

Yield: 85%

XVIIa: [2-(1,1'-Biphenyl-4-ylmethoxy)phenyl]methanol

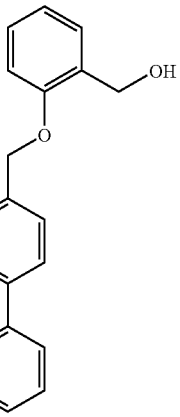

A mixture of 2.92 g (23.49 mmol) of 2-hydroxybenzyl alcohol, 5.00 g (24.67 mmol) of 4-phenylbenzyl chloride and 3.41 g (24.67 mmol) of potassium carbonate in 60 ml of acetone was heated at reflux overnight. The precipitate formed was filtered off. The residue was taken up in 1N NaOH, and the mixture was extracted with ethyl acetate. The combined organic phases were dried over Na$_2$SO$_4$ and the solvent was removed. The product was purified chromatographically (silica gel, cyclohexane/ethyl acetate 10:1).

Yield: 4.27 g (62.7%)

$^1$H NMR (300 MHz, CDCl$_3$): δ=2.26 (t, J=5.7 Hz, 1H), 4.75 (d, J=5.7 Hz, 2H), 5.16 (s, 2H), 6.88-7.02 (m, 2H), 7.18-7.66 (m, 11H).

The following compounds were prepared analogously:

| Example | Structure | Yield (%) | Physical data: $^1$H-NMR (δ in ppm, selection) or LC/MS (mass/retention time [min]) |
|---|---|---|---|
| XVIIb, (from 5-bromo-pentyl-benzene) | 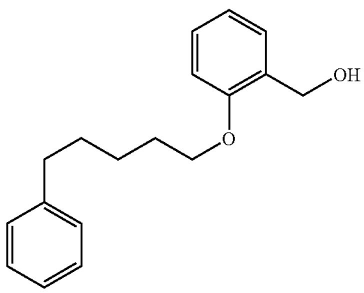 | 86.4 | $^1$H NMR (300 MHz, CDCl$_3$): δ = 1.43-1.58 (m, 2H), 1.62-1.77 (m, 2H), 1.77-1.93 (m, 2H), 2.28 (bs, 1H), 2.64 (t, J = 7.7 Hz, 2H), 4.00 (t, J = 6.4 Hz, 2H), 4.66 (s, 2H), 6.80-6.97 (m, 2H), 7.10-7.34 (m, 7H). |
| XVIIc (from 4-cyclo-hexyl-benzyl-chloride) | 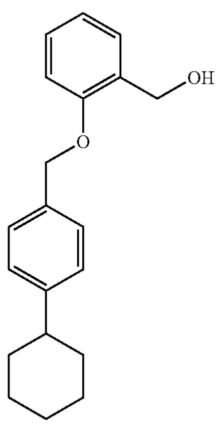 | 90.2 | $^1$H NMR (300 MHz, CDCl$_3$): δ = 1.14-2.59 (m, 12H), 4.71 (s, 2H), 5.07 (s, 2H), 6.80-7.39 (m, 8H). |
| XVIId (from 4-phenyl-ethyl-benzyl chloride) | 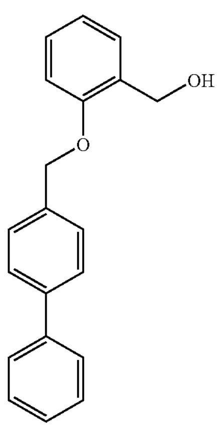 | 56.2 | $^1$H NMR (400 MHz, CDCl$_3$): δ = 2.30 (t, J = 6.1 Hz, 1H), 2.93 (s, 4H), 4.72 (d, J = 6.1 Hz, 2H), 5.08 (s, 2H), 6.91-6.99 (m, 2H), 7.14-7.35 (m, 11H). |

XVIIIa: [2-(1,1'-Biphenyl-4-ylmethoxy)phenyl]acetonitrile

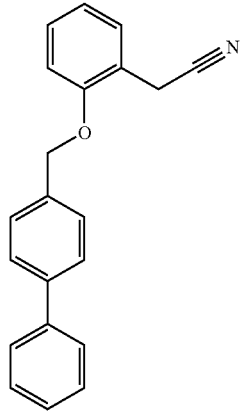

A solution of 15.20 g (52.35 mmol) of XVIIa in 300 ml of benzene was added dropwise to a solution of 6.49 ml (88.99 mmol) of thionyl chloride in 150 ml of benzene. The solution was heated at reflux for 2 h. The solvent was removed and the residue was taken up in 350 ml of DMF. 25.65 g (523.48 mmol) of NaCN were added, and the mixture was heated at reflux for 16 h. After the mixture had cooled to room temperature, it was admixed with water and the precipitate was filtered off with suction.

Yield: 13.6 g (81.5%)

$^1$H-NMR (400 MHz, CDCl$_3$): δ 3.74 (s, 2H), 5.16 (s, 2H), 6.93-7.03 (m, 2H), 7.21-7.67 (m, 11H).

The following compounds were prepared analogously:

| Example | Structure | Yield (%) | Physical data: $^1$H-NMR (δ in ppm, selection) or LC/MS (mass/retention time [min]) |
|---|---|---|---|
| XVIIIb (from XVIIc) | 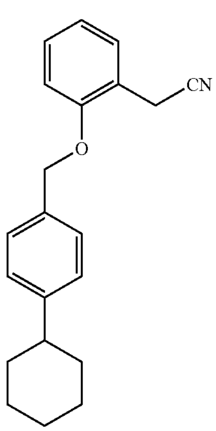 | 47.1 | $^1$H NMR (400 MHz, CDCl$_3$): δ = 1.17-1.95 (m, 10H), 2.43-2.60 (m, 1H), 3.72 (s, 2H), 5.07 (s, 2H), 6.89-7.02 (m, 2H), 7.18-7.41 (m, 6H). |
| XVIIIc (from XVIId) | | 75.0 | $^1$H NMR (400 MHz, CDCl$_3$): δ = 2.93 (s, 4H), 3.71 (s, 2H), 5.08 (s, 2H), 6.89-7.03 (m, 2H), 7.12-7.43 (m, 11H). |

XIXa: 2-[2-(1,1'-Biphenyl-4-ylmethoxy)phenyl]ethanamine Hydrochloride

A solution of 7.90 g (26.39 mmol) of XVIIIa in 80 ml of THF was added dropwise to a solution of 52.93 ml (52.93 mmol) of BH$_3$.THF (1 M in THF). The solution was heated at reflux for 2 h. After the solution had cooled to room temperature, it was mixed very carefully with 150 ml of 6 M hydrochloric acid, and the mixture was stirred at room temperature for 16 h. The precipitate that had formed was filtered off and dried under high vacuum.

Yield: 6.72 g (74.9%)

$^1$H NMR (400 MHz, DMSO-d$_6$): δ=2.89-3.01 (m, 4H), 5.20 (s, 2H), 6.85-7.78 (m, 13H), 7.99 (bs, 3H).

The following compounds were prepared analogously:

| Example | Structure | Yield (%) | Physical data: ¹H-NMR (δ in ppm, selection) or LC/MS (mass/retention time [min]) |
|---|---|---|---|
| XIXb (from XVIIIb) | 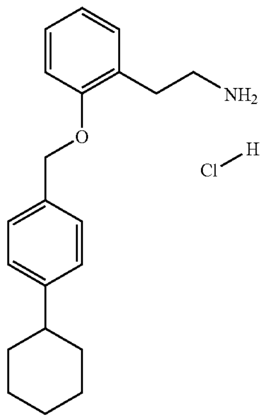 | 70.3 | ¹H NMR (400 MHz, DMSO-d$_6$): δ = 1.09-1.46 (m, 6H), 1.57-1.85 (m, 5H), 2.75-2.95 (m, 2H), 2.96-3.05 (m, 2H), 5.09 (s, 2H), 6.77-7.44 (m, 8H), 7.77 (bs, 3H). |
| XIXc (from XVIIIc) | 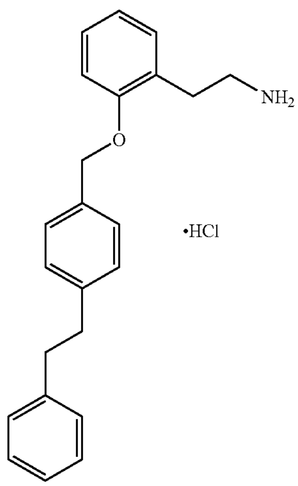 | 83.1 | ¹H NMR (300 MHz, DMSO-d$_6$): δ = 2.69-3.06 (m, 8H), 5.10 (s, 2H), 6.83-7.42 (m, 13H), 7.95 (bs, 3H). |

XXa: tert-Butyl 5-({2-[2-(1,1'-biphenyl-4-yl-methoxy)phenyl]-ethyl}amino)pentanoate

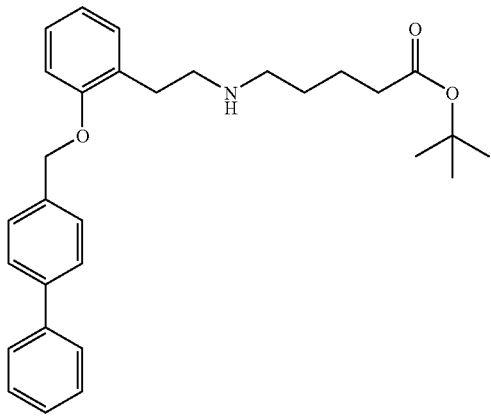

13.40 g (132.40 mmol) of triethylamine and 1.05 g (4.41 mmol) of tert-butyl bromovalerate were added to a solution of 3.00 g (8.83 mmol) of XVIIIa in 50 ml of DMF. The mixture was stirred at room temperature for 16 h, and the reaction was monitored by thin-layer chromatography. The solution was admixed with water and extracted with ethyl acetate/cyclohexane 1:1. The combined organic phases were dried over Na$_2$SO$_4$ and the solvent was removed. The product was purified chromatographically (silica gel, CH$_2$Cl$_2$/MeOH 20:1).

Yield: 0.85 g (41.9%).

¹H-NMR (300 MHz, DMSO-d$_6$): δ=1.31-1.54 (m, 4H), 1.36 (s, 9H), 2.15 (t, J=7.2 Hz, 2H), 2.56 (t, J=6.8 Hz, 2H), 2.70-2.91 (m, 5H), 5.17 (s, 2H), 6.82-7.75 (m, 13H).

The following compounds were prepared analogously:

| Example | Structure | Yield (%) | Physical data: $^1$H-NMR (δ in ppm, selection) or LC/MS (mass/retention time [min]) |
|---|---|---|---|
| XXb (from XIXb) | 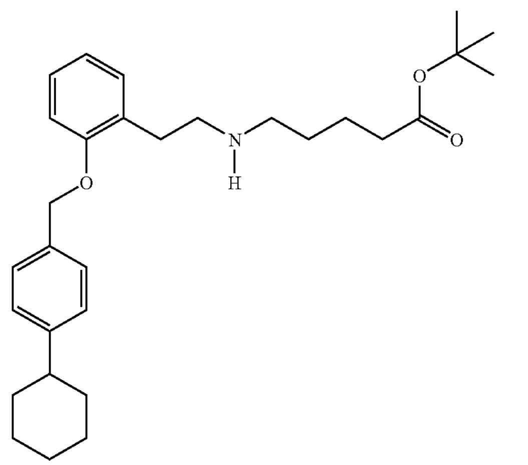 | 68.5 | $^1$H NMR (400 MHz, CDCl$_3$): δ = 1.16-1.95 (m, 21H), 2.19 (t, J 0 7.3 Hz, 2H), 2.43-2.66 (m, 4H), 2.76-3.00 (m, 6H), 5.03 (s, 2H), 6.82-7.42 (m, 8H). |
| XXc (from XIXc) | 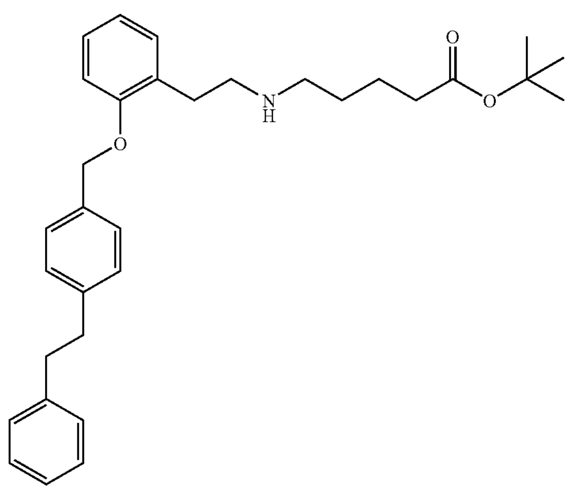 | 90.4 | LC/MS: 4.04 min [488 (M + H)]. |

XXI: Methyl 4-{[{2-[2-({4-[2-(4-{[tert-butyl(dimethyl)silyl]oxy}phenyl)-ethyl]benzyl}oxy)phenyl]ethyl}(5-ethoxy-5-oxopentyl)amino]methyl}benzoate

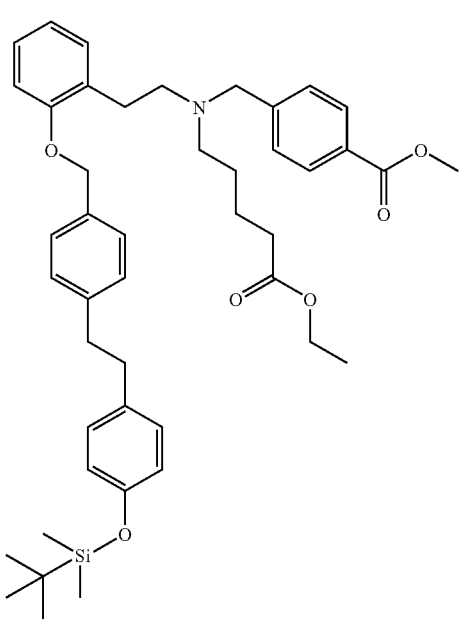

166 mg (0.403 mmol) of methyl 4-({(5-ethoxy-5-oxopentyl)-[2-(2-hydroxyphenyl)ethyl]amino}methyl)benzoate and 160 mg (0.443 mmol) of tert-butyl(4-{2-[4-(chloromethyl)phenyl]ethyl}phenoxy)dimethylsilane (prepared from 4-{[tert-butyl(dimethyl)silyl]oxy}benzaldehyde and [4-(methoxycarbonyl)-benzyl](triphenyl)phosphonium chloride via a Wittig reaction, subsequent hydrogenation of the double bond, reduction with lithium aluminium hydride and chlorination analogously to XVI) are dissolved in 6 ml of acetonitrile. 263 mg (0.81 mmol) of caesium carbonate and a spatula tip of potassium iodide are added, and the mixture is heated at reflux overnight. The suspension is filtered and concentrated and the residue is chromatographed over silica gel (cyclohexane:ethyl acetate=5:1).

Yield: 27 mg (9.1% of theory)

LC/MS: 738 (M+1), Rt=3.76

Conditions: column: Symmetry C18 2.1*150 mm; mobile phase: acetonitrile+0.6 g of 30% strength HCl/1 l of H$_2$O; gradient: 10% acetonitrile to 90% acetonitrile; flow rate: 0.6 ml/min; detector: UV 210 nm

SYNTHESIS EXAMPLES

Example 1

Methyl 4-{[{2-[(2-chlorobenzyl)oxy]phenethlyl}(5-methoxy-5-oxopentyl)-amino]methyl}benzoate (by Process D)

193.2 mg (0.484 mmol) of methyl 4-{[(2-hydroxyphenethyl)amino]methyl}benzoate from Ex. I, 77.9 mg (0.484 mmol) of 2-chlorobenzyl chloride and 80.2 mg (0.580 mmol) of potassium carbonate in 2.0 ml of acetonitrile are heated at reflux for 18 hours. The batch is poured into water and extracted with ethyl acetate. After drying over magnesium sulphate and distillative removal of the solvent under reduced pressure the crude product is purified by flash chromatography over silica gel (0.04-0.063 nm) using cyclohexane/ethyl acetate 2/1 as mobile phase.

Yield: 245.2 mg (83.5% of theory)

$^1$H-NMR (200 MHz, d$^6$-DMSO): δ=1.40 (m, 4H), 2.15 (t, 2H), 2.40 (dd, 2H), 2.57 (m, 2H), 2.72 (m, 2H), 3.53 (s, 3H), 3.82 (s, 3H), 5.08 (s, 2H), 6.9-7.5 (m, 10H), 7.82 (d, 2H).

Example 2

4-[((4-carboxybutyl){2-[(2-chlorobenzyl)oxy]phenethyl}amino)methyl]-benzoic Acid (by Process E)

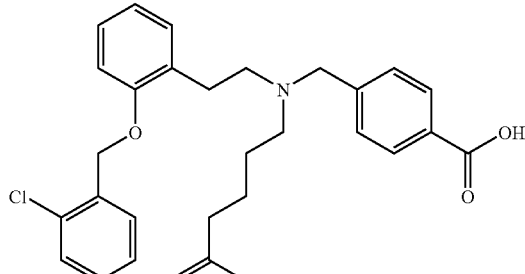

124.8 mg (0.238 mmol) of methyl 4-{[{2-[(2-chlorobenzyl)-oxy]phenethyl}(5-methoxy-5-oxopentyl)amino]methyl}benzoate from Ex. 1 are initially charged in 0.3 ml of methanol and 0.17 ml of water and admixed with 0.2 ml of a 40% strength sodium hydroxide solution. The mixture is stirred at 60° C. for one hour and then cooled, and the methanol is distilled off under reduced pressure. The aqueous phase is adjusted to pH 4 by addition of a citric acid/aqueous sodium hydroxide solution buffer and the resulting precipitate is separated off. Tituration with boiling cyclohexane gives a finely crystalline product.

Yield: 65.70 mg (54.4% of theory)

$^1$H NMR (200 MHz, $d^6$-DMSO): δ 1.35 (br. m 4H), 1.98 (br. m, 2H), 2.37 (m 2H), 2.58 (m, 2H), 2.70 (m, 2H), 5.12 (s, 2H), 6.8-7.6 (m, 10H), 7.75 (d, 2H), 13.5 (br. s, 1H).

Example 3

Methyl 4-[((5-ethoxy-3,3-dimethyl-2,5-dioxopentyl){2-[(5-phenylpent-yl)oxy]phenethyl}amino)methyl]benzoate (by Process A)

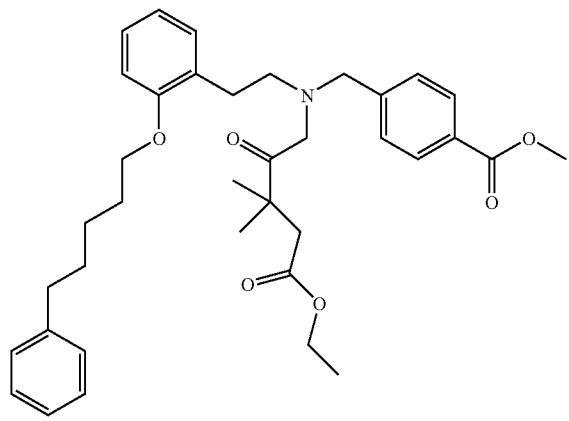

200.0 mg (0.463 mmol) of methyl 4-[({2-[(5-phenylpentyl)oxy]phenethyl}amino)-methyl]benzoate from Ex. V, 116.4 mg (0.463 mmol) of ethyl 5-bromo-3,3-dimethyllaevulinate and 58.9 mg (0.56 mmol) of sodium carbonate in 1 ml of acetonitrile are heated at 60° C. for 18 hours. The solvent is distilled off using a rotary evaporator and the residue is poured into water and extracted with ethyl acetate. The organic phase is washed with saturated sodium chloride solution, dried over magnesium sulphate and concentrated. The crude product is purified by chromatography over silica gel (0.04-0.063 nm) using cyclohexane/ethyl acetate 10/1.

Yield: 163.1 mg (58.5% of theory)

$^1$H-NMR (200 MHz, $d^6$-DMSO): δ=1.09 (s, 6H), 1.10 (t, 3H), 1.35 (m, 2H), 1.60 (m, 4H), 2.55 (m, 2H), 2.70 (s, 2H), 3.75 (s, 3H), 3.96 (q, 2H), 6.7-6.9 (m, 2H), 7.0-7.3 (m, 7H), 7.40 (d, 2H), 7.85 (d, 2H).

Example 4

Methyl 4-{[{2-[(4-bromobenzyl)oxy]phenethyl}(5-ethoxy-5-oxopentyl) amino]methyl}benzoate (by Process D)

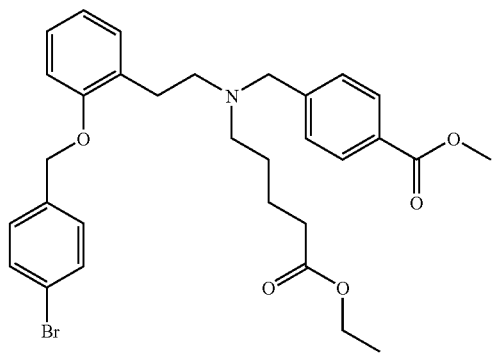

5.00 g (11.0 mmol) of methyl 4-[({2-[(4-bromobenzyl)oxy]phenethyl}amino)-methyl]benzoate from Ex. VIII, 2.30 g (11.0 mmol) of ethyl 5-bromovalerate and 1.109 g (13.21 mmol) of sodium bicarbonate in 30 ml of acetonitrile are heated at reflux for 18 hours. The reaction mixture is admixed with water and extracted with methylene chloride. The organic phase is washed with saturated sodium chloride solution and dried over magnesium sulphate and the solvent is distilled off under reduced pressure. The residue is purified by chromatography over silica gel using the mobile phase methylene chloride/methanol 100/1.

Yield: 5.69 g (88.1% of theory)

$^1$H-NMR (200 MHz, $d^6$-DMSO): δ=1.1 (m, 2H), 1.4 (m, 2H), 2.15 (t, 3H), 2.4 (t, 2H), 2.6 (m, 2H), 2.8 (m, 2H), 3.63 (s, 2H), 3.80 (s, 2H), 4.0 (q, 2H), 5.10 (s, 2H), 6.85 (t, 2H), 7.0-7.2 (m, 8H), 7.4-7.8 (m), 7.9 (d, 2H)

Example 5

Methyl 4-{[{2-[(4'-chloro[1,1'-biphenyl]-4-yl)methoxy]phenethyl}(5-ethoxy-5-oxopentyl)amino]methyl}benzoate (by Process F)

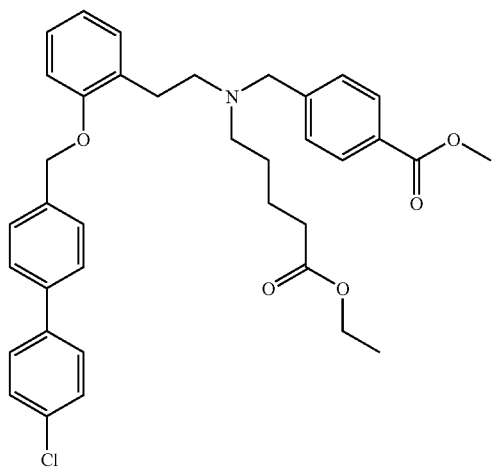

300.0 mg (0.51 mmol) of methyl 4-{[{2-[(4-bromobenzyl)oxy]phenethyl}(5-ethoxy-5-oxopentyl)amino]methyl}benzoate from Ex. 4 are initially charged in 3 ml of dimethoxyethane and admixed successively with 101.7 mg (0.62 mmol) of 4-chlorophenylboronic acid and 0.57 ml of 2M sodium carbonate solution. 10.0 mg of dichlorobis(triphenylphosphine)palladium(II) are added, and the mixture is then heated at reflux temperature for 18 hours. The reaction solution is cooled, admixed with 20 ml of ethyl acetate and washed successively with 5% strength sodium hydrogen phosphate solution, water and saturated sodium chloride solution. The organic phase is dried over magnesium sulphate and the solvent is distilled off under reduced pressure. The crude product is chromatographed over silica gel using the mobile phase cyclohexane/ethyl acetate=10:1.

Yield: 240.5 mg (74.3% of theory)

$^1$H-NMR (200 MHz, d$^6$-DMSO): δ=1.10 (t, 3H), 1.43 (m, 4H), 2.15 (t, 2H), 2.45 (t, 2H), 2.62 (m, 2H), 2.75 (m, 2H), 3.63 (s, 2H), 3.80 (s, 3H), 3.97 (q, 2H), 5.09 (s, 2H), 6.85 (t, 1H), 7.01 (d, 1H), 7.13 (dd, 2H), 7.36 (d, 2H), 7.5-7.7 (m, 8H), 7.83 (d, 2H).

Example 6

Methyl 4-({(5-methoxy-5-oxopentyl)[2-({4-[(E)-2-phenylethenyl]benzyl}-oxy)phenethyl]amino}methyl)benzoate (by Process D)

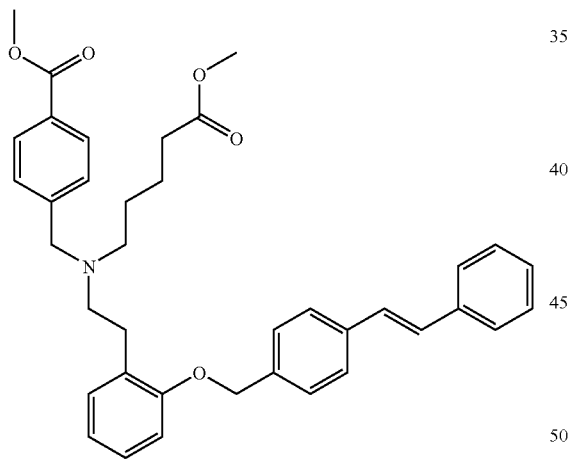

1.0 g (2.50 mmol) of methyl 4-{[(2-hydroxyphenethyl)-(5-methoxy-5-oxopentyl)-amino]methyl}benzoate from Ex. I, 0.687 g (3.00 mmol) of 4-(chloromethyl)stilbene and 0.520 g (3.75 mmol) of potassium carbonate in 10.0 ml of acetonitrile are heated at reflux for 18 hours. The solution is filtered and the solvent is distilled off under reduced pressure. The crude product is purified by chromatography over silica gel using the mobile phase cyclohexane/ethyl acetate 4/1.

Yield: 1.32 g (79.9% of theory)

$^1$H-NMR (300 MHz, d$^6$-DMSO): δ=1.4-1.6 (m, 4H), 2.17 (t, 2H), 2.43 (t, 2H), 2.6 (m, 2H), 2.75 (m, 2H, 3.55 (s, 3H), 3.64 (s, 2H), 3.70 (s, 3H), 5.05 (s, 2H), 6.7-7.4 (m, 11H), 7.55 (t, 4H), 7.85 (d, 2H).

Example 7

Methyl 4-[((5-methoxy-5-oxopentyl){2-[(4-phenethylbenzyl)oxy]-phenethyl}amino)methyl]benzoate (by Process G)

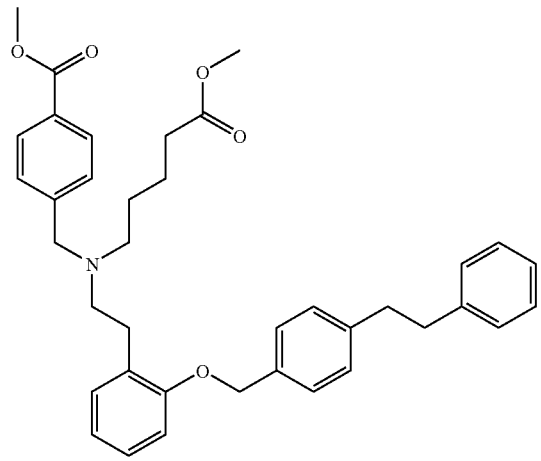

781.8 mg (1.34 mmol) of methyl 4-({(5-methoxy-5-oxopentyl)[2-({4-[(E)-2-phenyl-ethenyl]benzyl}oxy)phenethyl]amino}methyl)benzoate from Ex. 6 and 80.0 mg of 10% palladium on activated carbon in 10 ml of ethyl acetate are hydrogenated under atmospheric pressure. After 1 hour, the calculated amount of hydrogen has been taken up. The solution is filtered and the solvent distilled off under reduced pressure. The crude product is purified by chromatography over silica gel using the mobile phase cyclohexane/ethyl acetate=10:1.

Yield: 309 mg (38.9% of theory)

$^1$H-NMR (300 MHz, d$^6$-DMSO): δ=1.42 (m, 4H), 2.15 (t, 2H), 2.41 (t, 2H), 2.57 (m, 2H), 2.72 (m, 2H), 2.85 (s, 4H), 3.55 (s, 3H), 3.60 (s, 2H), 3.82 (s, 2H), 4.98 (s, 2H), 6.8-7.4 (m, 15H), 7.85 (d, 2H).

Example 8

4-[((4-Carboxybutyl)-{2-[(4-phenethylbenzyl)oxy]phenethyl}amino)-methyl]benzoic Acid Hydrochloride (by Process E)

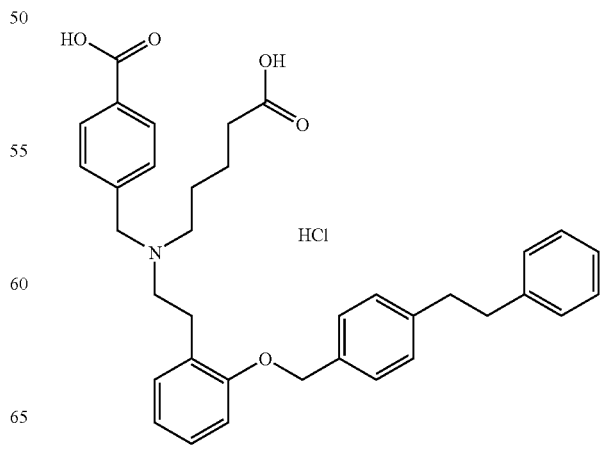

262.60 mg (0.442 mmol) of methyl 4-[((5-methoxy-5-oxopentyl){2-[(4-phenethyl-benzyl)oxy]phenethyl}amino)methyl]benzoate from Ex. 7 are initially charged in 2 ml of dioxane and admixed with 0.2 ml of 45 percent strength NaOH, and the mixture is heated at 60° C. for 18 hours. The dioxane is distilled off under reduced pressure and the residue is taken up in water and adjusted to pH 4 using 2N HCl. The resulting precipitate is filtered off and dried. 50 mg of the product are dissolved in 2 ml of methylene chloride and 1 ml of methanol, and the mixture is admixed with 1 ml of a 4N solution of HCl in dioxane and stirred at room temperature for 1 h. The solvent is distilled off under reduced pressure and the residue is stirred with ether/petroleum ether.

Yield: 34.0 mg (56.2% of theory) white crystals $^1$H-NMR (300 MHz, d$^4$-methanol): δ 1.52 (m, 2H), 1.72 (m, 2H), 2.25 (t, 2H), 2.90 (m, 4H), 3.15 (m, 2H), 3.30 (m, 4H), 4.38 (s, 2H), 5.08 (s, 2H), 6.8-7.3 (m, 13H), 7.55 (d, 2H), 8.05 (d, 2H).

Example 8a: 4-[((4-Carboxybutyl)-{2-[(4-phenethyl-benzyl)oxy]phenethyl}amino)-methyl]benzoic Acid The free carboxylic acid was prepared by the same route, but without the last step, i.e. the reaction with HCl:

$^1$H-NMR (300 MHz, d$^6$-DMSO): δ=1.45 (m, 4H), 2.10 (m, 2H), 2.30-3.60 (m), 5.08 (s, 2H), 6.80 (m, 1H), 6.90 (m, 1H), 7.00-7.50 (m, 13H), 12.5 (bs).

The following compounds can be prepared analogously:

| Example | Structure | Physical data: $^1$H-NMR (δ in ppm, selection)[1] or LC/MS (mass/retention time [min])[2] |
|---|---|---|
| 9 (from I and 5-phenylpentyl 1-bromide by process D) | 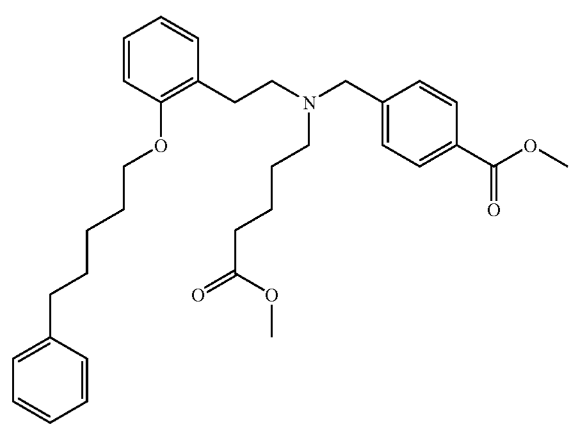 | 2.40 (dd), 2.57 (m), 2.72 (m), 3.53 (s), 3.60 (s), 3.82 (s), 3.82 (s) |
| 10 (from I and 4-phenylbutyl 1-bromide by process D) | 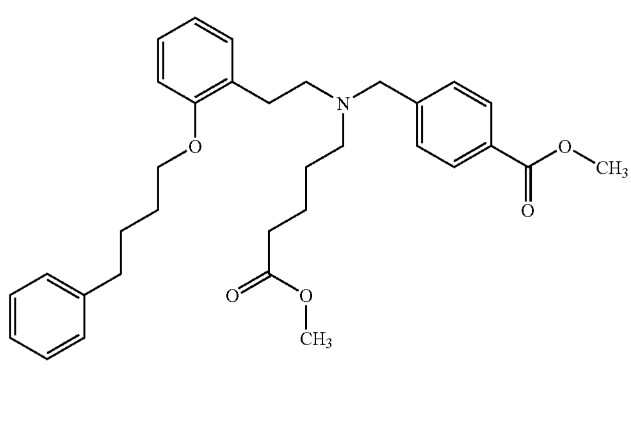 | 2.41 (dd), 2.59 (m), 2.73 (m), 3.54 (s), 3.63 (s), 3.84 (s), 3.83 (s) |

-continued

| Example | Structure | Physical data: ¹H-NMR (δ in ppm, selection)[1] or LC/MS (mass/retention time [min])[2] |
|---|---|---|
| 11 (from 9 by process E) | 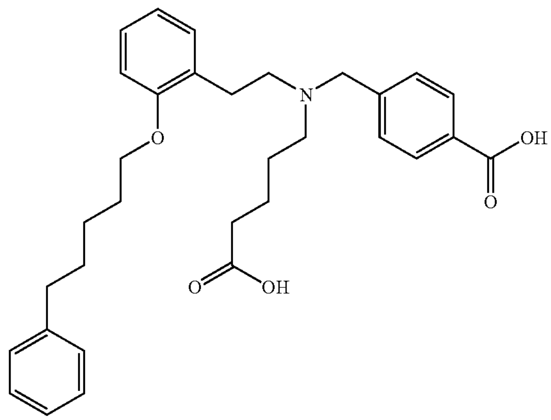 | 2.45 (dd), 2.55 (m), 2.68 (m), 3.62 (s), 3.85 (t), 12.3 (br.s) |
| 12 (from 10 by process E) | 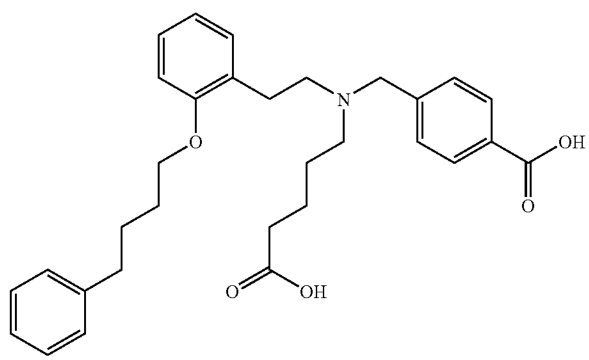 | 2.43 (dd), 2.57 (m), 2.66 (m), 3.64 (s), 3.87 (t), 12.3 (br.s) |
| 13 (from III and 4-(chloro-methyl)stilbene by process D) | 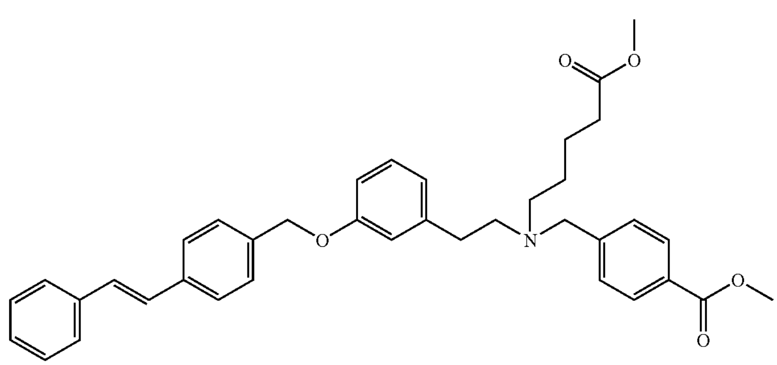 | 592 (M + 1), Rt = 4.23 |
| 14 (from I and allyl bromide by process D) | 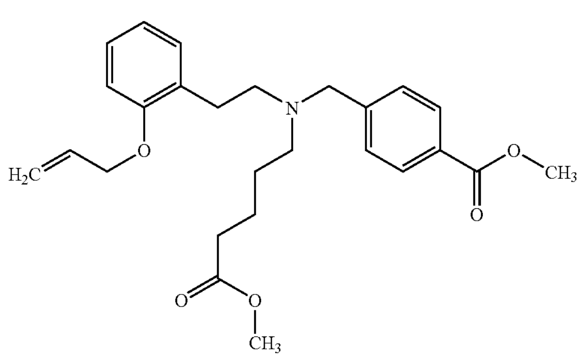 | 2.40 (dd), 2.57 (m), 2.72 (m), 3.53 (s), 3.60 (s), 3.82 (s), 3.89 (d) |

-continued

| Example | Structure | Physical data: $^1$H-NMR ($\delta$ in ppm, selection)[1] or LC/MS (mass/retention time [min])[2] |
|---|---|---|
| 15 (from 14 by process E) | 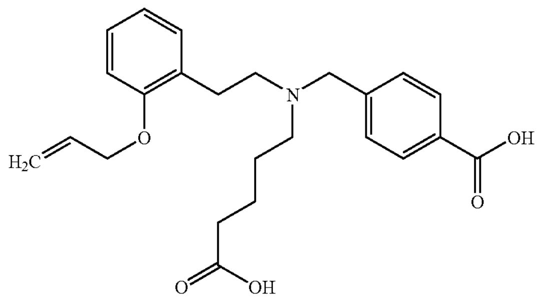 | 2.44 (dd), 2.56 (m), 2.65 (m), 3.65 (s), 3.87 (d), 12.3 (br.s) |
| 16 (from I and 4-(chloromethyl)biphenyl by process D) | | 2.40 (dd), 2.57 (m), 2.72 (m), 3.53 (s), 3.60 (s), 3.82 (s), 5.08 (s) |
| 17 (from I and 4-(4'-chloro)-phenoxybenzyl chloride by process D) | 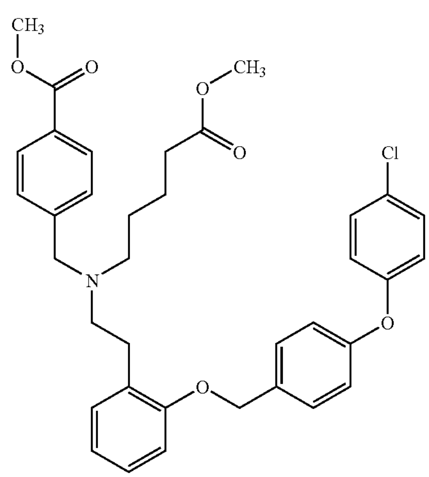 | 2.42 (dd), 2.59 (m), 2.73 (m), 3.54 (s), 3.62 (s), 3.84 (s), 5.10 (s) |

-continued

| Example | Structure | Physical data: $^1$H-NMR (δ in ppm, selection)$^{1)}$ or LC/MS (mass/retention time [min])$^{2)}$ |
|---|---|---|
| 18 (from I and 4-ethylbenzyl chloride by process D) | 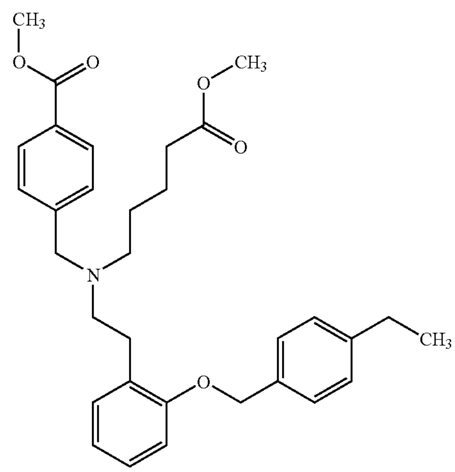 | 2.41 (dd), 2.55 (m), 2.70 (m), 3.55 (s), 3.62 (s), 3.84 (s), 5.08 (s) |
| 19 (from I and 4-t-butylbenzyl chloride by process D) | 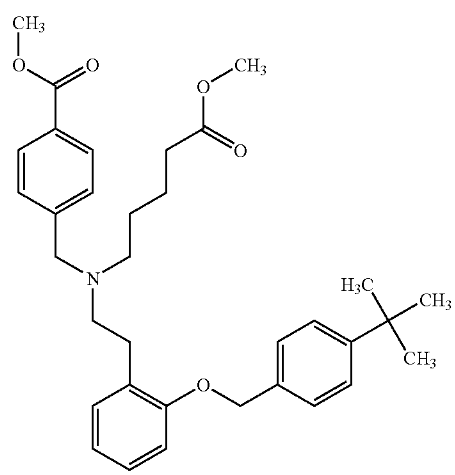 | 2.39 (dd), 2.59 (m), 2.70 (m), 3.55 (s), 3.62 (s), 3.84 (s), 5.10 (s) |
| 20 (from I and 4-chlorobenzyl chloride by process D) | 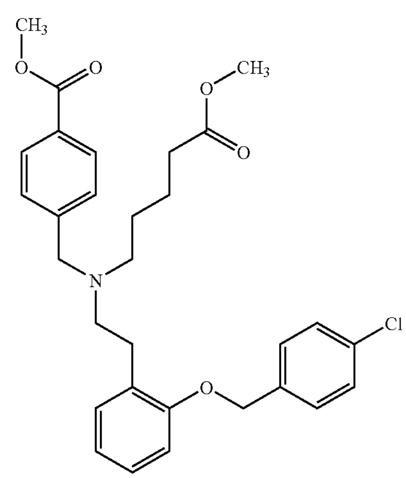 | 2.40 (dd), 2.55 (m), 2.74 (m), 3.52 (s), 3.55 (s), 3.75 (s), 5.05 (s) |

-continued

| Example | Structure | Physical data: ¹H-NMR (δ in ppm, selection)[1] or LC/MS (mass/retention time [min])[2] |
|---|---|---|
| 21 (from I and 4-phenylmethyl-oxybenzyl chloride by process D) | 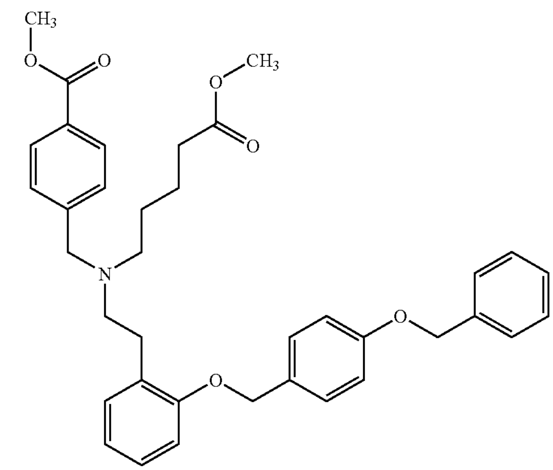 | 2.44 (dd), 2.58 (m), 2.69 (m), 3.55 (s), 3.64 (s), 3.83 (s), 5.06 (s) |
| 22 (from I and 4-methoxy-benzyl chloride by process D) | 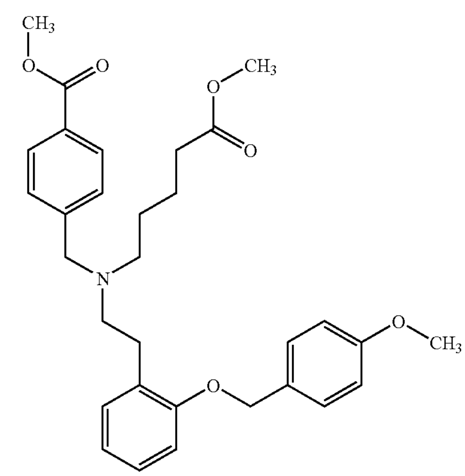 | 2.39 (dd), 2.59 (m), 2.70 (m), 3.55 (s), 3.62 (s), 3.84 (s), 5.10 (s) |
| 23 (from I and 3-trifluoro-methylbenzyl chloride by process D) | 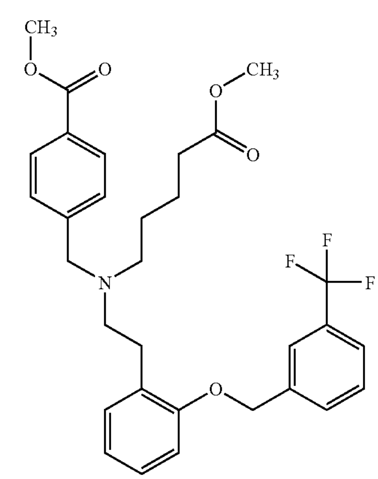 | 2.42 (dd), 2.59 (m), 2.73 (m), 3.54 (s), 3.62 (s), 3.84 (s), 5.10 (s) |

-continued

| Example | Structure | Physical data: $^1$H-NMR (δ in ppm, selection)[1] or LC/MS (mass/retention time [min])[2] |
|---------|-----------|---|
| 24 (from I and 4-allylbenzyl chloride by process D) | 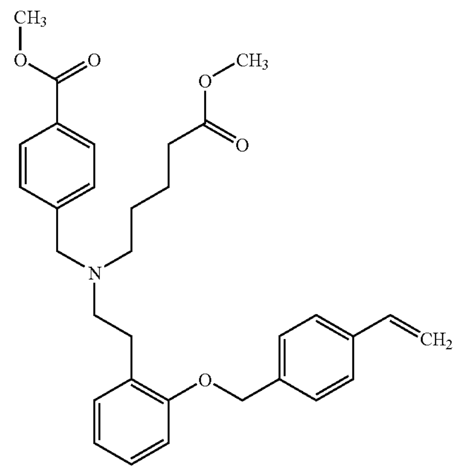 | 2.41 (dd), 2.55 (m), 2.70 (m), 3.55 (s), 3.62 (s), 3.84 (s), 5.08 (s) |
| 25 (from I and 3-bromo-1-propine by process D) | 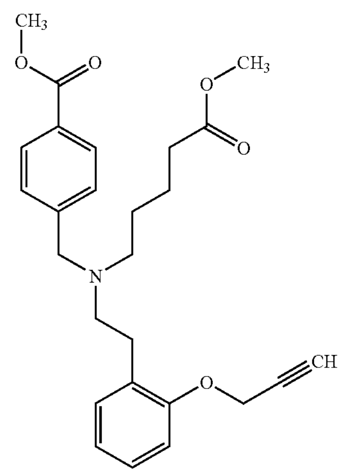 | 2.40 (dd), 2.57 (m), 2.72 (m), 3.53 (s), 3.60 (s), 3.82 (s), 3.91 (d) |
| 26 (from I and 4-methylbenzyl chloride by process D) | 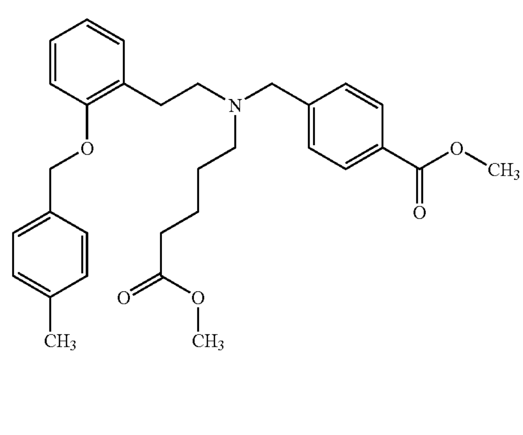 | 2.40 (dd), 2.57 (m), 2.72 (m), 3.53 (s), 3.60 (s), 3.82 (s), 5.08 (s) |

-continued

| Example | Structure | Physical data: $^1$H-NMR ($\delta$ in ppm, selection)[1] or LC/MS (mass/retention time [min])[2] |
|---|---|---|
| 27 (from 16 by process E) | 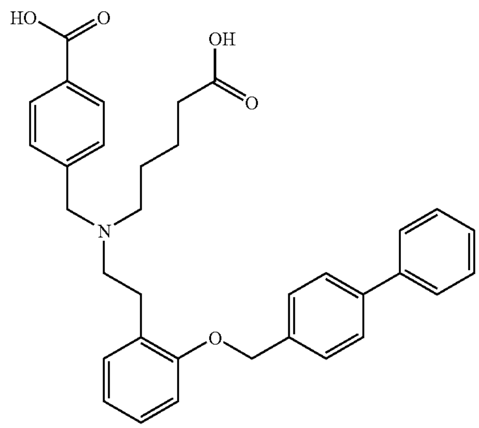 | 2.37 (dd), 2.58 (m), 2.72 (m), 3.61 (s), 5.12 (s), 12.3 (br.s) |
| 28 (from 17 by process E) | 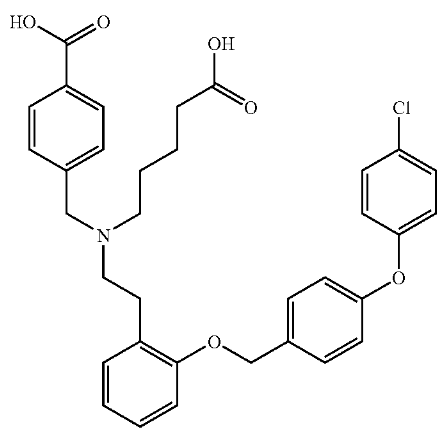 | 2.43 (dd), 2.61 (m), 2.75 (m), 3.61 (s), 5.03 (s), 12.3 (br.s) |
| 29 (from 18 by process E) | 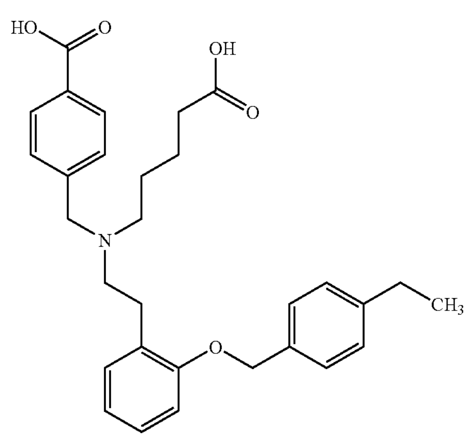 | 2.40 (dd), 2.62 (m), 2.72 (m), 3.63 (s), 5.05 (s), 12.3 (br.s) |

-continued

| Example | Structure | Physical data: $^1$H-NMR (δ in ppm, selection)[1] or LC/MS (mass/retention time [min])[2] |
|---|---|---|
| 30 (from 19 by process E) | 4-[(N-{2-[2-(4-tert-butylbenzyloxy)phenyl]ethyl}-N-(4-carboxyphenylmethyl))amino]pentanoic acid structure | 2.37 (dd), 2.58 (m), 2.72 (m), 3.61 (s), 5.12 (s), 12.3 (br.s) |
| 31 (from 20 by process E) | 4-[(N-{2-[2-(4-chlorobenzyloxy)phenyl]ethyl}-N-(4-carboxyphenylmethyl))amino]pentanoic acid structure | 2.43 (dd), 2.61 (m), 2.75 (m), 3.61 (s), 5.03 (s), 12.3 (br.s) |
| 32 (from 21 by process E) | 4-[(N-{2-[2-(4-benzyloxybenzyloxy)phenyl]ethyl}-N-(4-carboxyphenylmethyl))amino]pentanoic acid structure | 2.43 (dd), 2.61 (m), 2.75 (m), 3.61 (s), 5.03 (s), 12.3 (br.s) |

-continued

| Example | Structure | Physical data: $^1$H-NMR (δ in ppm, selection)[1] or LC/MS (mass/retention time [min])[2] |
|---|---|---|
| 33 (from 6 by process E) | 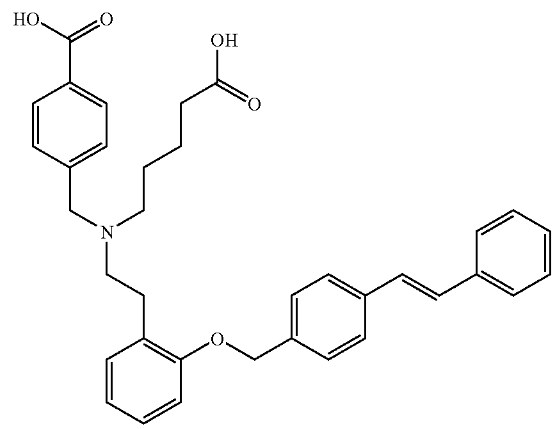 | 2.37 (dd), 2.58 (m), 2.72 (m), 3.61 (s), 5.12 (s), 12.3 (br.s) |
| 34 (from 22 by process E) | 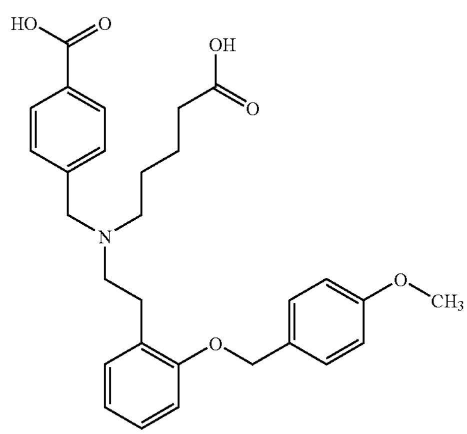 | 2.43 (dd), 2.61 (m), 2.75 (m), 3.61 (s), 5.03 (s), 12.3 (br.s) |
| 35 (from 23 by process E) | 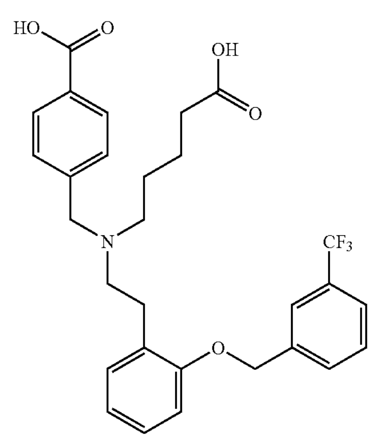 | 2.37 (dd), 2.58 (m), 2.72 (m), 3.61 (s), 5.12 (s) |

-continued

| Example | Structure | Physical data: $^1$H-NMR ($\delta$ in ppm, selection)[1] or LC/MS (mass/retention time [min])[2] |
|---|---|---|
| 36 (from 24 by process E) | 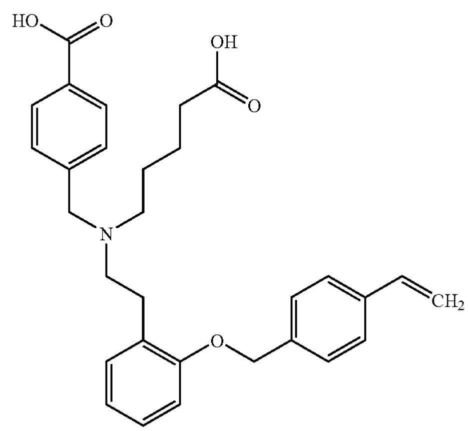 | 2.43 (dd), 2.61 (m), 2.75 (m), 3.61 (s), 5.03 (s), 12.3 (br.s) |
| 37 (from 25 by process E) | 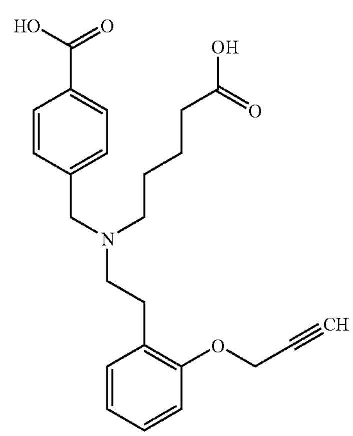 | 2.44 (dd), 2.56 (m), 2.65 (m), 3.65 (s), 3.90 (d), 12.3 (br.s) |
| 38 (from 26 by process E) | 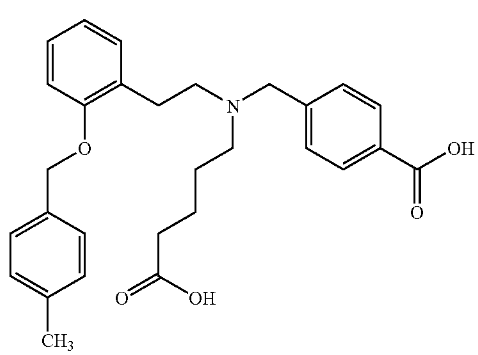 | 2.37 (dd), 2.58 (m), 2.72 (m), 3.61 (s), 5.12 (s), 12.3 (br.s) |

-continued

| Example | Structure | Physical data: $^1$H-NMR (δ in ppm, selection)[1] or LC/MS (mass/retention time [min])[2] |
|---|---|---|
| 39 (from V and ethyl 6-bromohexanoate by process A) | | 1.00-1.20 (m), 1.30-1.60 (m), 2.20 (t), 2.30-2.70 (m), 3.60 (s), 3.80 (m), 4.00 (q), 6.80 (m), 7.0-7.30 (m), 7.40 (d), 7.90 (d) |
| 40 (from 39 by process E) | | 1.22 (m), 1.40 (m), 1.60 (m), 2.15 (t), 2.40-2.60 (m), 2.70 (m), 3.65 (s), 3.86 (t), 6.75-6.9 (m), 7.0-7.3 (m), 7.35 (d), 7.90 (d), 12.30 (bs). |
| 41 (from V and ethyl 4-bromobutanoate by process A) | | 546 (M + 1), Rt = 4.01 |

-continued

| Example | Structure | Physical data: ¹H-NMR ($\delta$ in ppm, selection)[1] or LC/MS (mass/retention time [min])[2] |
|---|---|---|
| 42 (from V and ethyl 4-bromo-2-butenoate by process A) | 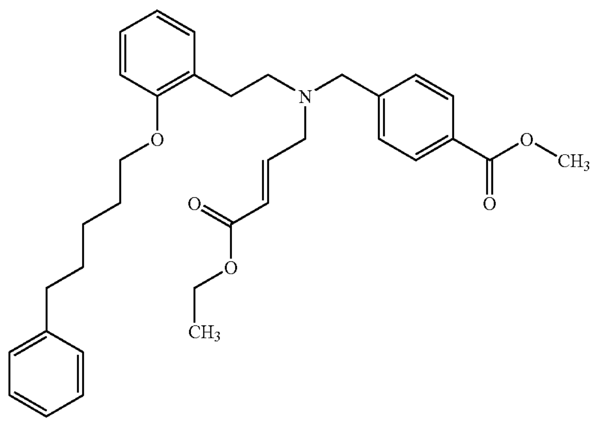 | 544 (M + 1), Rt = 4.12 |
| 43 (from V and ethyl 3-bromo-propanoate by process A) | 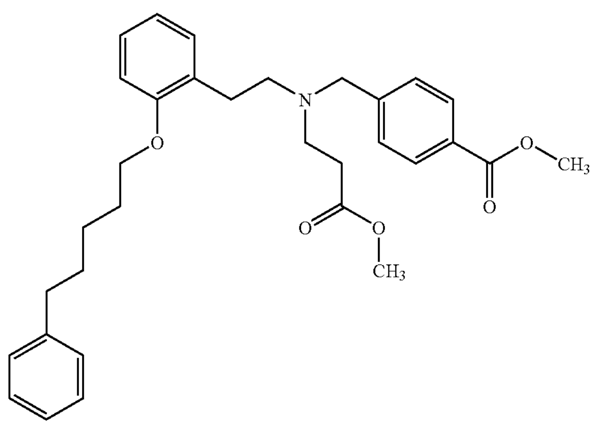 | 518 (M + 1), Rt = 4.27 |
| 44 (from V and diethyl 2-(3-bromo-propyl)malonate by process A) | 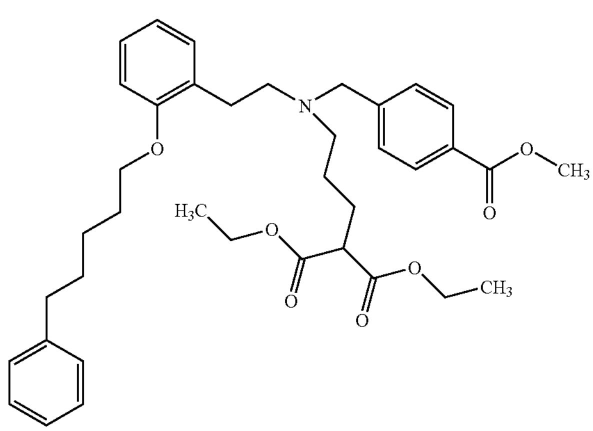 | 518 (M + 1), Rt = 4.25 |

-continued

| Example | Structure | Physical data: $^1$H-NMR (δ in ppm, selection)$^{1)}$ or LC/MS (mass/retention time [min])$^{2)}$ |
|---|---|---|
| 45 (from V and N-ethoxycarbon-ylmethyl)-2-chloroacetamide by process A) | | 575 (M + 1), Rt = 4.34 |
| 46 (from 45 by process E) | | 1.35 (m), 1.60 (m), 2.45 (s), 2.60 (m), 2.75 (m), 3.15 (s), 3.75 (s), 3.85 (t), 6.7-6.9 (m), 7.0-7.1 (m), 7.3 (d), 7.45 (d), 7.85 (d) |
| 47 (from VI and ethyl 5-bromo-pentanoate by process A) | | 1.0-1.6 (m), 2.2 (t), 2.4 (m), 2.55 (m), 2.60 (m), 3.65 (s), 3.85 (s), 4.05 (q), 6.8-6.9 (m), 7.0-7.2 (m), 7.4 (d), 7.9 (d) |

-continued

| Example | Structure | Physical data: $^1$H-NMR ($\delta$ in ppm, selection)[1] or LC/MS (mass/retention time [min])[2] |
|---|---|---|
| 48 (from VI and ethyl 6-bromohexan- oate by process A) | 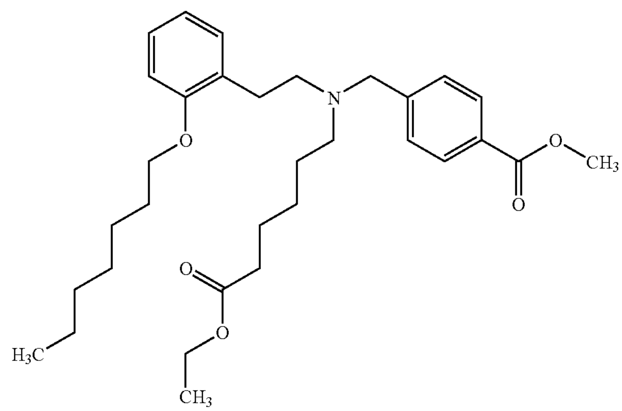 | 1.0-1.6 (m), 2.2 (t), 2.4 (m), 2.55 (m), 2.60 (m), 3.65 (s), 3.85 (s), 4.05 (q), 6.8-6.9 (m), 7.0-7.2 (m), 7.4 (d), 7.9 (d) |
| 49 (from VII and ethyl 6-bromohexan- oate by process A) | 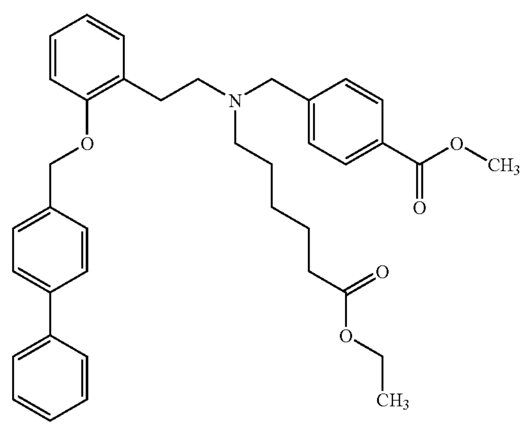 | 1.1 (m), 1.4 (m), 2.15 (t), 2.4 (t), 2.6 (m), 2.8 (m), 3.63 (s), 3.80 (s), 4.0 (q), 5.10 (s), 6.85 (t), 7.0-7.2 (m), 7.4-7.8 (m), 7.9 (d) |
| 50 (from 41 by process E) | 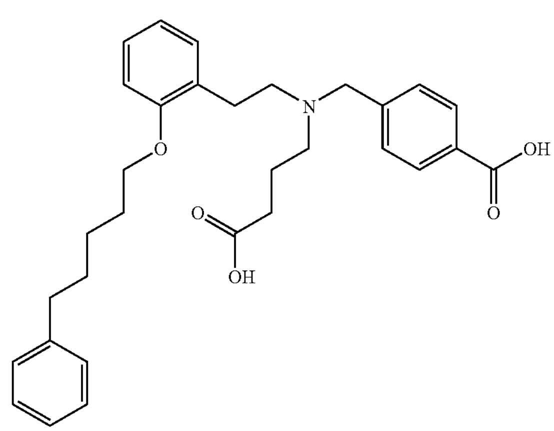 | 504 (M + 1), Rt = 3.30 |

-continued

| Example | Structure | Physical data: <br>$^1$H-NMR ($\delta$ in ppm, selection)[1] or LC/MS (mass/retention time [min])[2] |
|---|---|---|
| 51 <br>(from 42 by process E) | | 502 (M + 1), Rt = 3.34 |
| 52 <br>(from 44 by process E) | | 562 (M + 1), Rt = 3.31 |
| 53 <br>(from 43 by process E) | | 490 (M + 1), Rt = 3.34 |

-continued

| Example | Structure | Physical data: <br>¹H-NMR (δ in ppm, selection)[1] or LC/MS (mass/retention time [min])[2] |
|---|---|---|
| 54 (from 47 by process E) | 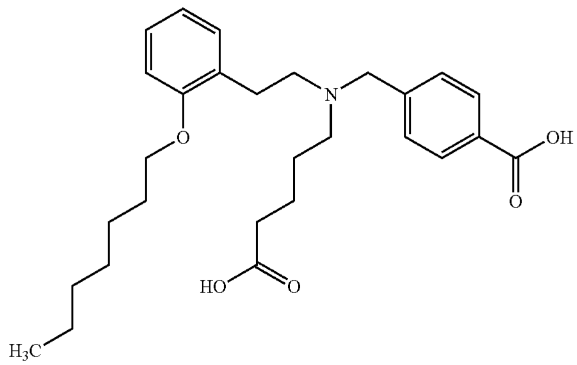 | 1.0-1.6 (m), 2.2 (t), 2.4 (m), 2.55 (m), 2.60 (m), 3.65 (s), 3.85 (s), 4.05 (q), 6.8-6.9 (m), 7.0-7.2 (m), 7.4 (d), 7.9 (d), 12.5 (br.S) |
| 55 (from 48 by process E) | 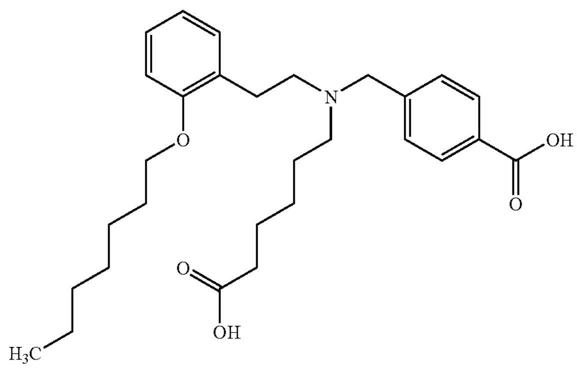 | 1.0-1.6 (m), 2.2 (t), 2.4 (m), 2.55 (m), 2.60 (m), 3.65 (s), 3.85 (s), 4.05 (q), 6.8-6.9 (m), 7.0-7.2 (m), 7.4 (d), 7.9 (d), 12.5 (br.S) |
| 56 (from 49 by process E) | 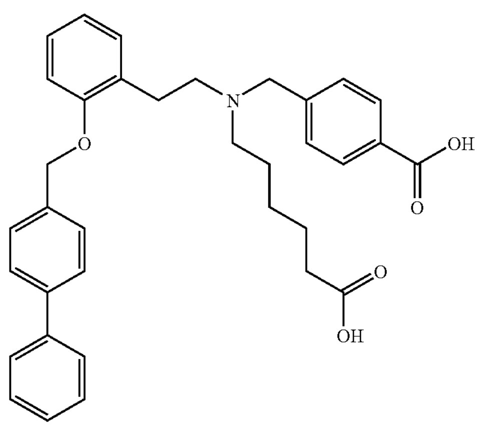 | 1.2 (m), 1.4 (m), 1.7 (m), 2.1 (t), 3.0-3.3 (m), 4.4 (s), 5.15 (s), 7.0-7.8 (m), 8.0 (d), 12.5 (br.s) |
| 57 (from 4 by process E) | 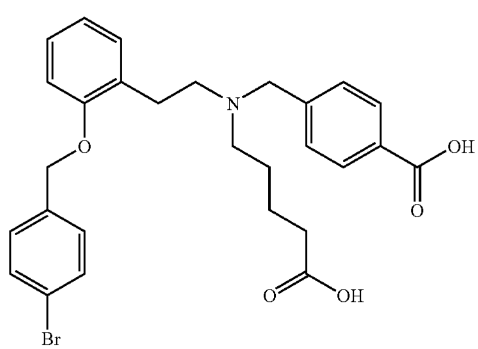 | 1.4 (m), 2.1 (m), 2.3-2.7 (m), 3.65 (m), 5.05 (s), 7.0-7.8 (m), 12.4 (br.s) |

-continued

| Example | Structure | Physical data: ¹H-NMR (δ in ppm, selection)[1] or LC/MS (mass/retention time [min])[2] |
|---|---|---|
| 58 (from I and 4-cyclohexyl-benzyl chloride by process D) | 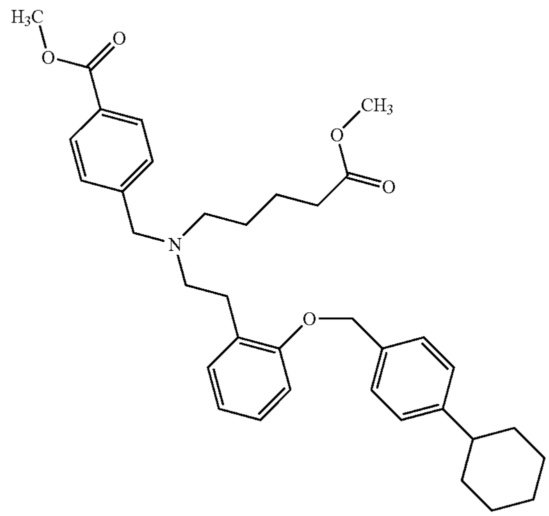 | 572 (M + 1), Rt = 3.43 |
| 59 (from I and 4-(4,5,6-trichloro-pyrimidin-2-yl)benzyl chloride by process D) | 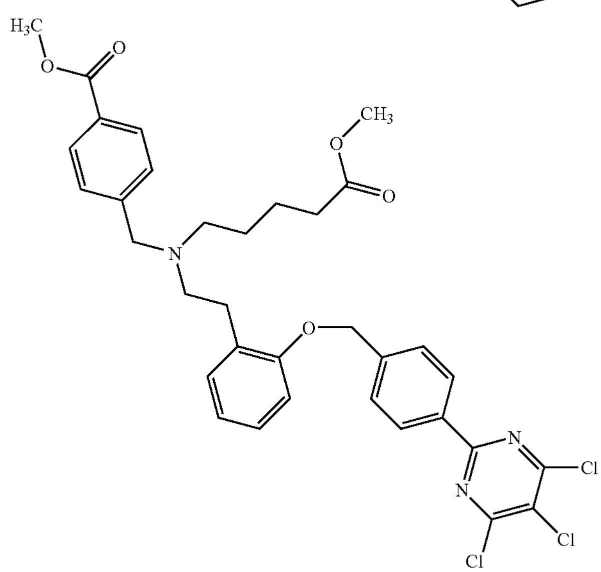 | 670 (M + 1), Rt = 3.39 |
| 60 (from I and 4-(2-trifluoro-methylthiazol-4-yl)benzyl chloride by process D) | 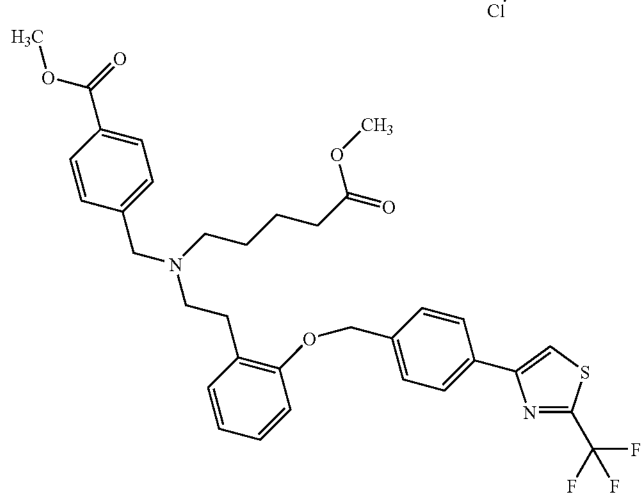 | 641 (M + 1), Rt = 3.79 |

-continued

| Example | Structure | Physical data: $^1$H-NMR (δ in ppm, selection)[1] or LC/MS (mass/retention time [min])[2] |
|---|---|---|
| 61 (from I and 5-(4-methoxy-phenyl)-3-chloromethyl1,2,4-oxadiazole by process D) | | 588 (M + 1), Rt = 3.45 |
| 62 (from I and 2-phenyl-4-chloromethyl-thiazole by process D) | | 573 (M + 1), Rt = 3.51 |
| 63 (from I and 4-1,2,3-thiadiazol-4-yl-benzylchloride by process D) | | 574 (M + 1), Rt = 3.40 |

-continued

| Example | Structure | Physical data: $^1$H-NMR ($\delta$ in ppm, selection)$^{1)}$ or LC/MS (mass/retention time [min])$^{2)}$ |
|---|---|---|
| 64 (from I and 4-trifluoromethyl-mercaptyl-benzyl chloride by process D) | 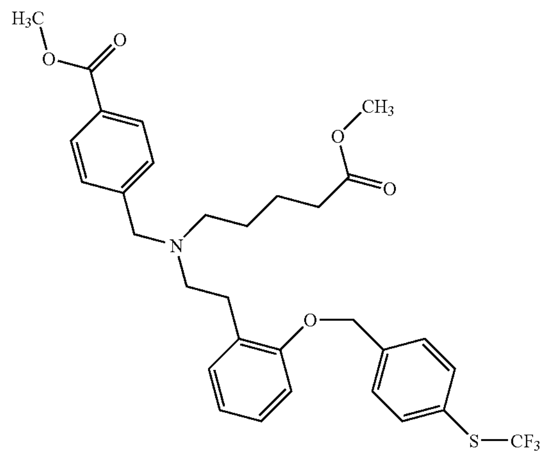 | 590 (M + 1), Rt = 3.74 |
| 65 (from I and 4-fluoro-3-phenoxybenzyl chloride by process D) | 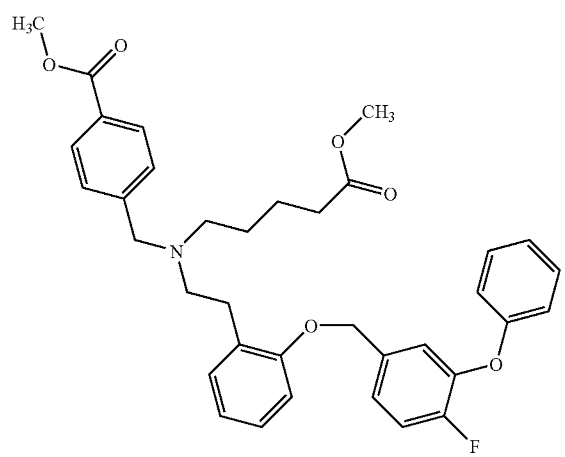 | 600 (M + 1), Rt = 3.72 |
| 66 (from I and 2-chloromethyl-5,6,7,8-tetrahydronaphthalene by process D) | | 544 (M + 1), Rt = 3.74 |

-continued

| Example | Structure | Physical data: $^1$H-NMR (δ in ppm, selection)$^{1)}$ or LC/MS (mass/retention time [min])$^{2)}$ |
|---|---|---|
| 67 (from II and (4-chloromethyl)stilbene by process D) | | 592 (M + 1), Rt = 3.70 |
| 68 (from I and 4-nitrobenzyl chloride by process D) | 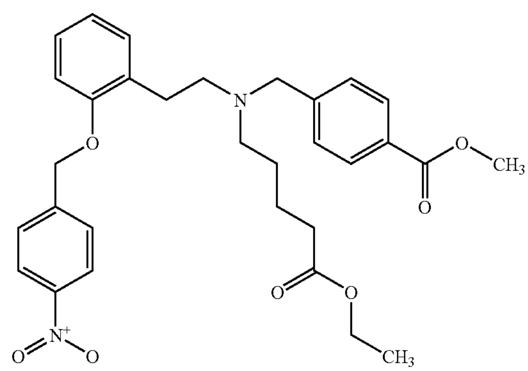 | 1.1 (m), 1.4 (m), 2.15 (t), 2.4 (t), 2.6 (m), 2.8 (m), 3.63 (s), 3.80 (s), 4.0 (q), 5.10 (s), 6.85 (t), 7.0-7.2 (m), 7.4-7.8 (m), 7.9 (d) |
| 69 (from 4 and 4-methylphenyl-boronic acid by process F) | 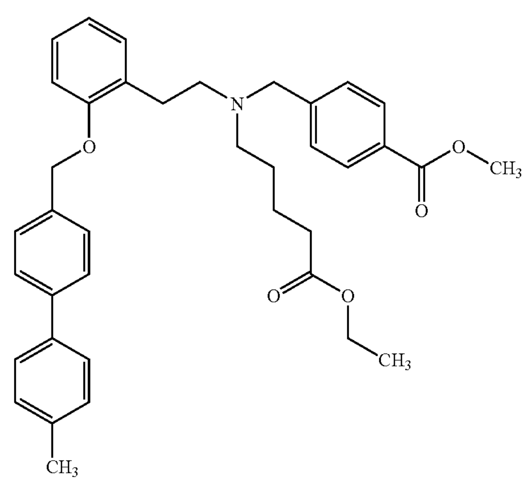 | 594 (M + 1), Rt = 3.39 |

-continued

| Example | Structure | Physical data: $^1$H-NMR (δ in ppm, selection)[1] or LC/MS (mass/retention time [min])[2] |
|---|---|---|
| 70 (from 58 by process E) | 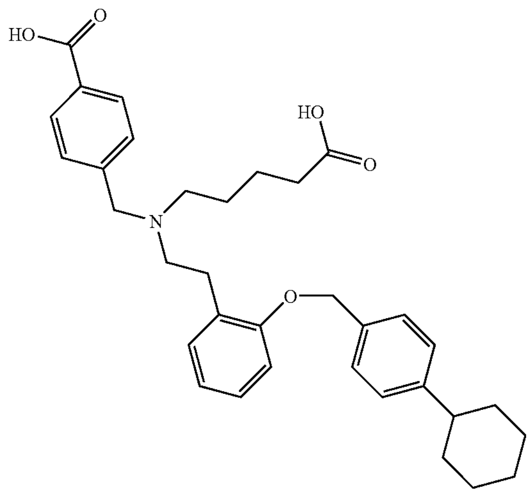 | 544 (M + 1), Rt = 3.62 |
| 71 (from 59 by process E) | 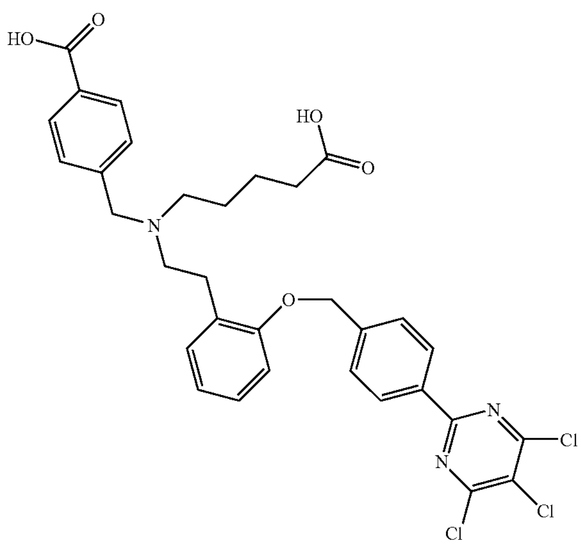 | 643 (M + 1), Rt = 3.30 |
| 72 (from 60 by process E) | 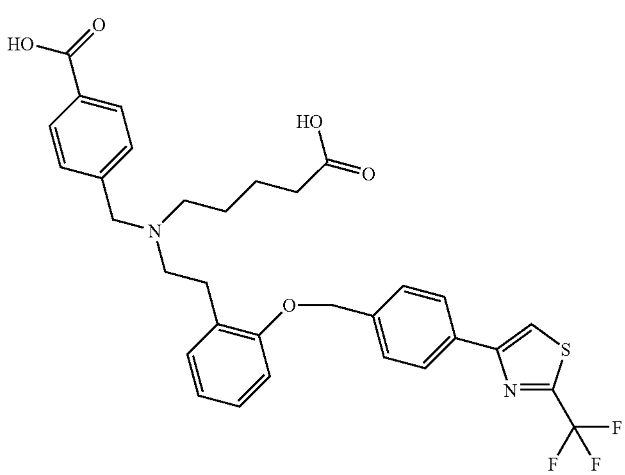 | 612 (M + 1), Rt = 3.47 |

-continued
| Example | Structure | Physical data: $^1$H-NMR (δ in ppm, selection)[1] or LC/MS (mass/retention time [min])[2] |
|---|---|---|
| 73 (from 62 by process E) | 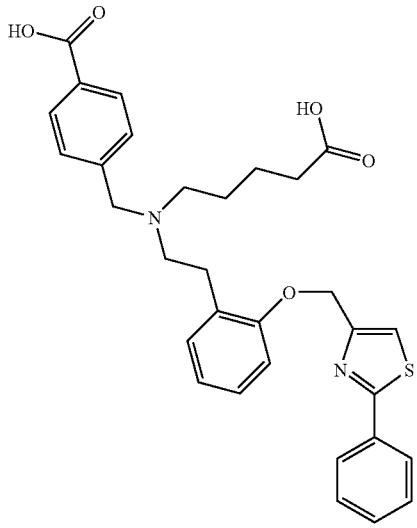 | 545 (M + 1), Rt = 3.18 |
| 74 (from 64 by process E) | 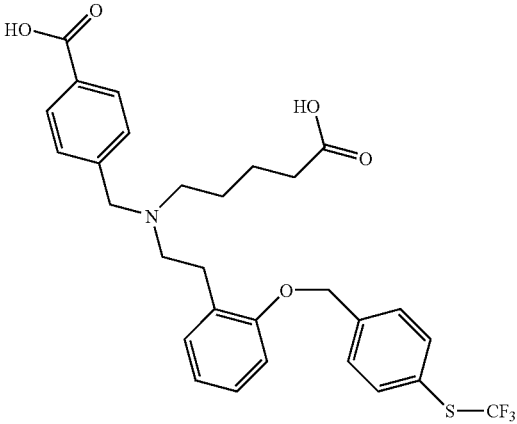 | 562 (M + 1), Rt = 3.39 |
| 75 (from 65 by process E) | 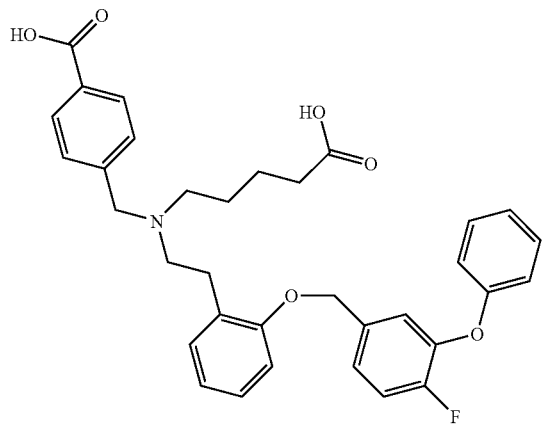 | 572 (M + 1), Rt = 3.40 |

-continued

| Example | Structure | Physical data: $^1$H-NMR (δ in ppm, selection)$^{1)}$ or LC/MS (mass/retention time [min])$^{2)}$ |
|---|---|---|
| 76 (from 66 by process E) | 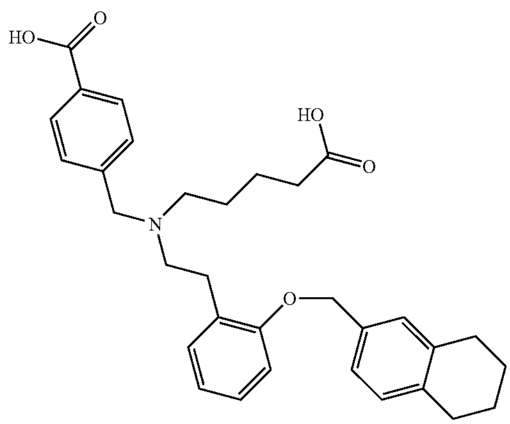 | 516 (M + 1), Rt = 3.38 |
| 77 (from 4 and 4-methoxyphenyl-boronic acid by process F) | 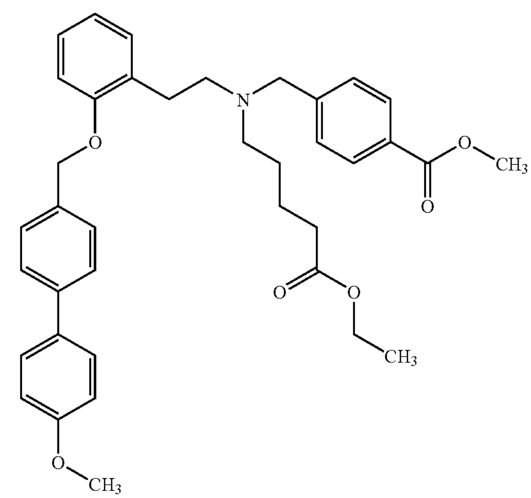 | 610 (M + 1), Rt = 3.41 |
| 78 (from I and 4-phenylamino-carbonylbenzyl chloride by process D) | 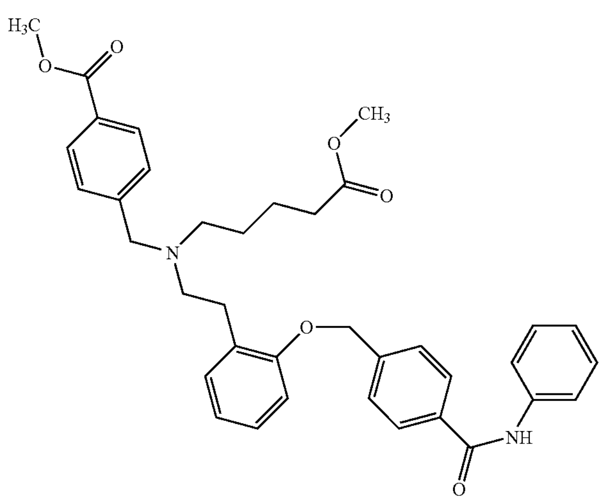 | 609 (M + 1), Rt = 3.39 |

-continued

| Example | Structure | Physical data: $^1$H-NMR (δ in ppm, selection)$^{1)}$ or LC/MS (mass/retention time [min])$^{2)}$ |
|---------|-----------|---|
| 79 (from I and 2-(4-chlorophenyl)-4-chloromethylthiazole by process D) | | 608 (M + 1), Rt = 3.43 |
| 80 (from I and 4-phenoxybutyloxybenzyl chloride by process D) | | 654 (M + 1), Rt = 3.45 |

-continued

| Example | Structure | Physical data: ¹H-NMR (δ in ppm, selection)[1] or LC/MS (mass/retention time [min])[2] |
|---|---|---|
| 81 (from I and 3-phenoxybenzyl chloride by process D) | 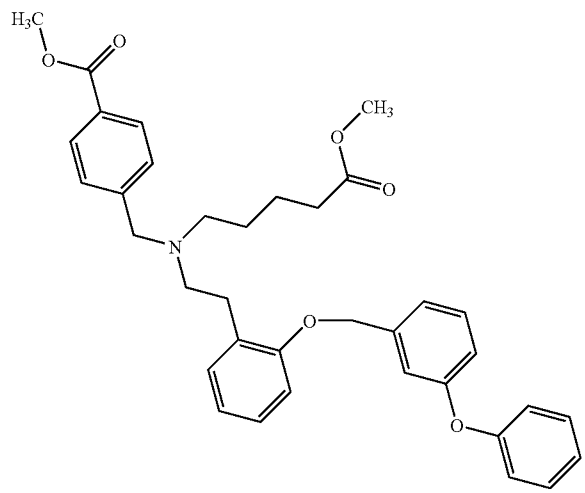 | 582 (M + 1), Rt = 3.34 |
| 82 (from I and 4-(4,6-dichloro-pyrimidin-2-yl)-mercaptobenzyl chloride by process D) | 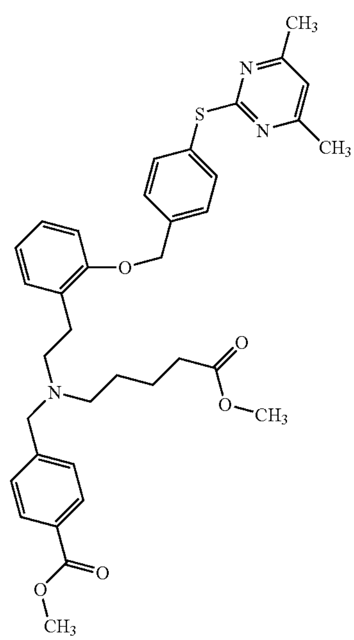 | 628 (M + 1), Rt = 3.19 |

| Example | Structure | Physical data: $^1$H-NMR (δ in ppm, selection)[1] or LC/MS (mass/retention time [min])[2] |
|---|---|---|
| 83 (from I and 4-(4-cyanophenoxy)-benzyl chloride by process D) | 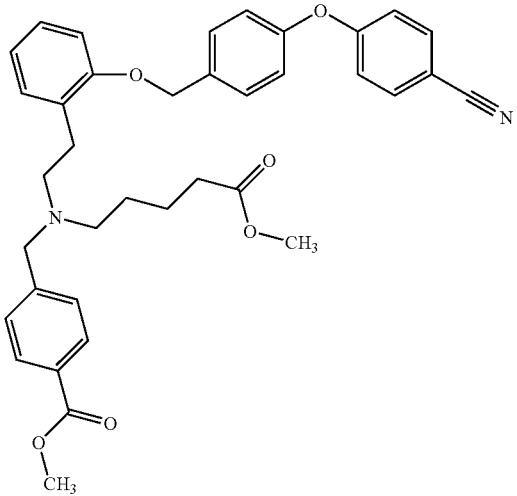 | 607 (M + 1), Rt = 3.22 |
| 84 (from I and 4-(4-trifluoromethylphenoxybenzyl chloride by process D) | 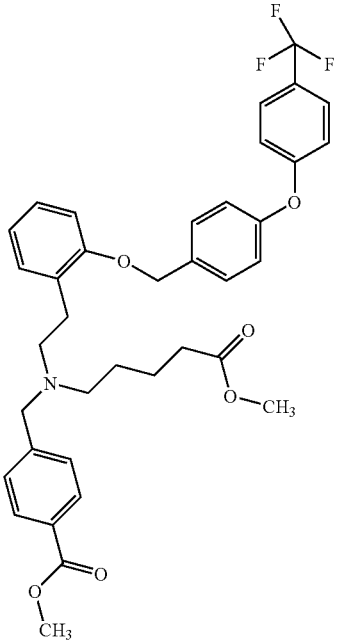 | 650 (M + 1), Rt = 4.01 |

-continued

| Example | Structure | Physical data: ¹H-NMR (δ in ppm, selection)¹⁾ or LC/MS (mass/retention time [min])²⁾ |
|---|---|---|
| 85 (from I and 4-(4-tolyl-sulphonyl-methylbenzyl bromide by process D) | 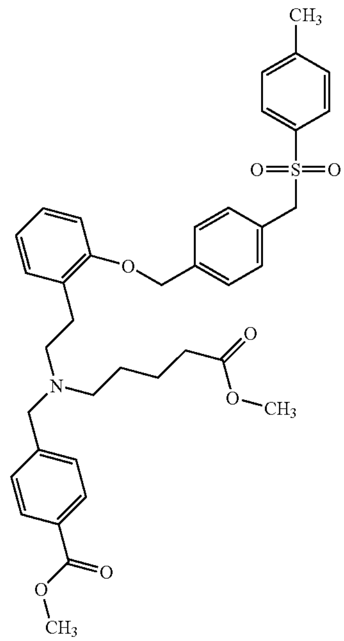 | 658 (M + 1), Rt = 3.85 |
| 86 (from 84 by process E) | 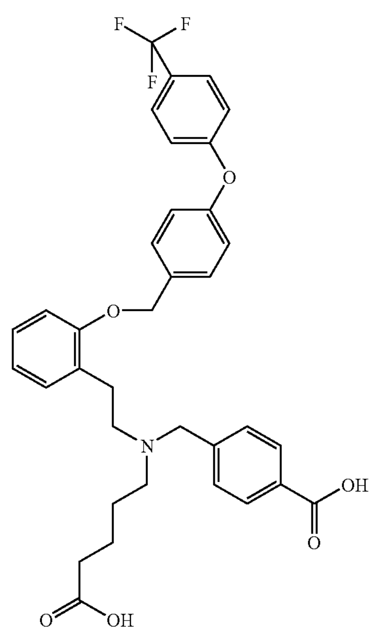 | 622 (M + 1), Rt = 3.62 |

-continued

| Example | Structure | Physical data: $^1$H-NMR (δ in ppm, selection)$^{1)}$ or LC/MS (mass/retention time [min])$^{2)}$ |
|---|---|---|
| 87 (from 5 by process E) | 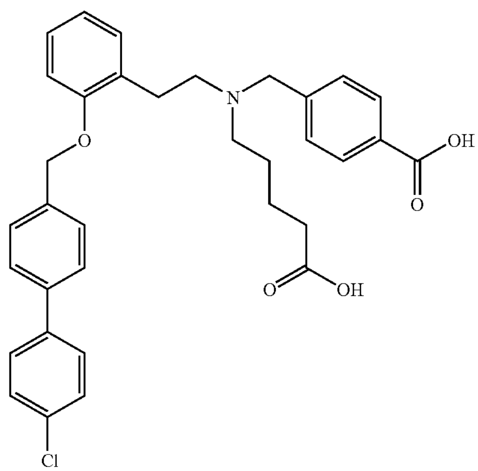 | 1.2 (m), 1.4 (m), 1.7 (m), 2.1 (t), 3.0-3.3 (m), 4.4 (s), 5.15 (s), 7.0-7.8 (m), 8.0 (d), 12.5 (br.s) |
| 88 (from 77 by process E) | 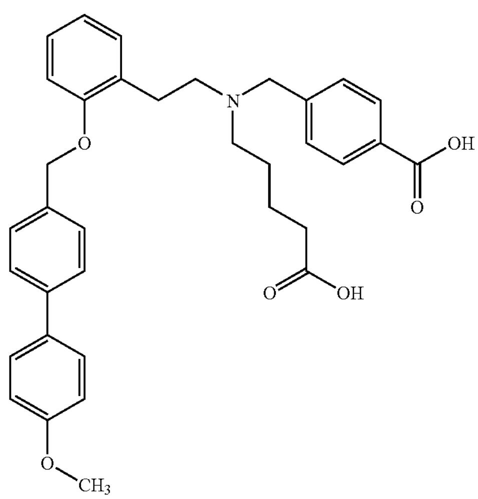 | 1.2 (m), 1.4 (m), 1.7 (m), 2.1 (t), 3.0-3.3 (m), 3.9 (s), 4.4 (s), 5.15 (s), 7.0-7.8 (m), 8.0 (d), 12.5 (br.s) |
| 89 (from 4 and 3-thiophene-boronic acid by process F) | 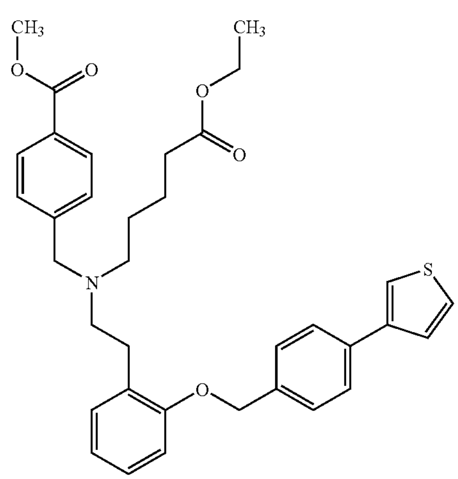 | 586 (M + 1), Rt = 4.21 |

-continued

| Example | Structure | Physical data: $^1$H-NMR (δ in ppm, selection)$^{1)}$ or LC/MS (mass/retention time [min])$^{2)}$ |
|---|---|---|
| 90 (from 4 and 3-chlorophenyl-boronic acid by process F) | 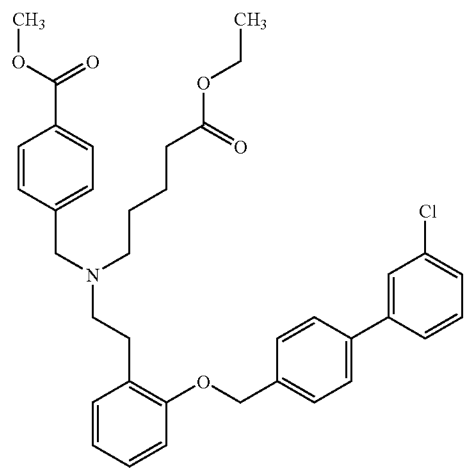 | 615 (M + 1), Rt = 4.19 |
| 91 (from 4 and 3-methylcarbon-ylaminophenyl-boronic acid by process F) | 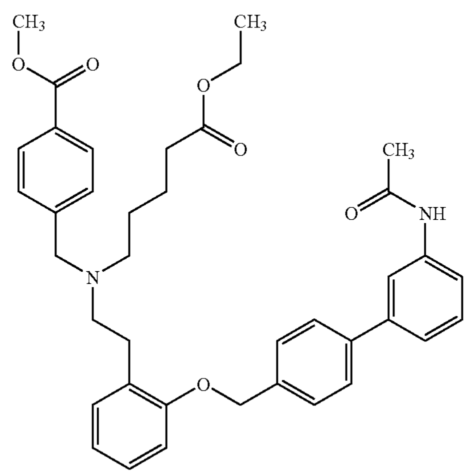 | 637 (M + 1), Rt = 4.30 |
| 92 (from 4 and 2-methoxyphenyl-boronic acid by process F) | 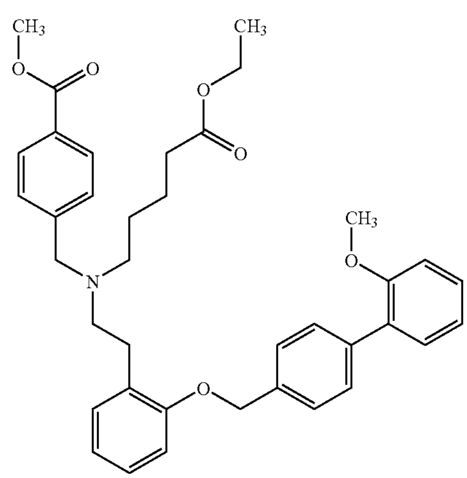 | 610 (M + 1), Rt = 4.25 |

-continued

| Example | Structure | Physical data: ¹H-NMR ($\delta$ in ppm, selection)[1] or LC/MS (mass/retention time [min])[2] |
|---|---|---|
| 93 (from 4 and 3-nitrophenyl-boronic acid by process F) | 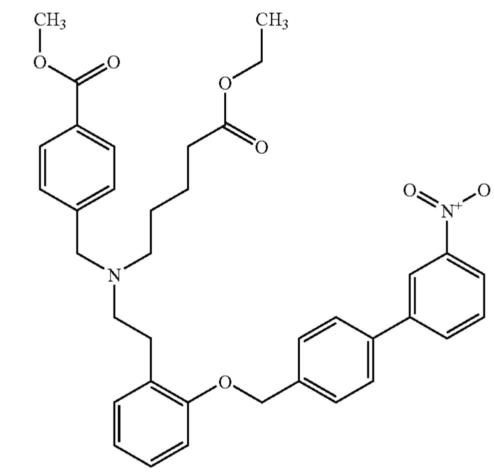 | 625 (M + 1), Rt = 4.19 |
| 94 (from 4 and 2,4-dichlorophenyl-boronic acid by process F) | 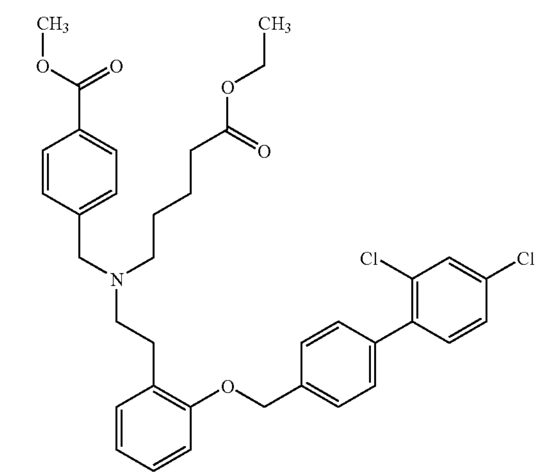 | 649 (M + 1), Rt = 4.25 |
| 95 (from 4 and 3-methylphenyl-boronic acid by process F) | 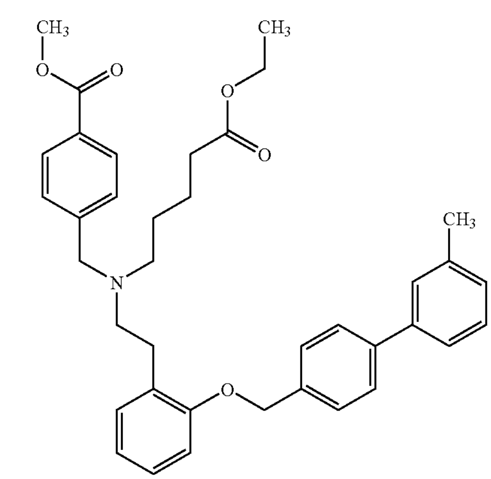 | 594 (M + 1), Rt = 4.33 |

-continued

| Example | Structure | Physical data: ¹H-NMR (δ in ppm, selection)[1] or LC/MS (mass/retention time [min])[2] |
|---|---|---|
| 96 (from 4 and 3-chloro-4-fluoro-phenylboronic acid by process F) | 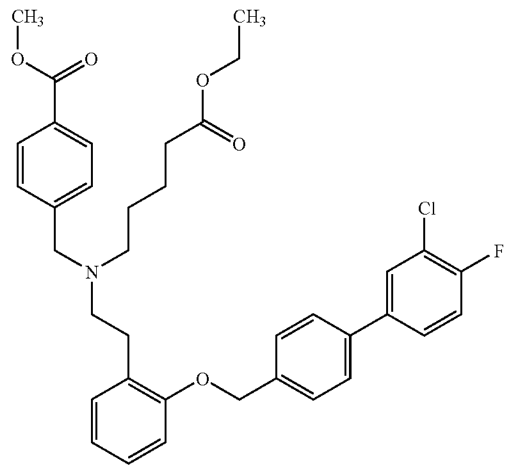 | 633 (M + 1), Rt = 4.23 |
| 97 (from 4 and 3-aminophenyl-boronic acid by process F) | 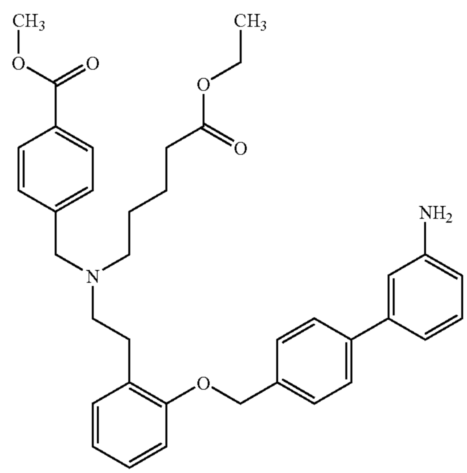 | 595 (M + 1), Rt = 3.23 |
| 98 (from V and methyl 4-(2-bromo-ethyloxy)benzoate by process A and E) | 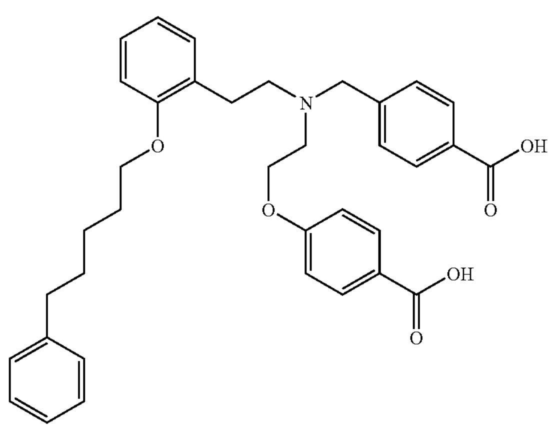 | 582 (M + 1), Rt = 3.45 |

| Example | Structure | Physical data: $^1$H-NMR (δ in ppm, selection)$^{1)}$ or LC/MS (mass/retention time [min])$^{2)}$ |
|---|---|---|
| 99 (from 67 by process E) | 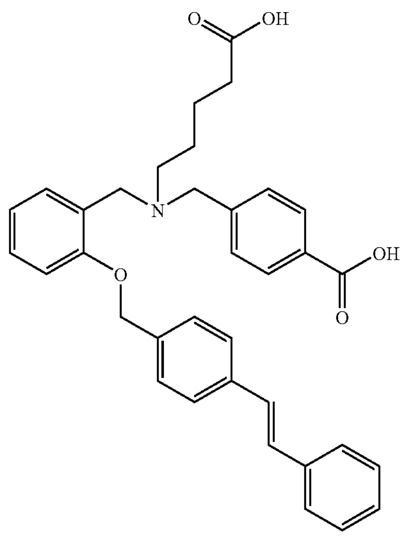 | 550 (M + 1), Rt = 3.38 |
| 100 (from IX and 4-cyclohexyl-benzyl chloride by process D) | 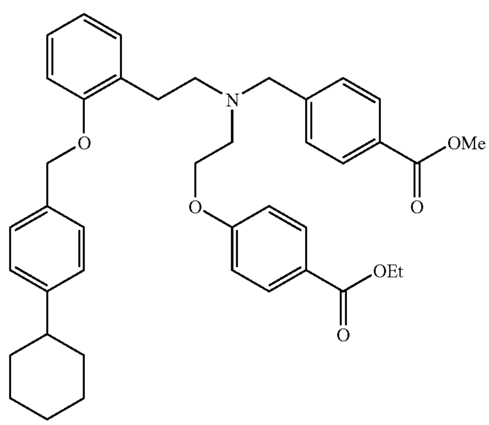 | 1.30 (t, 3H), 1.50-2.00 (m, 10H), 2.50 (m, 1H), 2.90 (m, 6H), 3.80 (s, 2H), 3.95 (m, 5H), 4.40 (q, 2H), 5.00 (s, 2H), 6.70-6.90 (m, 4H), 7.10-7.40 (m, 8H), 8.00 (m, 4H). |
| 101 (from IX and octyl chloride by process D) | 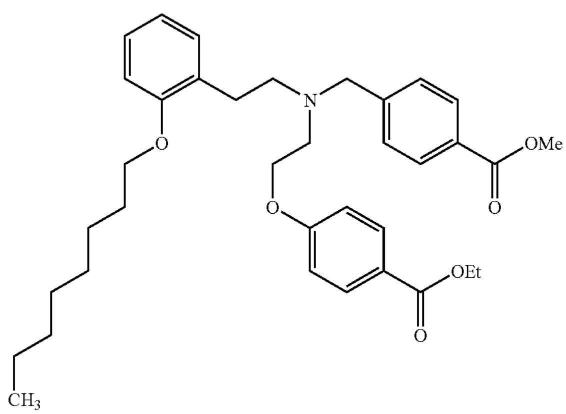 | 0.90 (m, 3H), 1.20-1.80 (m, 15H), 2.80 (s, 4H), 3.00 (t, 3H), 3.80-3.90 (m, 7H), 4.05 (t, 2H), 4.40 (q, 2H), 6.70-6.90 (m, 4H), 7.10-7.40 (m, 8H), 8.00 (m, 4H). |

-continued

| Example | Structure | Physical data: ¹H-NMR (δ in ppm, selection)¹⁾ or LC/MS (mass/retention time [min])²⁾ |
|---|---|---|
| 102 (from 100 by process E) | 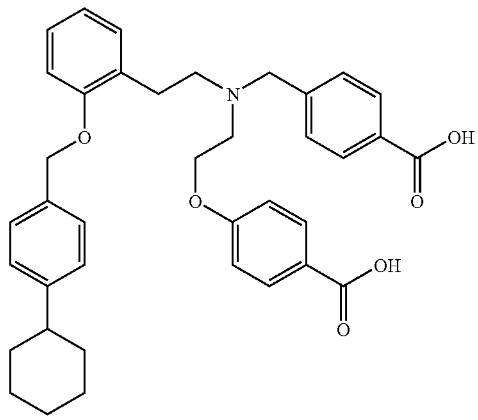 | 1.40-1.20 (m, 5H), 1.60-1.90 (m, 5H), 2.40 (m, 1H), 3.20 (m, 2H), 3.40 (m, 2H), 3.60 (m, 2H), 4.25 (m, 2H), 4.50 (m, 2H), 5.00 (s, 2H), 6.90 (m, 3H), 7.10 (m, 3H), 7.30 (m, 4H), 7.50 (d, 2H), 7.90 (d, 2H), 8.00 (d, 2H). |
| 103 (from 101 by process E) | 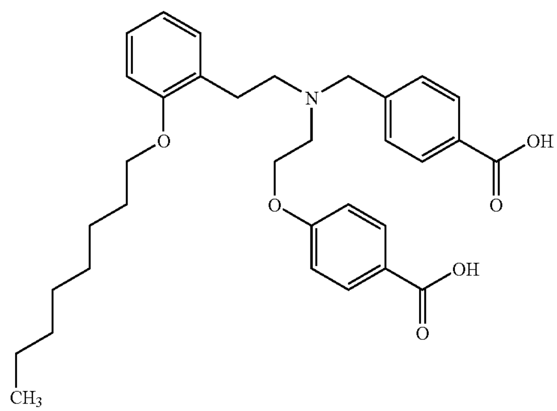 | 0.90 (t, 3H), 1.40-1.20 (m, 10H), 1.60 (m, 2H), 3.00 (m, 2H), 3.20 (m, 2H), 3.40 (m, 2H), 3.90 (t, 2H), 4.30 (m, 4H), 6.90 (m, 2H), 7.00 (m, 2H), 7.20 (m, 2H), 7.50 (d, 2H), 7.95 (d, 2H), 8.05 (d, 2H). |
| 104 (from 94 by process E) | 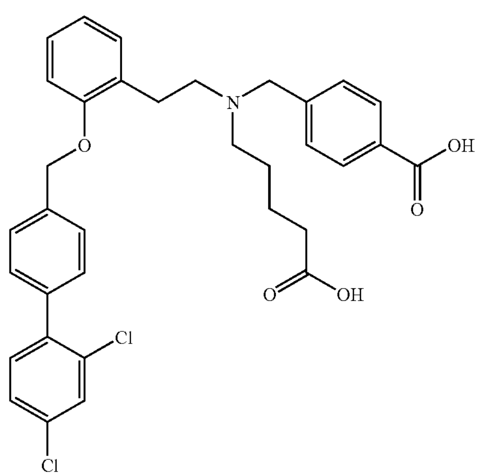 | 2.37 (dd), 2.58 (m), 2.72 (m), 3.61 (s), 5.12 (s), 12.3 (br.s) |

-continued

| Example | Structure | Physical data: $^1$H-NMR (δ in ppm, selection)$^{1)}$ or LC/MS (mass/retention time [min])$^{2)}$ |
| --- | --- | --- |
| 105 (from 4 and 4-fluorophenyl-boronic acid by process F) | 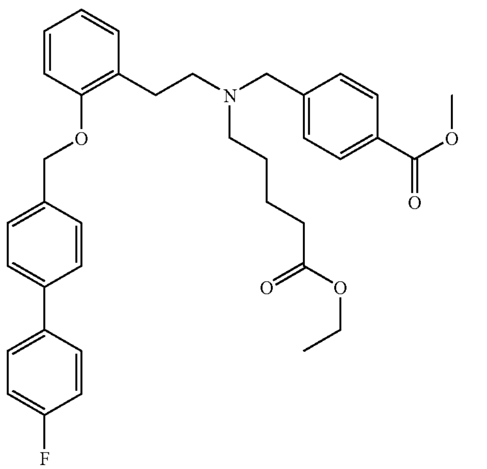 | 1.1 (m), 1.4 (m), 2.15 (t), 2.4 (t), 2.6 (m), 2.8 (m), 3.63 (s), 3.80 (s), 4.0 (q), 5.10 (s), 6.85 (t), 7.0-7.2 (m), 7.4-7.8 (m), 7.9 (d) |
| 106 (from 105 by process E) | 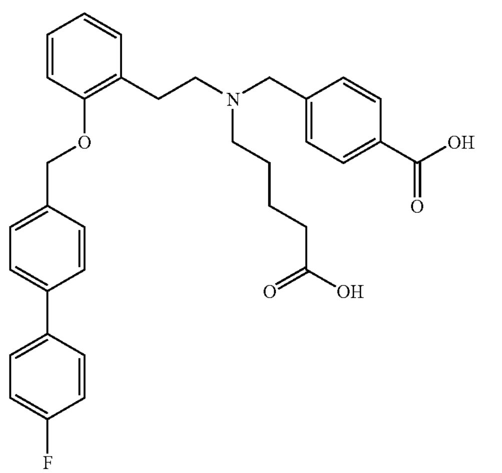 | 555 (M + 1), Rt = 3.32 |
| 107 (from I and 1,5-dibromo-pentane by process D) | 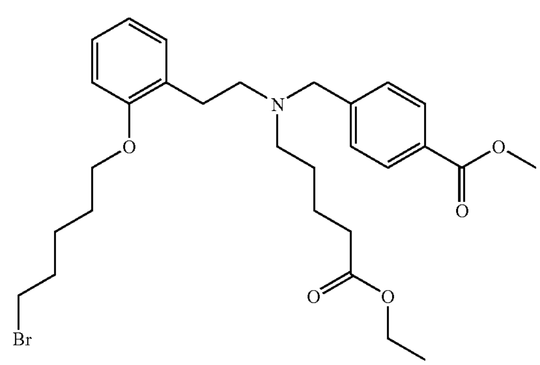 | 561 (M + 1), Rt = 3.53 |

-continued

| Example | Structure | Physical data: ¹H-NMR ($\delta$ in ppm, selection)[1] or LC/MS (mass/retention time [min])[2] |
|---|---|---|
| 108 (from I and 1,2-dibromo-ethane by process D) | 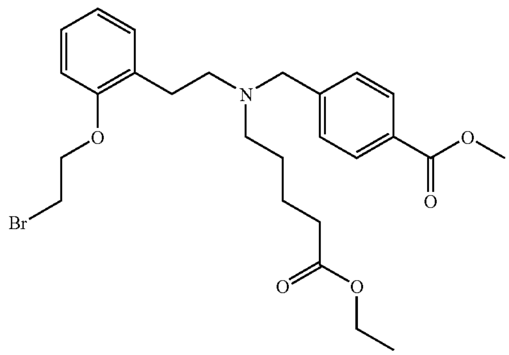 | 519 (M + 1), Rt = 3.65 |
| 109 (from IX and 4-ethylbenzyl chloride by process D) | 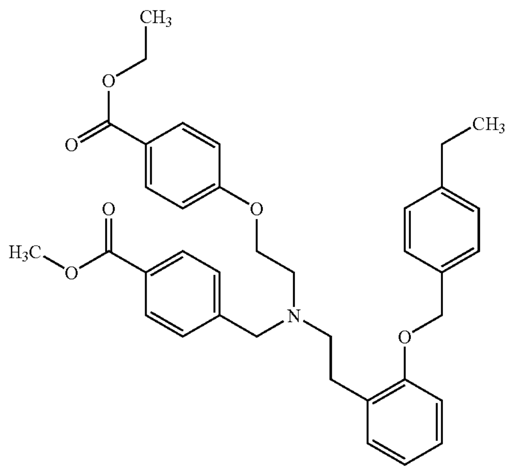 | 1.30 (t, 3H), 1.40 (t, 3H), 2.50 (q, 2H), 2.90 (m, 6H), 3.80 (s, 2H), 3.95 (m, 5H), 4.30 (q, 2H), 4.90 (s, 2H), 6.70-6.90 (m, 4H), 7.10-7.40 (m, 8H), 8.00 (m, 4H). |
| 110 (from IX and 4-butylbenzyl chloride by process D) | 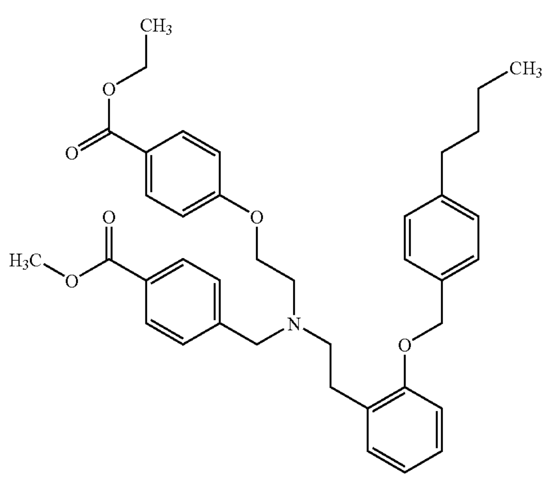 | 1.30 (t, 3H), 1.40 (t, 3H), 1.50 (m, 4H), 2.50 (m, 2H), 2.90 (m, 6H), 3.80 (s, 2H), 3.95 (m, 5H), 4.30 (q, 2H), 4.90 (s, 2H), 6.70-6.90 (m, 4H), 7.10-7.40 (m, 8H), 8.00 (m, 4H). |

-continued

| Example | Structure | Physical data: ¹H-NMR (δ in ppm, selection)[1]) or LC/MS (mass/retention time [min])[2]) |
|---|---|---|
| 111 (from I and 2-[4-(chloro-methyl)phenyl]-5-methyl-1,3-benzoxazole by process D) | 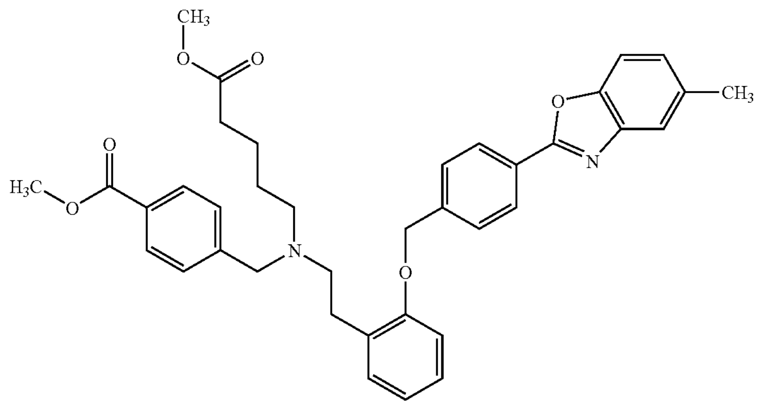 | 1.60 (m, 4H), 2.20 (t, 2H), 2.70 (m, 9H), 3.60 (m, 5H), 3.90 (s, 3H), 5.00 (s, 2H), 6.80-7.60 (m, 11H), 7.90 (d, 2H), 8.10 (d, 2H) |
| 112 (from I and 4-phenylthio-benzyl chloride by process D) | 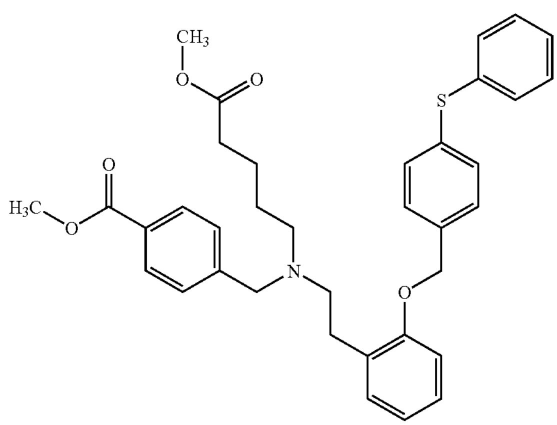 | 1.60 (m, 4H), 2.20 (t, 2H), 2.70 (m, 6H), 3.60 (m, 5H), 3.90 (s, 3H), 5.00 (s, 2H), 6.80-7.60 (m, 15H), 7.90 (d, 2H) |
| 113 (from X and 4-(chloromethyl)-4'-propyl-1,1'-biphenyl by process D) | 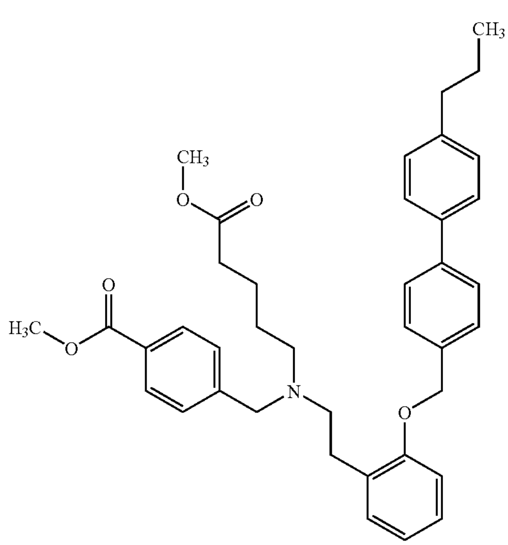 | 1.00 (t, 3H), 1.70 (m, 6H), 2.20 (t, 2H), 2.50 (m, 2H), 2.70 (m, 4H), 2.80 (m, 2H), 3.60 (m, 5H), 3.90 (s, 3H), 5.00 (s, 2H), 6.80-7.60 (m, 14H), 7.90 (d, 2H) |

-continued

| Example | Structure | Physical data: $^1$H-NMR ($\delta$ in ppm, selection)[1] or LC/MS (mass/retention time [min])[2] |
|---|---|---|
| 114 (from I and 4-(chloromethyl)-4'-propyl-1,1'-biphenyl by process D) | 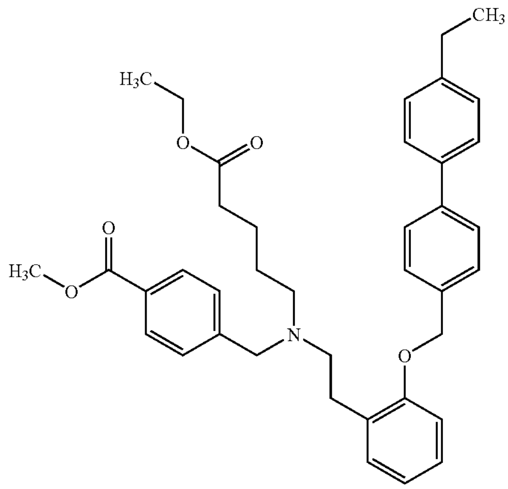 | 1.00 (m, 6H), 1.70 (m, 4H), 2.20 (t, 2H), 2.50 (m, 2H), 2.70 (m, 4H), 2.80 (m, 2H), 3.60 (s, 2H), 3.90 (s, 3H), 4.00 (q, 2H), 5.00 (s, 2H), 6.80-7.60 (m, 14H), 7.90 (d, 2H) |
| 115 (from 114 by process E) | 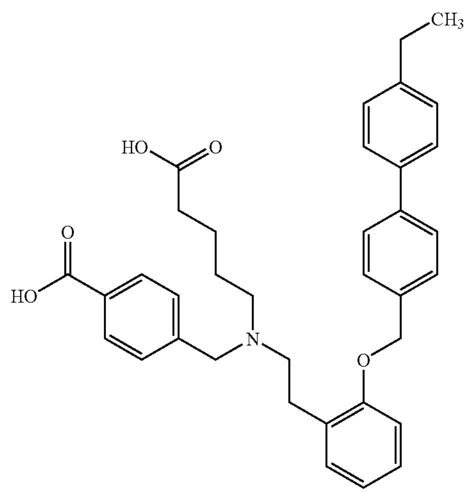 | 1.00 (t, 3H), 1.70 (m, 4H), 2.20 (t, 2H), 2.50-2.80 (m, 8H), 3.60 (s, 2H), 5.00 (s, 2H), 6.80-7.90 (m, 16H) |
| 116 (from 113 by process E) | 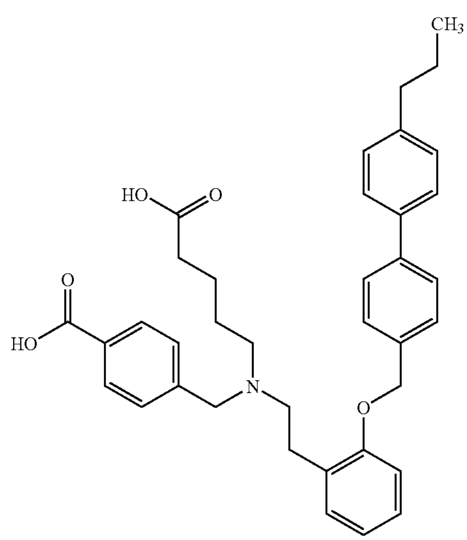 | 1.00 (t, 3H), 1.70 (m, 6H), 2.20 (m, 2H), 2.50-2.80 (m, 8H), 3.40 (s, 2H), 5.00 (s, 2H), 6.80-7.90 (m, 16H), 12.0 (bs, 2H) |

-continued

| Example | Structure | Physical data: $^1$H-NMR (δ in ppm, selection)[1] or LC/MS (mass/retention time [min])[2] |
|---|---|---|
| 117 (from 112 by process E) | 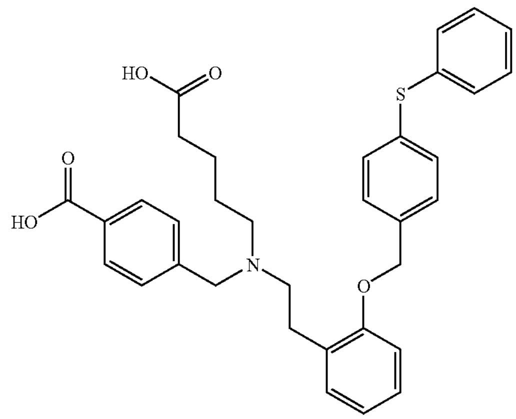 | 1.40 (m, 4H), 2.20 (m, 2H), 2.50-2.80 (m, 6H), 3.40 (s, 2H), 5.00 (s, 2H), 6.80-7.90 (m, 17H) |
| 118 (from 111 by process E) | 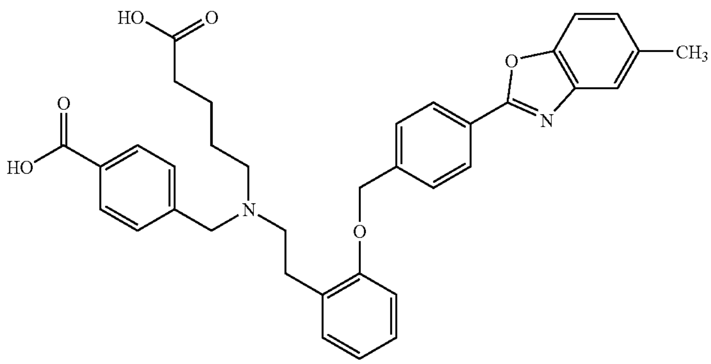 | 1.60 (m, 4H), 2.20 (t, 2H), 2.50 (s, 3H), 3.20 (m, 6H), 4.20 (s, 2H), 5.00 (s, 2H), 6.80-7.60 (m, 11H), 7.90 (d, 2H), 8.10 (d, 2H) |
| 119 (from 109 by process E) | 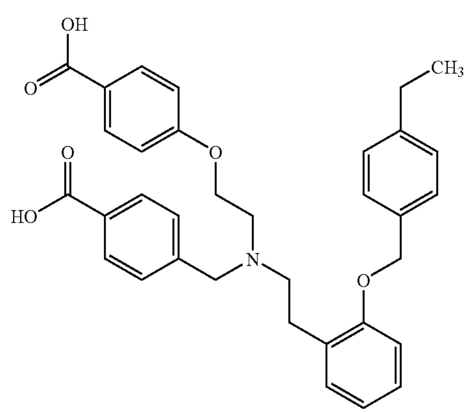 | 1.20 (t, 3H), 2.50 (q, 2H), 3.30 (m, 6H), 4.20 (m, 2H), 4.40 (m, 2H), 4.90 (s, 2H), 6.70-8.00 (m, 16H). |

-continued

| Example | Structure | Physical data: ¹H-NMR ($\delta$ in ppm, selection)[1] or LC/MS (mass/retention time [min])[2] |
|---|---|---|
| 120 (from 110 by process E) | 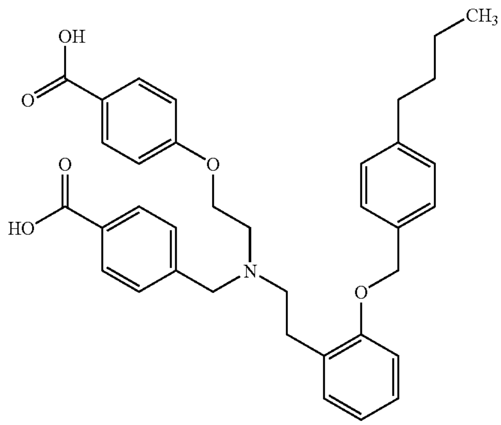 | 1.00 (t, 3H), 1.50 (m, 4H), 2.50 (m, 2H), 3.30 (m, 6H), 4.20 (m, 2H), 4.40 (m, 2H), 5.00 (s, 2H), 6.70-8.00 (m, 16H). |
| 121 (from I and 1-(chloromethyl)-4-[2-(4-fluoro-phenyl)ethyl]-benzene by process D) | 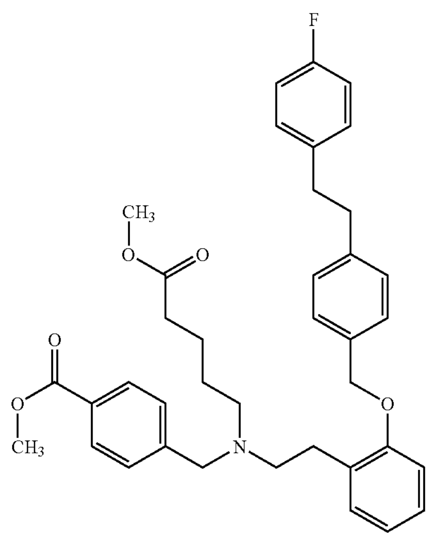 | 1.50 (m, 4H), 2.20 (t, 2H), 2.50 (m, 2H), 2.70 (m, 2H), 2.90 (m, 6H), 3.60 (m, 5H), 3.90 (s, 3H), 5.00 (s, 2H), 6.80-7.60 (m, 14H), 7.90 (d, 2H) |
| 122 (from IX and 4-methoxybenzyl chloride by process D) | 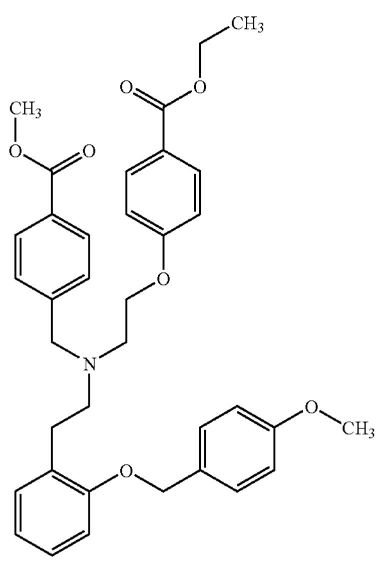 | 1.40 (t, 3H), 2.90 (m, 6H), 3.70 (s, 3H), 3.80 (s, 2H), 3.95 (m, 5H), 4.30 (q, 2H), 4.90 (s, 2H), 6.70-7.40 (m, 12H), 8.00 (m, 4H). |

-continued

| Example | Structure | Physical data: $^1$H-NMR ($\delta$ in ppm, selection)$^{1)}$ or LC/MS (mass/retention time [min])$^{2)}$ |
|---|---|---|
| 123 (from 122 by process E) | 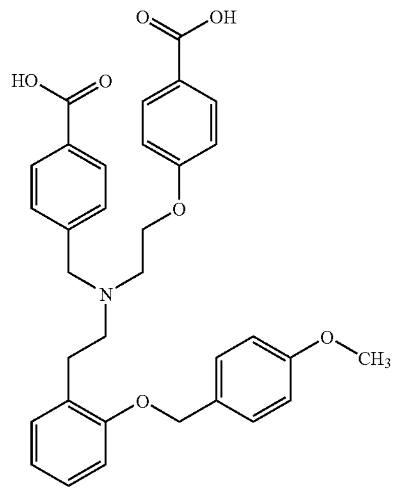 | 3.00 (m, 2H), 3.30 (m, 2H), 3.50 (m, 2H), 3.70 (s, 3H), 4.30 (m, 4H), 4.90 (s, 2H), 6.70-7.40 (m, 12H), 8.00 (m, 4H). |
| 124 (from IX and 4-methoxy-ethoxybenzyl chloride by process D) | 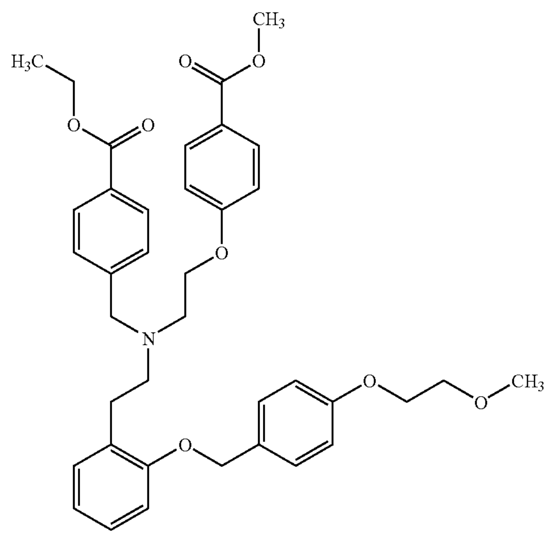 | 1.40 (t, 3H), 2.90 (m, 6H), 3.40 (s, 3H), 3.70-4.10 (m, 11H), 4.30 (q, 2H), 4.90 (s, 2H), 6.70-7.40 (m, 12H), 8.00 (m, 4H). |
| 125 (from 124 by process E) | 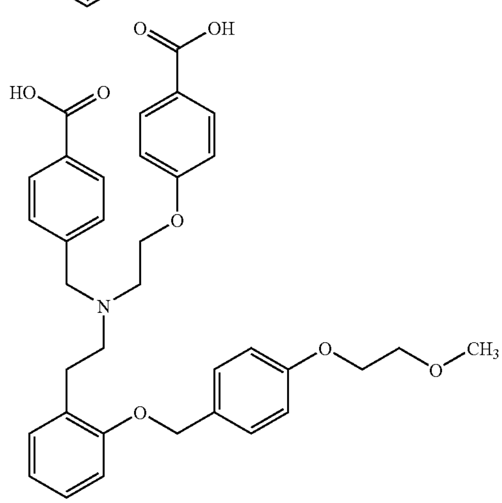 | 3.00 (m, 2H), 3.40 (s, 3H), 3.50 (m, 6H), 4.00 (m, 2H), 4.30 (m, 4H), 4.90 (s, 2H), 6.70-7.40 (m, 12H), 8.00 (m, 4H). |

-continued

| Example | Structure | Physical data: $^1$H-NMR (δ in ppm, selection)$^{1)}$ or LC/MS (mass/retention time [min])$^{2)}$ |
|---|---|---|
| 126 (from 121 by process E) | 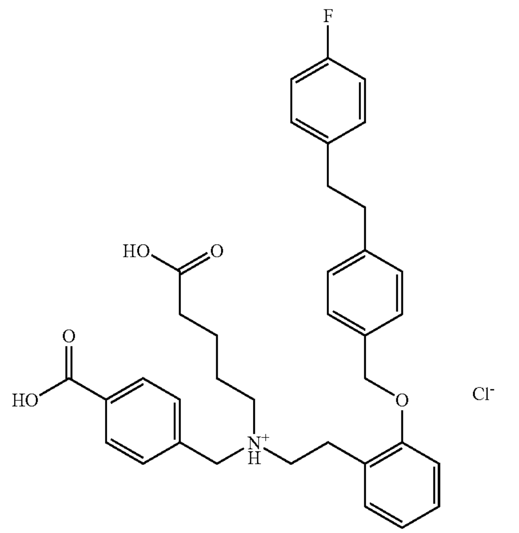 | 1.50 (m, 4H), 2.20 (t, 2H), 3.20 (m, 10H), 4.40 (m, 2H), 5.00 (s, 2H), 6.80-7.60 (m, 14H), 7.90 (d, 2H) |
| 127 (from IX and 4-butoxybenzyl chloride by process D) | 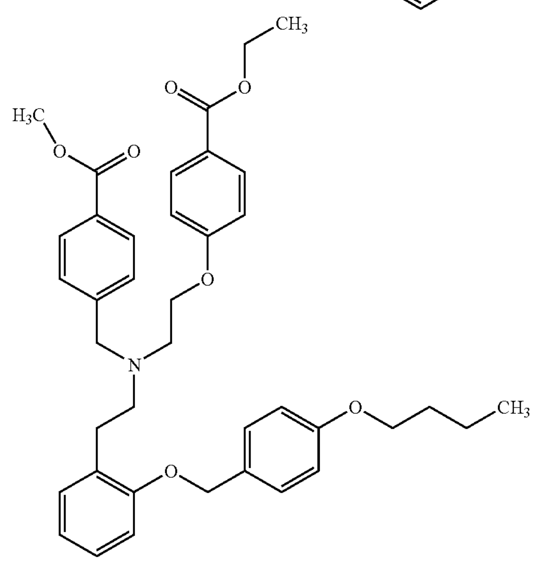 | 1.50 (m, 10H), 2.90 (m, 6H), 3.95 (m, 9H), 4.30 (m, 2H), 4.90 (s, 2H), 6.70-7.40 (m, 12H), 8.00 (m, 4H). |
| 128 (from 127 by process E) | 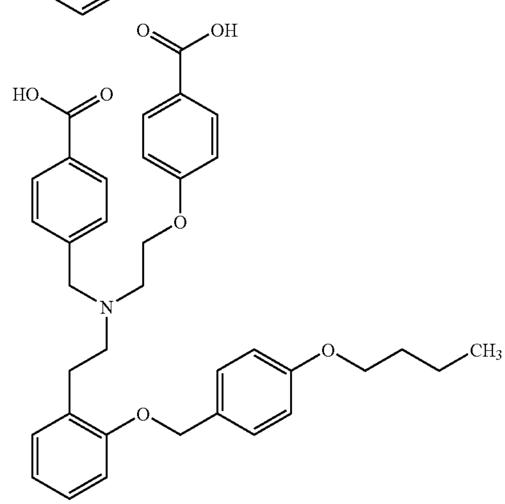 | 1.20 (m, 5H), 1.70 (m, 2H), 3.00 (m, 2H), 3.30 (m, 2H), 3.80 (m, 4H), 4.30 (m, 4H), 4.90 (s, 2H), 6.70-7.40 (m, 12H), 8.00 (m, 4H). |

| Example | Structure | Physical data: ¹H-NMR ($\delta$ in ppm, selection)[1]) or LC/MS (mass/retention time [min])[2]) |
|---|---|---|
| 129 (from IX and 4-isopropylbenzyl chloride by process D) | 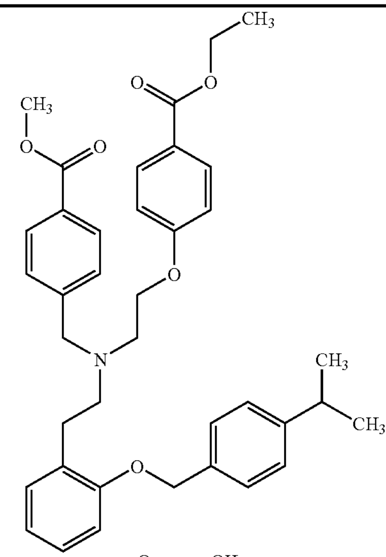 | 1.20 (d, 6H), 1.40 (t, 3H), 2.70 (m, 7H), 3.80 (s, 2H), 3.95 (m, 5H), 4.30 (q, 2H), 4.90 (s, 2H), 6.70-6.90 (m, 4H), 7.10-7.40 (m, 8H), 8.00 (m, 4H). |
| 130 (from 129 by process E) | 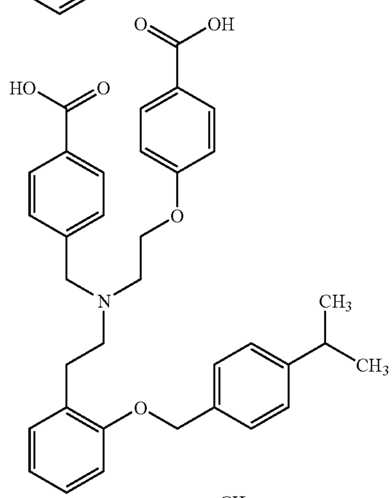 | 1.20 (d, 6H), 2.70 (m, 1H), 3.30 (m, 6H), 4.20 (m, 2H), 4.40 (m, 2H), 4.90 (s, 2H) 6.70-8.00 (m, 16H). |
| 131 (from IX and 4-ethoxybenzyl chloride by process D) | 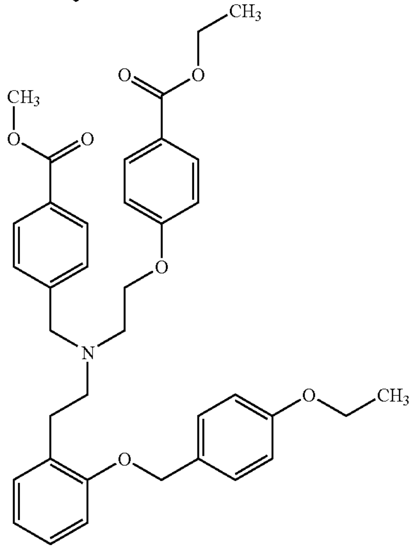 | 1.40 (m, 6H), 2.70 (m, 6H), 3.80 (s, 2H), 3.95 (m, 7H), 4.30 (q, 2H), 4.90 (s, 2H), 6.70-6.90 (m, 4H), 7.10-7.40 (m, 8H), 8.00 (m, 4H). |

-continued

| Example | Structure | Physical data: $^1$H-NMR (δ in ppm, selection)[1)] or LC/MS (mass/retention time [min])[2)] |
|---|---|---|
| 132 (from 131 by process E) | 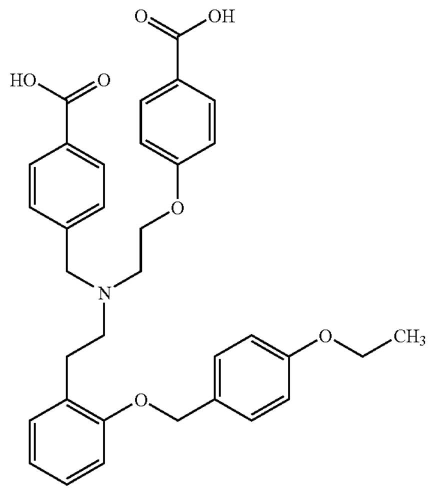 | 1.30 (m, 3H), 2.80 (m, 6H), 4.00 (m, 6H), 4.90 (s, 2H), 6.70-8.00 (m, 16H). |
| 133 (from X and 2-(chloromethyl)-1-benzothiophene by process D) | 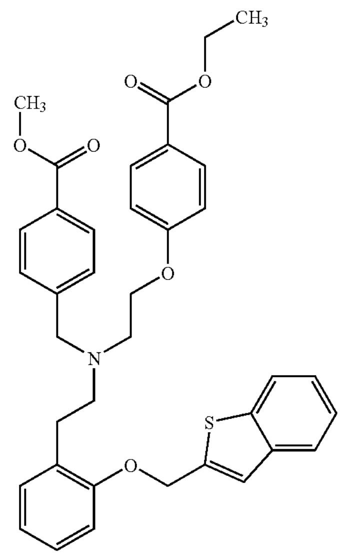 | 624 (M + 1) |
| 134 (from 133 by process E) | 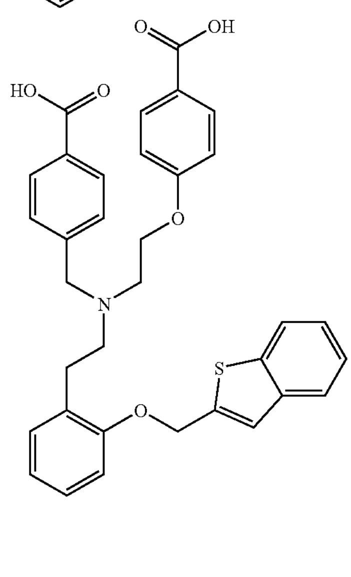 | 582 (M + 1) |

-continued

| Example | Structure | Physical data: $^1$H-NMR (δ in ppm, selection)[1] or LC/MS (mass/retention time [min])[2] |
|---|---|---|
| 135 (from X and 4-bromobenzyl bromide by process D) | 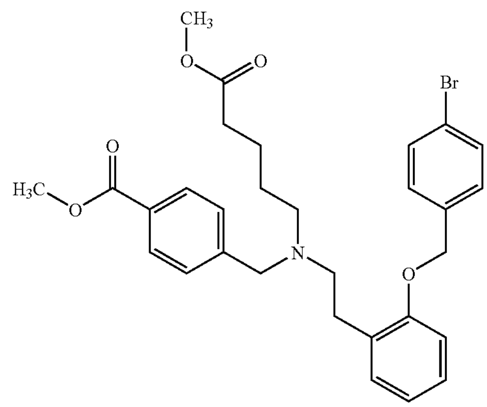 | 1.70 (m, 4H), 2.20 (t, 2H), 2.50 (m, 2H), 2.80 (m, 4H), 3.60 (m, 5H), 3.90 (s, 3H), 5.00 (s, 2H), 6.80-7.60 (m, 10H), 7.90 (d, 2H) |
| 136 (from 135 and 4-methylphenyl-boronic acid by process F) | 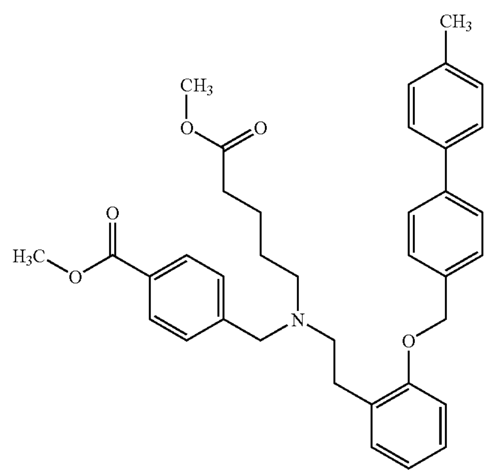 | 580 (M + 1) |
| 137 (from I and 4-(chloromethyl)-4'-trifluoro-methoxyphenyl by process D) | 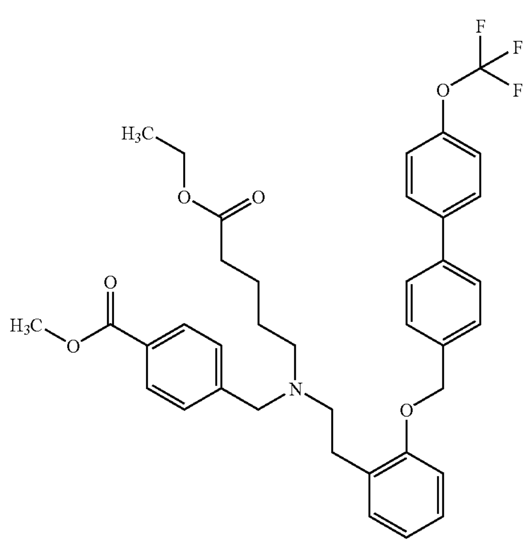 | 1.70 (m, 4H), 2.20 (t, 2H), 2.50 (m, 2H), 2.70 (m, 2H), 2.80 (m, 2H), 3.60 (s, 2H), 3.90 (s, 3H), 4.10 (q, 2H), 5.00 (s, 2H), 6.80-7.60 (m, 14H), 7.90 (d, 2H) |

-continued

| Example | Structure | Physical data: $^1$H-NMR (δ in ppm, selection)[1] or LC/MS (mass/retention time [min])[2] |
|---|---|---|
| 138 (from 137 by process E) | 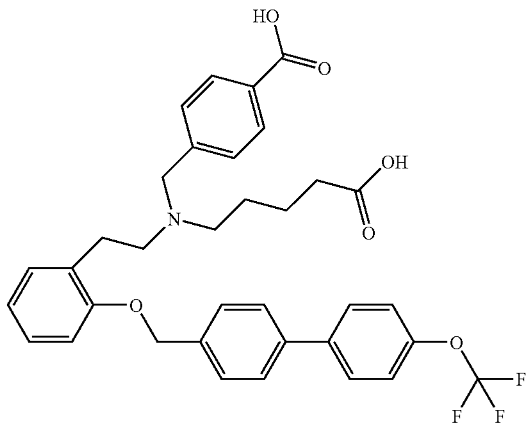 | 1.70 (m, 4H), 2.20-3.00 (m, 8H), 3.60 (s, 2H), 5.00 (s, 2H), 6.80-7.90 (m, 16H), 12.0 (bs, 2H) |
| 139 (from 135 and 1,3-benzodioxol-5-yl-boronic acid by process F) | 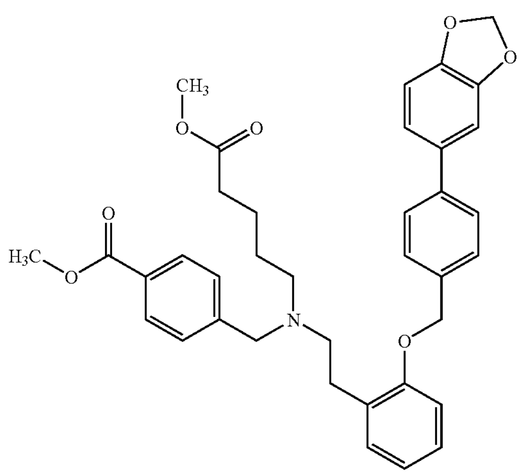 | 610 (M + 1), Rt = 3.51[3] |
| 140 (from 139 by process E) | 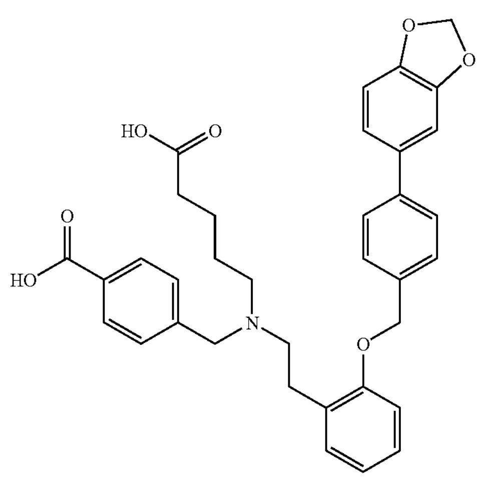 | 582 (M + 1) |

-continued
| Example | Structure | Physical data: $^1$H-NMR (δ in ppm, selection)[1]) or LC/MS (mass/retention time [min])[2]) |
|---|---|---|
| 141 (from 136 by process E) | 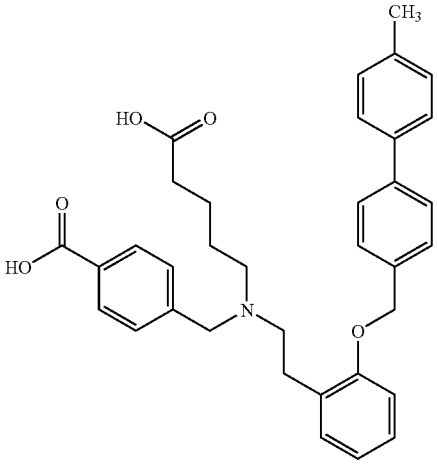 | 552 (M + 1) |
| 142 (from 135 and 4-cyanobenzyl-boronic acid by process F) | 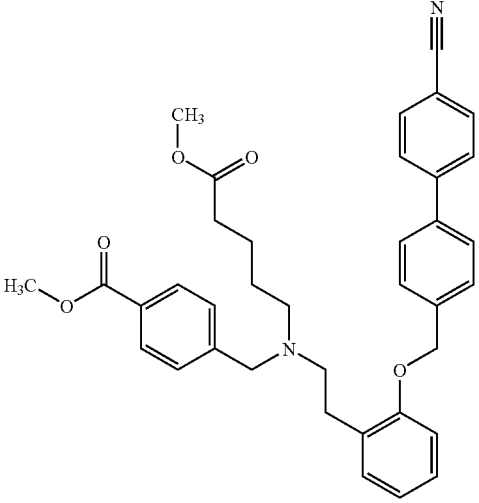 | 591 (M + 1), Rt = 3.42[3]) |
| 143 (from 142 by process E) | 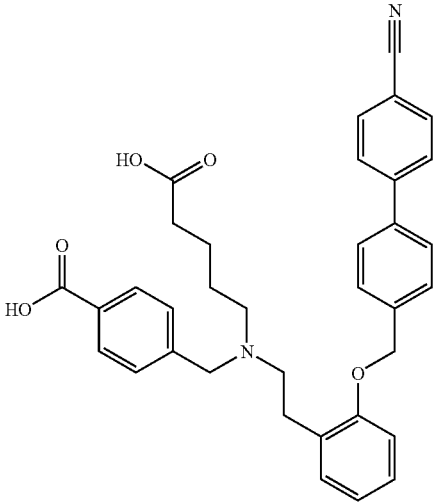 | 563 (M + 1) |

-continued

| Example | Structure | Physical data: $^1$H-NMR ($\delta$ in ppm, selection)$^{1)}$ or LC/MS (mass/retention time [min])$^{2)}$ |
|---|---|---|
| 144 (from I and 4-(chloromethyl)-4'-methyloxy-ethoxythoxy-phenyl by process D) | 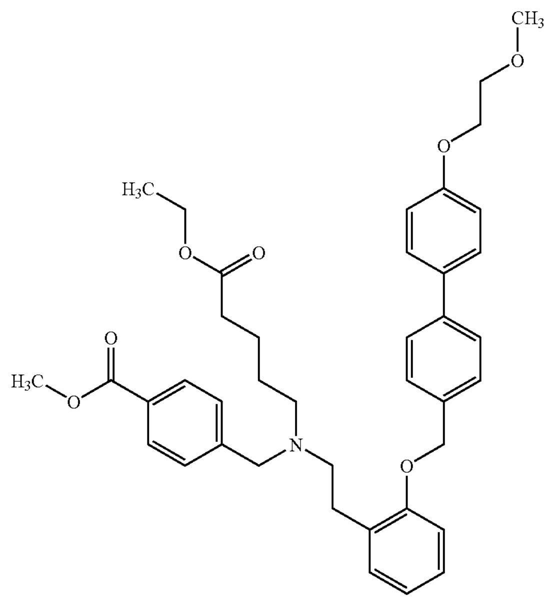 | 1.70 (m, 4H), 2.20 (t, 2H), 2.50 (m, 2H), 2.70 (m, 2H), 2.80 (m, 2H), 3.40 (s, 3H), 3.60 (s, 2H), 3.70 (m, 2H), 3.90 (s, 3H), 4.10 (q, 2H), 4.20 (m, 2H), 5.00 (s, 2H), 6.80-8.00 (m, 16H) |
| 145 (from 144 by process E) | 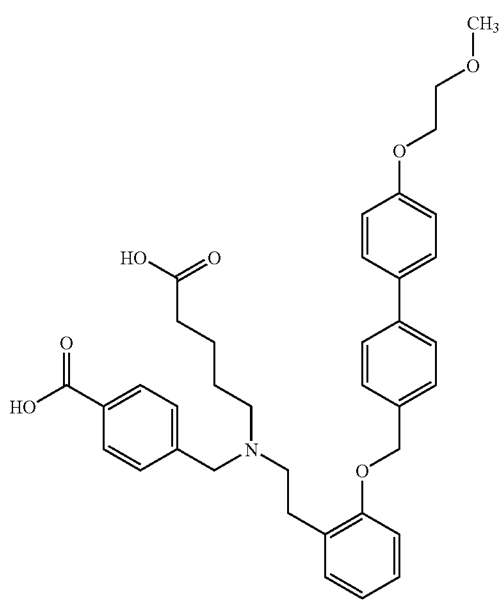 | 1.70 (m, 4H), 2.20 (m, 2H), 3.00-3.50 (m, 11H), 3.70 (m, 2H), 4.20 (m, 2H), 5.00 (s, 2H), 6.80-7.90 (m, 16H) |

-continued

| Example | Structure | Physical data: ¹H-NMR (δ in ppm, selection)[1] or LC/MS (mass/retention time [min])[2] |
|---|---|---|
| 146 (from 135 and 4-trifluoromethylphenylboronic acid by process F) | | 1.60 (m, 4H), 2.20 (t, 2H), 2.50 (m, 2H), 2.70 (m, 2H), 2.80 (m, 2H), 3.60 (m, 5H), 3.90 (s, 3H), 5.00 (s, 2H), 6.80-7.60 (m, 14H), 7.90 (d, 2H) |
| 147 (from 146 by process E) | | 1.60 (m, 4H), 2.20 (t, 2H), 3.10 (m, 4H), 3.30 (m, 2H), 4.80 (s, 2H), 5.00 (s, 2H), 6.80-7.80 (m, 14H), 8.00 (d, 2H) |
| 148 (from I and 2-[4-(chloromethyl)phenyl]-5-methylpyridine by process D) | | 1.20 (t, 3H), 1.60 (m, 4H), 2.20 (t, 2H), 2.40 (s, 3H), 2.50 (m, 2H), 2.70 (m, 2H), 2.80 (m, 2H), 3.60 (s, 2H), 3.90 (s, 3H), 4.10 (q, 2H), 5.00 (s, 2H), 6.80-7.60 (m, 10H), 7.90 (m, 4H), 8.50 (m, 1H) |

-continued

| Example | Structure | Physical data: $^1$H-NMR (δ in ppm, selection)[1] or LC/MS (mass/retention time [min])[2] |
|---|---|---|
| 149 (from 148 by process E) | 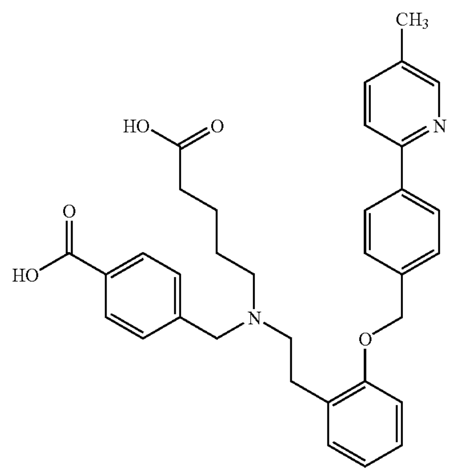 | 553 (M + 1), Rt = 2.29 |
| 150 (from 135 and 2,4-difluoro-phenylboronic acid by process F) | 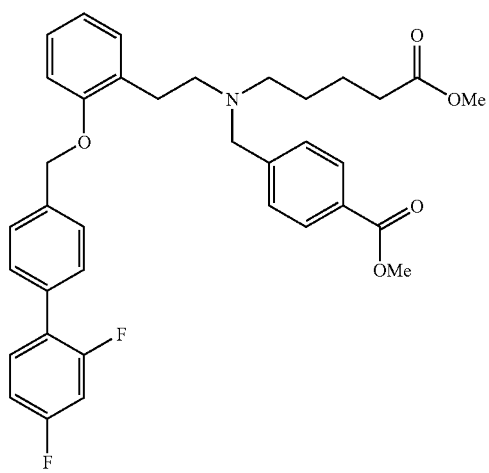 | 1.60 (m, 4H), 2.20 (t, 2H), 2.50 (m, 2H), 2.70 (m, 2H), 2.80 (m, 2H), 3.60 (m, 5H), 3.90 (s, 3H), 5.00 (s, 2H), 6.80-7.60 (m, 13H), 7.90 (m, 2H) |
| 151 (from 150 by process E) | 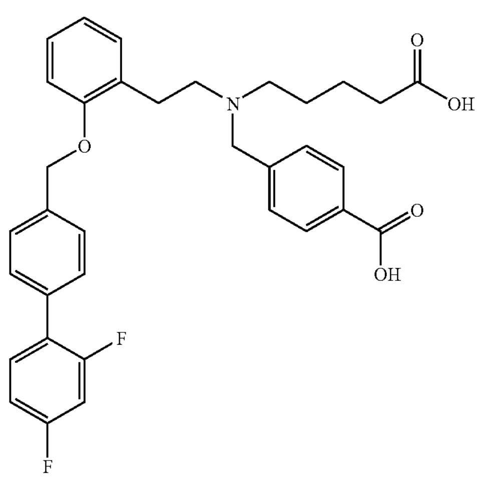 | 574 (M + 1), Rt = 3.24 |

-continued

| Example | Structure | Physical data: ¹H-NMR (δ in ppm, selection)[1] or LC/MS (mass/retention time [min])[2] |
|---|---|---|
| 152 (from 135 and 4-ethoxyphenyl-boronic acid by process F) | 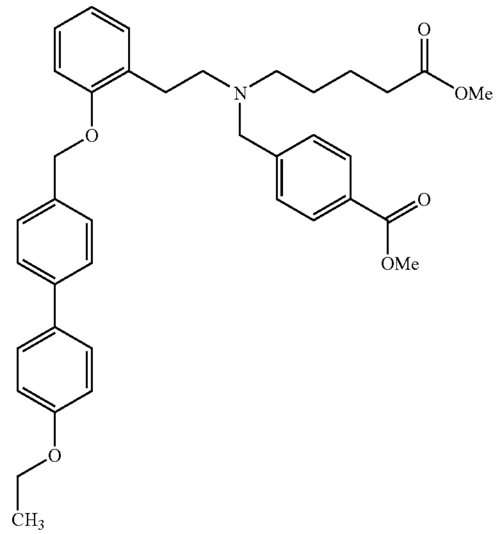 | 1.60 (m, 7H), 2.20 (t, 2H), 2.50 (m, 2H), 2.70 (m, 2H), 2.80 (m, 2H), 3.60 (m, 5H), 3.90 (s, 3H), 4.10 (q, 2H), 5.00 (s, 2H), 6.80-7.60 (m, 14H), 7.90 (m, 2H) |
| 153 (from 152 by process E) | 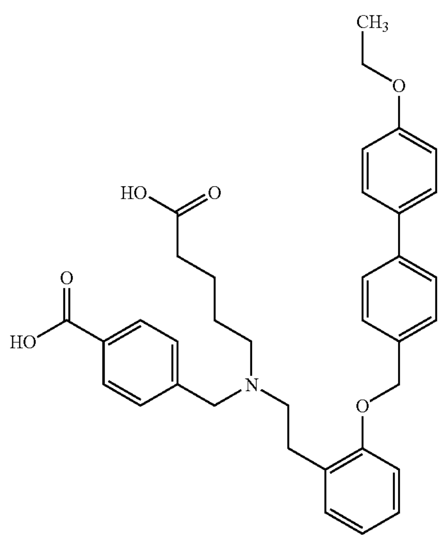 | 1.50 (m, 7H), 2.20 (t, 2H), 3.40 (m), 4.10 (q, 2H), 4.50 (m, 2H), 5.00 (s, 2H), 6.70-7.80 (m, 14H), 8.00 (d, 2H) |
| 154 (from 135 and 3-cyanophenyl boronic acid by process F) | 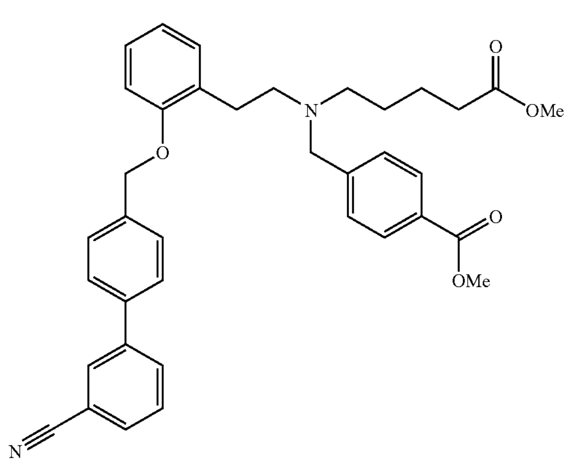 | 1.60 (m, 4H), 2.20 (t, 2H), 2.50 (m, 2H), 2.70 (m, 2H), 2.80 (m, 2H), 3.60 (m, 5H), 3.90 (s, 3H), 5.00 (s, 2H), 6.70-8.20 (m, 16H) |

-continued

| Example | Structure | Physical data: $^1$H-NMR (δ in ppm, selection)$^{1)}$ or LC/MS (mass/retention time [min])$^{2)}$ |
|---|---|---|
| 155 (from 154 by process E) | 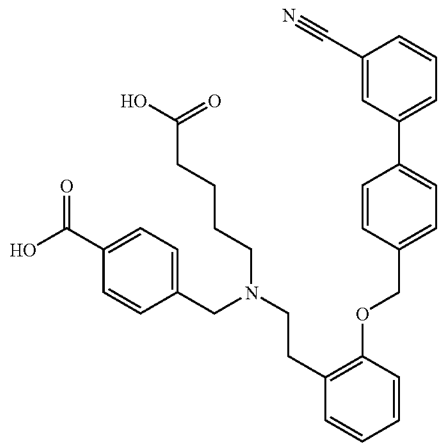 | 1.50 (m, 4H), 2.20 (m, 2H), 3.40 (m), 4.50 (m, 2H), 5.00 (s, 2H), 6.70-8.20 (m, 16H) |
| 156 (from 135 and 3,5-difluoro-phenylboronic acid by process F) | 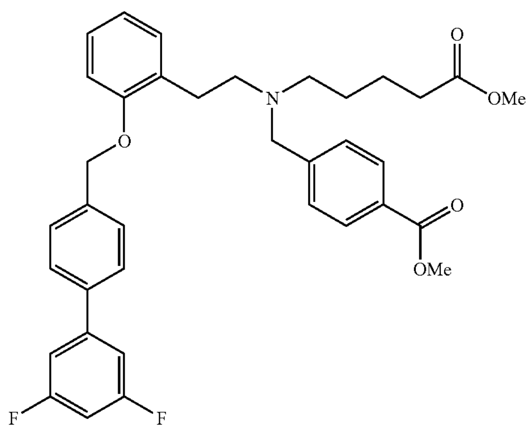 | 1.50 (m, 4H), 2.20 (t, 2H), 2.50 (m, 2H), 2.70 (m, 2H), 2.80 (m, 2H), 3.60 (m, 5H), 3.90 (s, 3H), 5.00 (s, 2H), 6.80-7.60 (m, 13H), 7.90 (m, 2H) |
| 157 (from 156 by process E) | 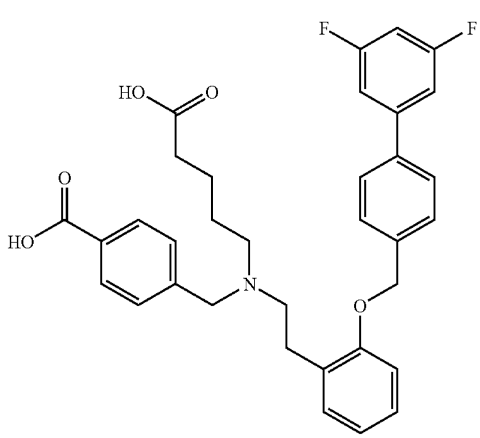 | 1.50 (m, 4H), 2.20 (m, 2H), 3.40 (m), 4.50 (m, 2H), 5.00 (s, 2H), 6.70-8.20 (m, 15H) |

-continued

| Example | Structure | Physical data: ¹H-NMR (δ in ppm, selection)¹⁾ or LC/MS (mass/retention time [min])²⁾ |
|---|---|---|
| 158 (from 135 and 4-tert-butyl-phenylboronic acid by process F) | 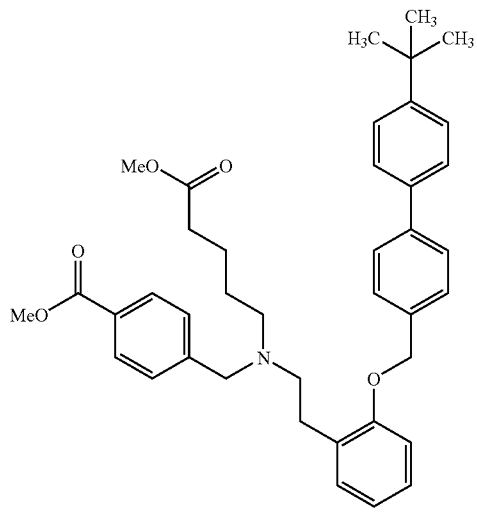 | 1.40 (s, 9H), 1.50 (m, 4H), 2.20 (t, 2H), 2.50 (m, 2H), 2.70 (m, 2H), 2.80 (m, 2H), 3.60 (m, 5H), 3.90 (s, 3H), 5.00 (s, 2H), 6.80-7.60 (m, 14H), 7.90 (m, 2H) |
| 159 (from 158 by process E) | 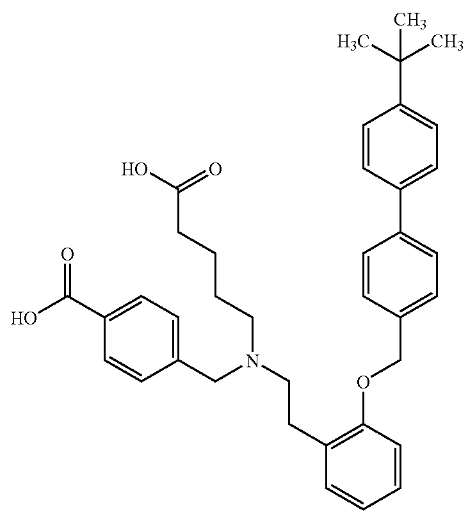 | 1.30 (s, 9H), 1.50 (m, 4H), 2.20 (m, 2H), 3.40 (m), 4.50 (m, 2H), 5.00 (s, 2H), 6.70-8.20 (m, 16H) |
| 160 (from 135 and 2,3-difluoro-phenylboronic acid by process F) | 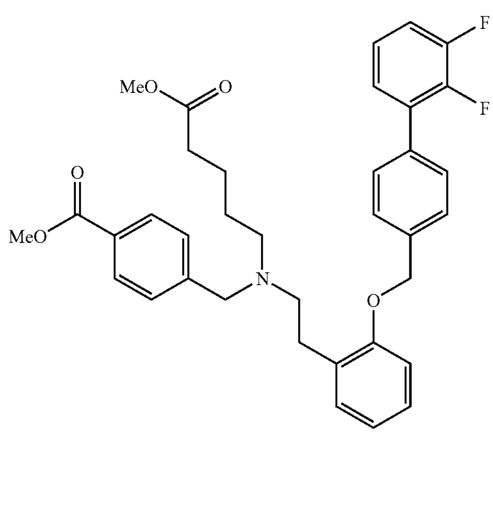 | 602 (M + 1), Rt = 3.56³⁾ |

-continued

| Example | Structure | Physical data: $^1$H-NMR (δ in ppm, selection)$^{1)}$ or LC/MS (mass/retention time [min])$^{2)}$ |
|---|---|---|
| 161 (from 160 by process E) | 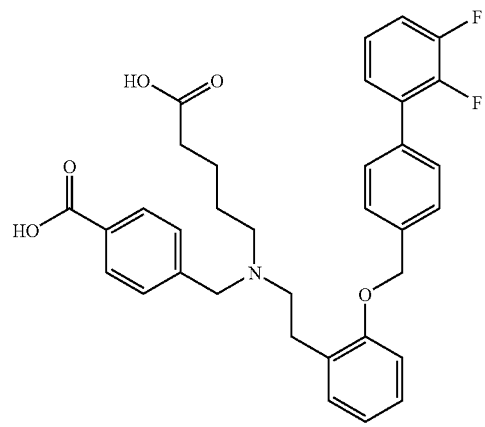 | 1.50 (m, 4H), 2.00-3.50 (m), 4.50 (m, 2H), 5.00 (s, 2H), 6.70-8.20 (m, 15H) |
| 162 (from X and 2-(3-chloropropyl)-1,3-benzoxazole by process D) | 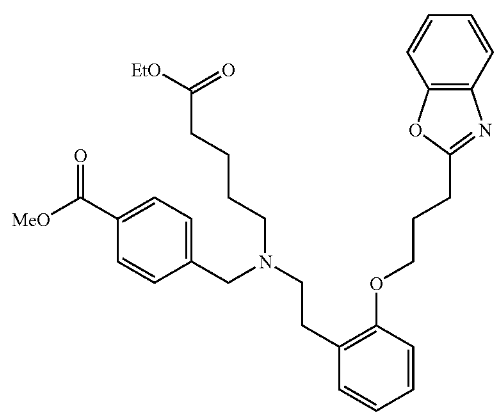 | 1.40 (t, 3H), 1.50 (m, 6H), 2.20-2.80 (m, 10H), 3.60 (m, 2H), 3.90 (s, 3H), 4.10 (m, 4H), 6.80-8.00 (m, 12H) |
| 163 (from 162 by process E) | 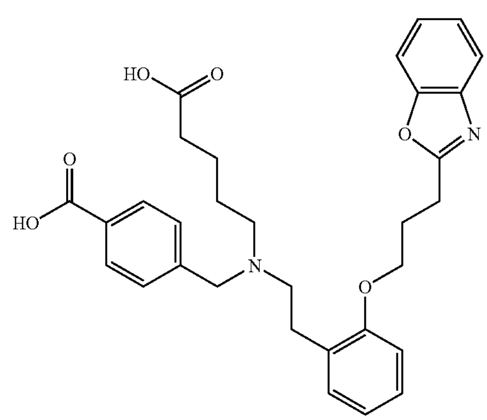 | 531 (M + 1), Rt = 2.95$^{3)}$ |

-continued
| Example | Structure | Physical data: ¹H-NMR (δ in ppm, selection)[1] or LC/MS (mass/retention time [min])[2] |
|---|---|---|
| 164 (from X and 4-tert-butyl-2,6-dimethyl-benzyl chloride by process D) | 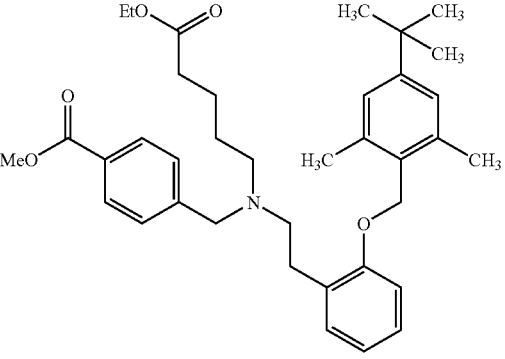 | 1.40 (m, 16H), 2.10 (m, 2H), 2.30 (m, 8H), 2.60 (m, 4H), 2.80 (m), 3.50 (s, 2H), 3.90 (s, 3H), 4.10 (q, 2H), 5.00 (s, 2H), 6.90-7.40 (m, 8H), 7.90 (d, 2H) |
| 165 (from 164 by process E) | 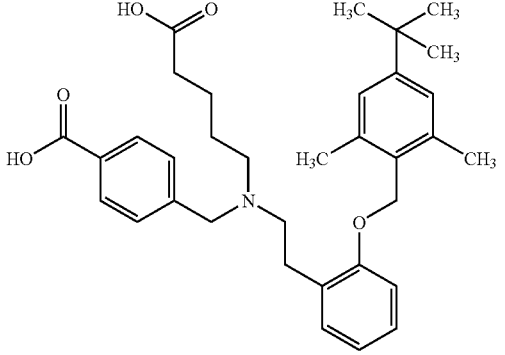 | 1.30 (s, 9H), 1.50 (m, 4H), 2.10 (m, 2H), 2.30 (s, 6H), 2.80 (m), 3.90 (s, 2H), 5.00 (s, 2H), 6.90-7.40 (m, 8H), 7.90 (d, 2H) |
| 166 (from X and 2-[4-(chloro-methyl)phenyl]-1,3-benzoxazole by process D) | 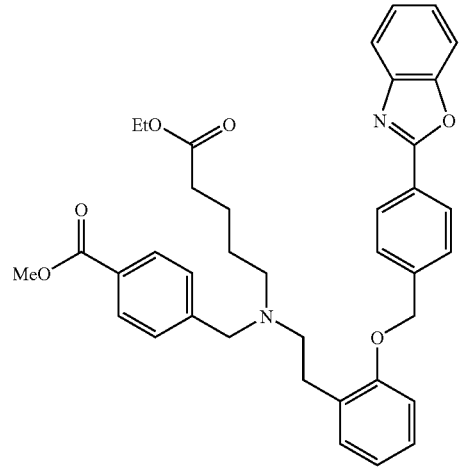 | 1.20 (t, 3H), 1.50 (m, 4H), 2.20 (t, 2H), 2.50 (m, 2H), 2.70 (m, 2H), 2.80 (m, 2H), 3.60 (s, 2H), 3.90 (s, 3H), 4.10 (q, 2H), 5.00 (s, 2H), 6.80-7.80 (m, 12H), 7.90 (d, 2H), 8.10 (d, 2H) |

-continued

| Example | Structure | Physical data: $^1$H-NMR (δ in ppm, selection)[1] or LC/MS (mass/retention time [min])[2] |
|---|---|---|
| 167 (from 166 by process E) | 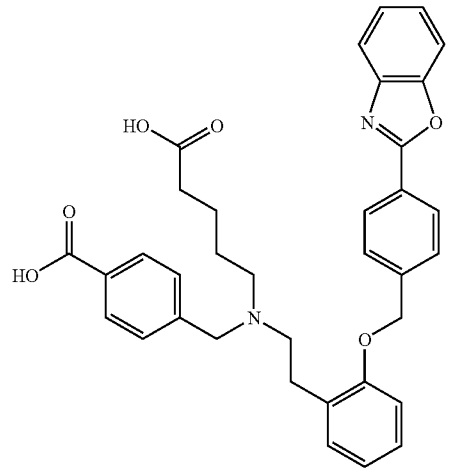 | 579 (M + 1), Rt = 3.42 |
| 168 (from X and 2-(3-chlorobutyl)-1,3-benzoxazole by process D) | 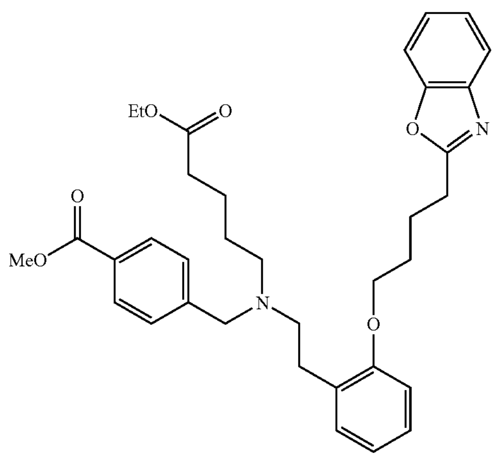 | 587 (M + 1), Rt = 3.44[3] |
| 169 (from 168 by process E) | 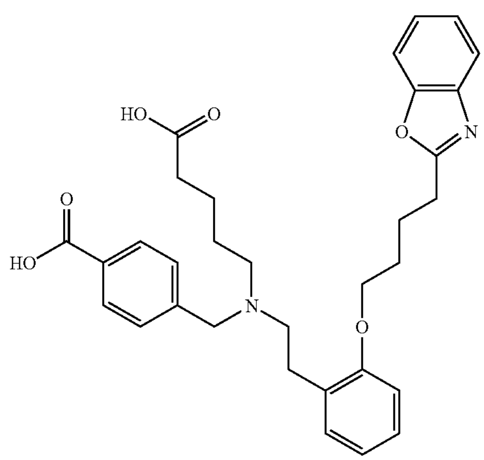 | 545 (M + 1), Rt = 3.19 |

-continued

| Example | Structure | Physical data: $^1$H-NMR (δ in ppm, selection)[1] or LC/MS (mass/retention time [min])[2] |
|---|---|---|
| 170 (from X and (bromomethyl)-cyclohexane by process D) | 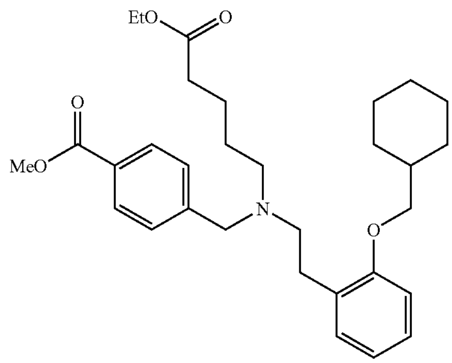 | 1.00-1.70 (m, 18H), 2.20 (t, 2H), 2.50 (t, 2H), 2.70 (m, 2H), 2.80 (m, 2H), 3.70 (m, 4H), 3.80 (s, 3H), 4.10 (q, 2H), 6.80 (m, 2H), 7.20 (m, 2H), 7.30 (d, 2H), 7.90 (d, 2H) |
| 171 (from 170 by process E) | 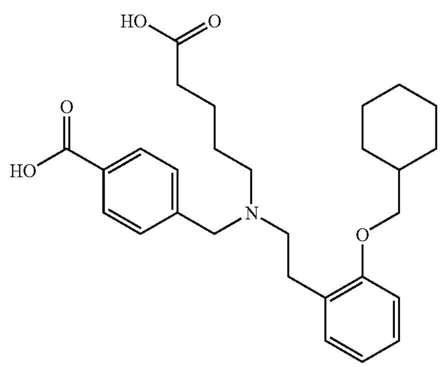 | 1.00 (m, 2H), 1.30 (m, 4H), 1.70 (m, 9H), 2.20 (t, 2H), 2.40 (t, 2H), 3.00 (m, 2H), 3.20 (m, 2H), 3.70 (d, 2H), 6.80 (m, 2H), 7.20 (m, 2H), 7.60 (d, 2H), 8.10 (d, 2H) |
| 172 (from X and (bromoethyl)-cyclohexane by process D) | 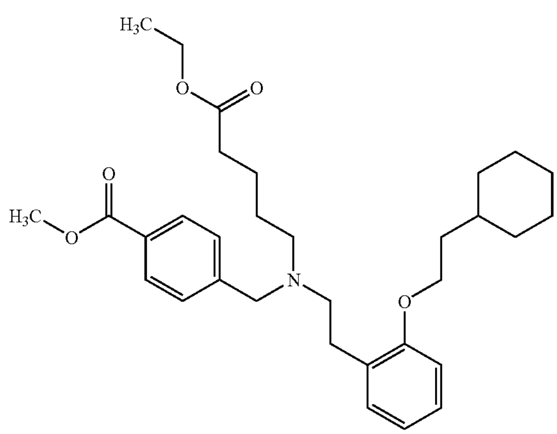 | 1.00-1.70 (m, 20H), 2.20 (t, 2H), 2.50 (t, 2H), 2.70 (m, 2H), 2.80 (m, 2H), 3.60 (s, 2H), 3.90 (m, 5H), 4.10 (q, 2H), 6.80 (m, 2H), 7.20 (m, 2H), 7.30 (d, 2H), 7.90 (d, 2H) |
| 173 (from 172 by process E) | 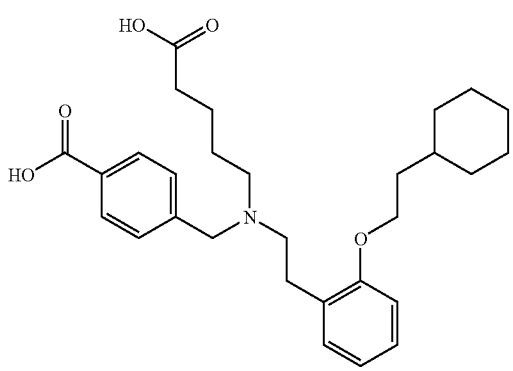 | 1.00 (m, 2H), 1.20 (m, 2H), 1.40 (m, 1H), 1.70 (m, 10H), 1.90 (m, 2H), 2.40 (t, 2H), 3.00 (m, 2H), 3.20 (m, 4H), 4.00 (t, 2H), 4.50 (s, 2H), 6.80 (m, 2H), 7.20 (m, 2H), 7.60 (d, 2H), 8.10 (d, 2H) |

-continued

| Example | Structure | Physical data: <br>$^1$H-NMR ($\delta$ in ppm, selection)[1] or LC/MS (mass/retention time [min])[2] |
|---|---|---|
| 174 <br>(from X and (bromopropyl)-cyclohexane by process D) | | 0.80-1.70 (m, 22H), 2.20 (t, 2H), 2.50 (t, 2H), 2.70 (m, 2H), 2.80 (m, 2H), 3.60 (s, 2H), 3.90 (m, 5H), 4.10 (q, 2H), 6.80 (m, 2H), 7.20 (m, 2H), 7.30 (d, 2H), 7.90 (d, 2H) |
| 175 <br>(from 174 by process E) | | 1.00 (m, 2H), 1.30 (m, 7H), 1.70 (m, 8H), 1.90 (m, 2H), 2.40 (t, 2H), 3.10 (m, 2H), 3.20 (m, 4H), 3.90 (t, 2H), 4.50 (s, 2H), 6.80 (m, 2H), 7.20 (m, 2H), 7.60 (d, 2H), 8.10 (d, 2H) |
| 176 <br>(from X and nonyl bromide by process D) | | 0.80 (t, 3H), 1.20-1.70 (m, 21H), 2.20 (t, 2H), 2.50 (t, 2H), 2.70 (m, 2H), 2.80 (m, 2H), 3.60 (s, 2H), 3.90 (m, 5H), 4.10 (q, 2H), 6.80 (m, 2H), 7.20 (m, 2H), 7.30 (d, 2H), 7.90 (d, 2H) |

-continued
| Example | Structure | Physical data: $^1$H-NMR (δ in ppm, selection)[1] or LC/MS (mass/retention time [min])[2] |
|---|---|---|
| 177 (from 176 by process E) | 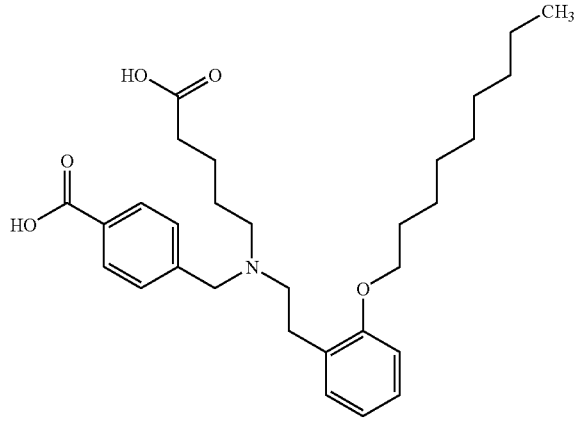 | 0.90 (t, 3H), 1.30 (m, 12H), 1.70 (m, 4H), 1.90 (m, 2H), 2.40 (t, 2H), 3.10 (m, 2H), 3.20 (m, 4H), 3.90 (t, 2H), 4.50 (s, 2H), 6.80 (m, 2H), 7.20 (m, 2H), 7.60 (d, 2H), 8.10 (d, 2H) |
| 178 (from X and 5-methylhexyl-bromide by process D) | 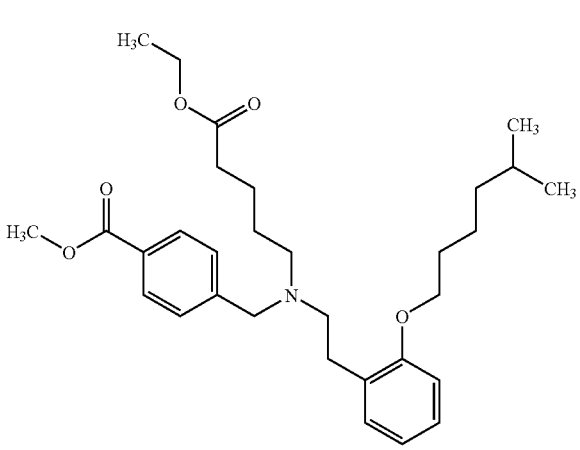 | 0.90 (d, 6H), 1.10-1.70 (m, 14H), 2.20 (t, 2H), 2.50 (t, 2H), 2.70 (m, 2H), 2.80 (m, 2H), 3.60 (s, 2H), 3.90 (m, 5H), 4.10 (q, 2H), 6.80 (m, 2H), 7.20 (m, 2H), 7.30 (d, 2H), 7.90 (d, 2H) |
| 179 (from 178 by process E) | 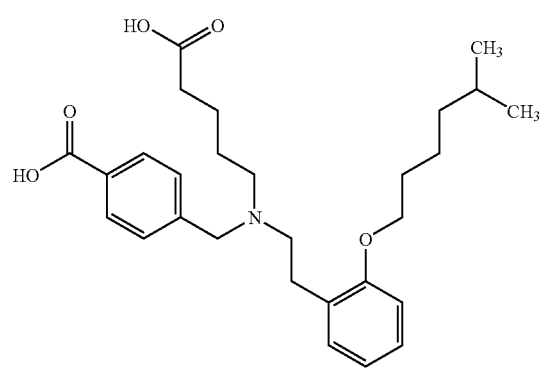 | 0.90 (d, 6H), 1.20 (m, 2H), 1.40 (m, 2H), 1.60 (m, 1H), 1.70 (m, 4H), 1.90 (m, 2H), 2.40 (t, 2H), 3.10 (m, 2H), 3.20 (m, 4H), 3.90 (t, 2H), 4.50 (s, 2H), 6.80 (m, 2H), 7.20 (m, 2H), 7.60 (d, 2H), 8.10 (d, 2H) |

-continued

| Example | Structure | Physical data: ¹H-NMR ($\delta$ in ppm, selection)[1] or LC/MS (mass/retention time [min])[2] |
|---|---|---|
| 180 (from XI and 1-(chloromethyl)-4-(2-phenyl-ethyl)benzene by process D) | 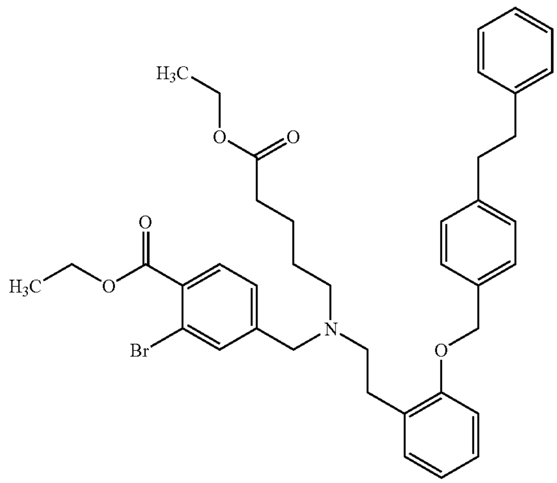 | 1.50 (m, 8H), 2.20 (t, 2H), 2.50 (m, 2H), 2.60-3.00 (m, 8H), 3.60 (s, 2H), 4.10 (q, 2H), 4.40 (q, 2H), 5.00 (s, 2H), 6.80-7.60 (m, 14H), 7.60 (m, 2H) |
| 181 (from XII and 4-(chloromethyl)-4'-methoxy-1,1'-biphenyl by process D) | 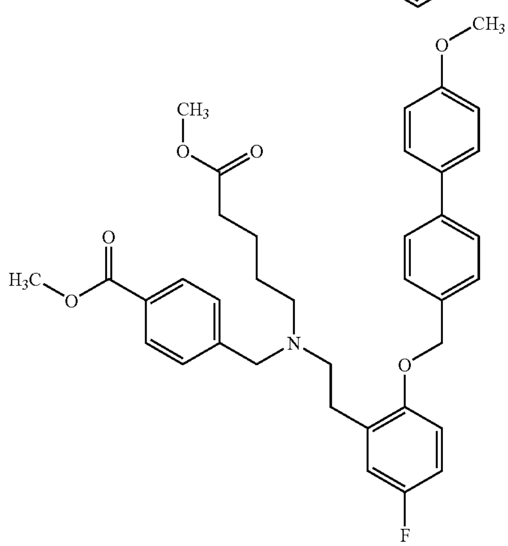 | 1.00 (m, 4H), 2.20 (t, 2H), 2.50 (m, 2H), 2.70 (m, 4H), 2.80 (m, 2H), 3.60 (m, 5H), 3.90 (s, 3H), 3.95 (s, 3H), 5.00 (s, 2H), 6.80-7.00 (m, 5H), 7.40 (m, 4H), 7.50 (m, 4H), 7.90 (d, 2H) |
| 182 (from 181 by process E) | 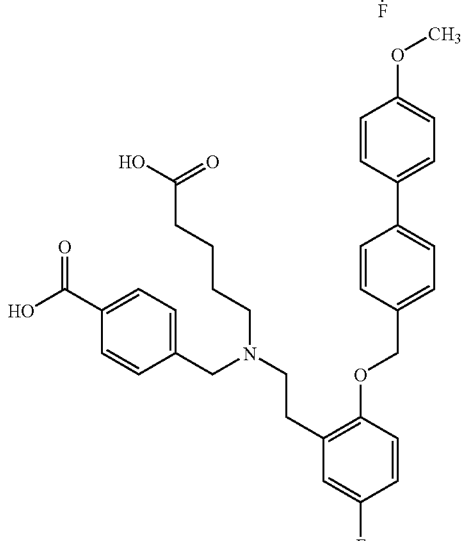 | 1.60 (m, 4H), 2.20 (t, 2H), 3.00 (m, 6H), 3.80 (s, 3H), 4.20 (s, 2H), 5.00 (s, 2H), 6.80-7.00 (m, 5H), 7.50 (m, 8H), 8.00 (d, 2H) |

| Example | Structure | Physical data: ¹H-NMR (δ in ppm, selection)[1] or LC/MS (mass/retention time [min])[2] |
|---|---|---|
| 183 (from XIII and methyl 5-bromo-valerate analogously to I.2) | 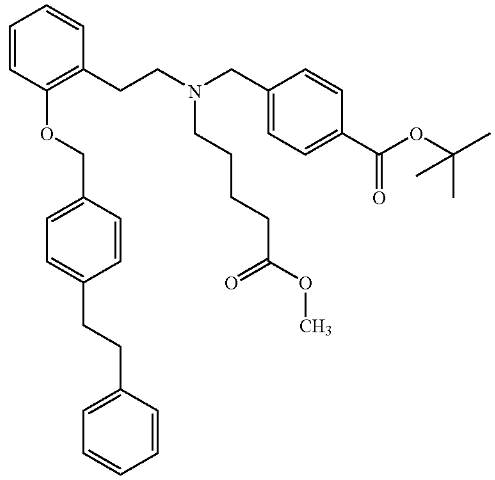 | 1.50 (m, 13H), 2.20 (t, 2H), 2.50 (m, 2H), 2.60-3.00 (m, 8H), 3.60 (m, 5H), 4.40 (q, 2H), 5.00 (s, 2H), 6.80-7.60 (m, 15H), 7.80 (m, 2H) |
| 184 (from 183 using trifluoroacetic acid) | 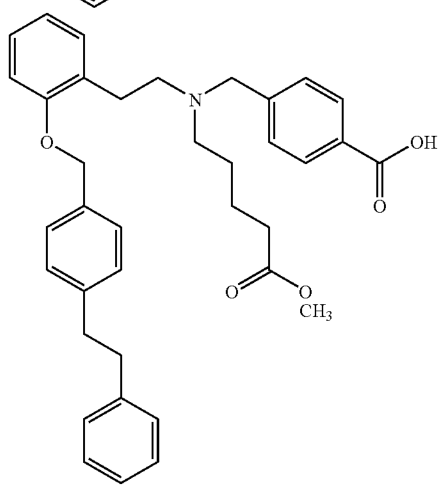 | 580 (M + 1), Rt = 3.87 |

[1] NMR conditions: d6-DMSO, 300 MHz
[2] LC/MS conditions: column: Symmetry C18 2.1 * 150 mm; mobile phase acetonitrile/0.6 g of HCl 30% strength/H₂O; gradient: 10% acetonitrile to 90% acetonitrile; flow rate: 0.6 ml/min; detector: UV 210 nm
[3] LC/MS conditions: column: Symmetry C18 2.1 * 150 mm; mobile phase: acetonitrile/H₂O (0.1% formic acid); gradient: 10% acetonitrile to 90% acetonitrile; flow rate: 0.5 ml/min; detector: UV 210 nm

Example 185

Methyl 4-{[(2-{5-fluoro-2-[(4'-methyl-1,1'-biphenyl-4-yl)methoxy]phenyl}ethyl)(5-methoxy-5-oxopentyl)amino]methyl}benzoate

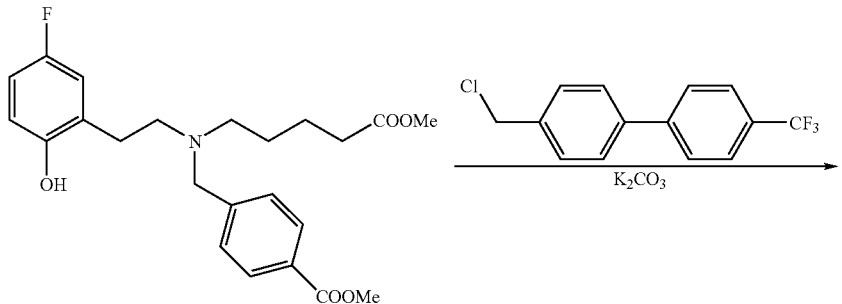

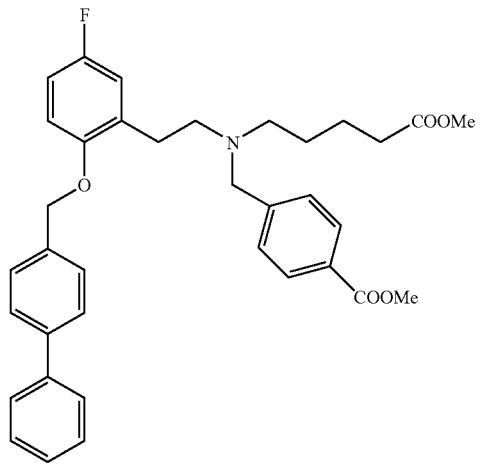

447 mg (0.93 mmol) of methyl 4-({(5-methoxy-5-oxopentyl)[2-(5-fluoro-2-hydroxyphenyl)ethyl]amino}methyl)benzoate from Ex. XII and 277 mg (1.02 mmol) of 4-(chloromethyl)-4'-(trifluoromethyl)-1,1'-biphenyl are dissolved in 10 ml of acetonitrile. 455 mg (1.40 mmol) of caesium carbonate and a spatula tip of potassium iodide are added, and the mixture is heated at reflux for 48 hours. The suspension is filtered and concentrated and the residue is chromatographed over silica gel using cyclohexane:ethyl acetate (5:1).

Yield: 447 mg (73.6% of theory)

$^1$H-NMR (d6-DMSO, 300 MHz): 1.00 (m, 4H), 2.20 (t, 2H), 2.50 (m, 2H), 2.70 (m, 4H), 2.80 (m, 2H), 3.60 (m, 5H), 3.90 (s, 3H), 5.00 (s, 2H), 6.80-7.00 (m, 3H), 7.30 (d, 4H), 7.40 (d, 2H), 7.50 (d, 2H), 7.70 (m, 4H), 7.90 (d, 2H).

Example 186

4-{[(4-Carboxybutyl)(2-{5-fluoro-2-[(4'-methyl-1,1'-biphenyl-4-yl)-methoxy]phenyl}ethyl)amino]methyl}benzoic Acid

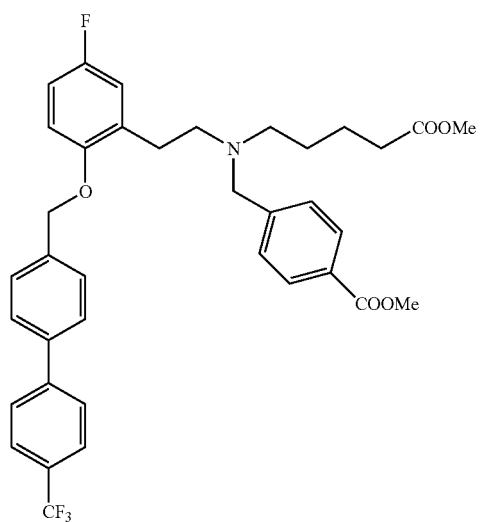

NaOH →

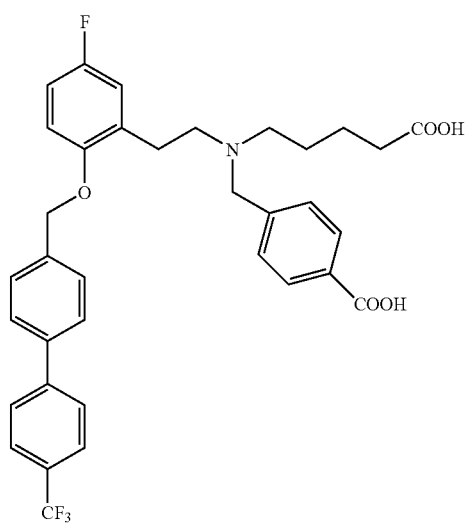

0.45 g (0.69 mmol) of methyl 4-{[(2-{5-fluoro-2-[(4'-methyl-1,1'-biphenyl-4-yl)methoxy]phenyl}ethyl)(5-methoxy-5-oxopentyl)amino]methyl}benzoate from Ex. 185 is dissolved in 8 ml of methanol. 0.5 ml of aqueous sodium hydroxide solution (45%) and 1.5 ml of dichloromethane are added, and the solution is stirred at RT for 8 hours. The reaction is extracted with diethyl ether, the aqueous phase is acidified using sulphuric acid and extracted with ethyl acetate and the extract is filtered through Extrelut and concentrated.

Yield: 245 mg (57.3% of theory)

$^1$H-NMR: (300 MHz, MeOD): 1.60 (m, 4H), 2.20 (t, 2H), 3.00 (m, 4H), 3.20 (m, 2H), 4.20 (s, 2H), 5.10 (s, 2H), 7.00 (m, 3H), 7.50 (m, 4H), 7.70 (m, 6H), 7.90 (d, 2H).

Example 187

Methyl 4-{[(5-ethoxy-5-oxopentyl)(2-{[5-(4-phenylpiperazino)-pentyl]oxy}phenethyl)amino]methyl}benzoate

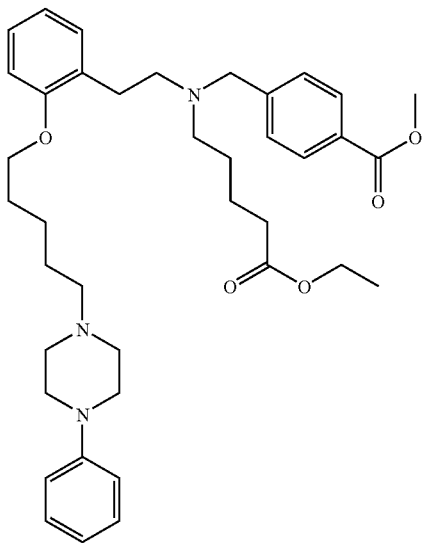

200.0 mg (0.355 mmol) of methyl 4-{[{2-[(5-bromopentyl)oxy]phenethyl}(5-ethoxy-5-oxopentyl)amino]methyl}benzoate from Ex. 107, 69.21 mg of N-phenylpiperazine and 71.95 mg (0.711 mmol) of triethylamine in 2 ml of tetrahydrofuran are heated at reflux for 18 hours. The reaction solution is washed with water, concentrated and chromatographed over silica gel using the mobile phase ethyl acetate/methanol 10/1.

Yield: 66.0 mg (28.83% of theory)

$^1$H-NMR (300 MHz, d$^6$-DMSO): δ=1.12 (t, 3H), 1.44 (m, 8H), 1.65 (m, 2H), 2.35 (m, 4H), 2.45 (m, 4H), 2.55 (m, 2H), 2.72 (m, 2H), 3.10 (m, 4H), 3.65 (s, 2H), 3.85 (s, 3H), 3.88 (t, 2H), 4.05 (m, 2H), 6.70-6.90 (m, 5H), 7.0-7.2 (m, 4H), 7.4 (d, 2H), 7.8 (d, 2H).

The following compounds can be obtained analogously:

| Example | Structure | Physical data: $^1$H-NMR (δ in ppm, selection)[1] or LC/MS (mass/retention time [min])[2] |
|---|---|---|
| 188 (from 107 and N-(4-chlorophenyl)-piperazine) | | 679 (M + 1), Rt = 3.60 |

-continued

| Example | Structure | Physical data: $^1$H-NMR (δ in ppm, selection)$^{1)}$ or LC/MS (mass/retention time [min])$^{2)}$ |
|---|---|---|
| 189 (from 108 and N-phenyl-piperazine) | 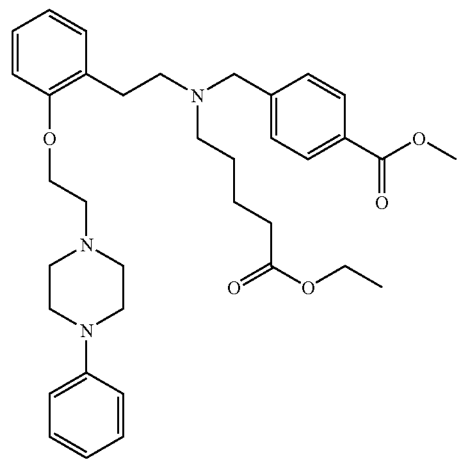 | 602 (M + 1), Rt = 3.60 |
| 190 (from 187 by process E) | 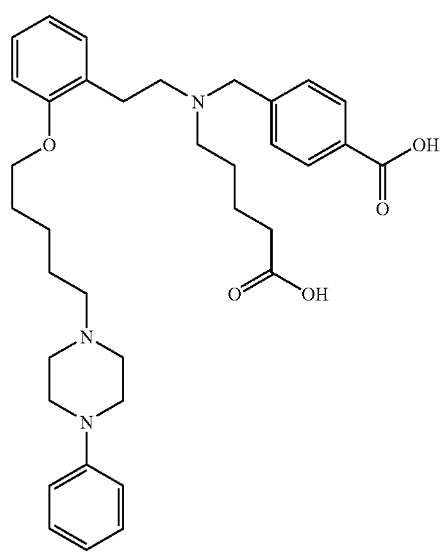 | 601 (M + 1), Rt = 2.43 |

-continued

| Example | Structure | Physical data: <br> $^1$H-NMR ($\delta$ in ppm, selection)[1] or LC/MS (mass/retention time [min])[2] |
|---|---|---|
| 191 (from 188 by process E) | 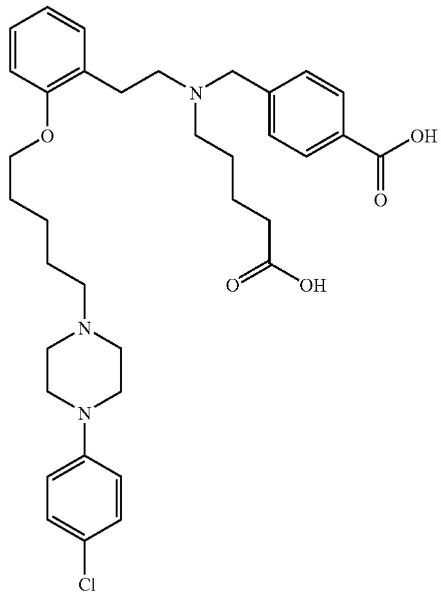 | 635 (M + 1), Rt = 2.58 |
| 192 (from 189 by process E) | 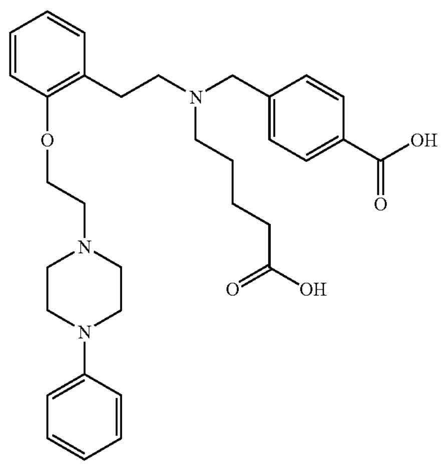 | 559 (M + 1), Rt = 2.11 |
| 193 (from I and 1,3-dibromo-propane by process D) | 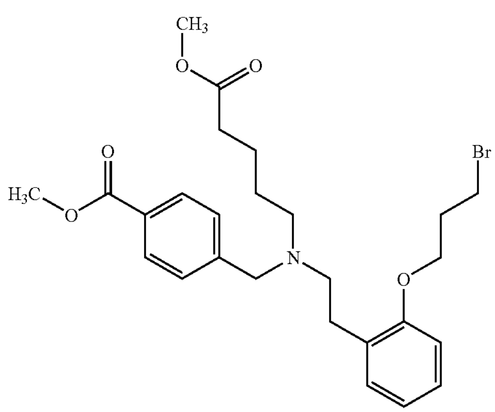 | 1.50 (m, 4H), 2.40 (m, 4H), 2.70 (m, 6H), 3.50 (m, 2H), 3.60 (m, 5H), 3.90 (s, 3H), 4.00 (t, 2H), 6.80-7.40 (m, 6H), 7.90 (d, 2H) |

-continued

| Example | Structure | Physical data:<br>¹H-NMR (δ in ppm, selection)[1] or LC/MS (mass/retention time [min])[2] |
|---|---|---|
| 194<br>(from I and 1,3-dibromobutane by process D) | | 1.50 (m, 4H), 1.90 (m, 4H), 2.20 (t, 2H), 2.50 (t, 2H), 2.70 (m, 4H), 3.40 (m, 2H), 3.60 (m, 5H), 3.90 (m, 5H), 6.80-7.40 (m, 6H), 7.90 (d, 2H) |
| 195<br>(from 193 and N-phenyl-piperazine) | | 1.50 (m, 4H), 1.90 (m, 2H), 2.40 (t, 2H), 2.70 (m, 8H), 3.10 (m, 8H), 3.60 (m, 5H), 3.90 (s, 3H), 4.00 (t, 2H), 6.80-7.40 (m, 11H), 7.90 (d, 2H) |
| 196<br>(from 195 by process E) | | 574 (M + 1) |

-continued

| Example | Structure | Physical data: <br> $^1$H-NMR ($\delta$ in ppm, selection)[1] or LC/MS (mass/retention time [min])[2] |
|---|---|---|
| 197 (from 194 and N-2-pyrimidinepiperazine and by process E) | 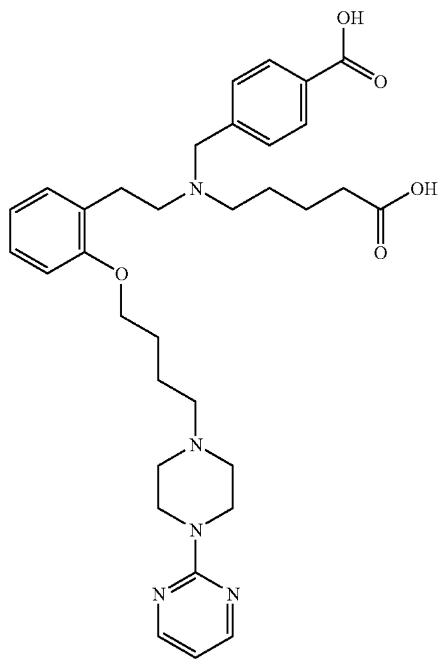 | 1.50-2.80 (m, 20H), 3.60 (s, 2H), 3.80 (m, 6H), 4.00 (t, 2H), 6.50-7.40 (m, 7H), 7.90 (d, 2H), 8.20 (d, 2H) |
| 198 (from 194 and N-phenyl-piperazine) | 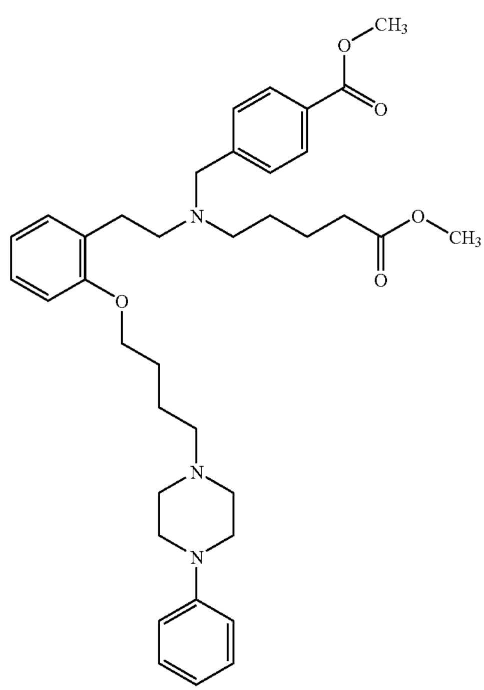 | 1.50 (m, 8H), 2.20 (t, 2H), 2.70 (m, 12H), 3.10 (m), 3.60 (m, 5H), 4.00 (m, 5H), 6.80-7.40 (m, 11H), 7.90 (d, 2H) |

| Example | Structure | Physical data:<br>$^1$H-NMR (δ in ppm, selection)[1] or LC/MS (mass/retention time [min])[2] |
|---|---|---|
| 199<br>(from 198 by process E) | | 1.50 (m, 8H), 2.20 (t, 2H), 2.80-2.50 (m, 12H), 3.20 (m, 4H), 3.80 (s, 2H), 4.00 (t, 2H), 6.80-7.40 (m, 11H), 7.90 (d, 2H) |
| 200<br>(from 193 and N-2-methyl-phenylpipera-zine) | | 1.50-3.20 (m), 3.60 (m, 5H), 4.00 (m, 5H), 6.80-7.40 (m, 10H), 7.90 (d, 2H) |

-continued

| Example | Structure | Physical data: $^1$H-NMR (δ in ppm, selection)$^{1)}$ or LC/MS (mass/retention time [min])$^{2)}$ |
|---|---|---|
| 201 (from 200 by process E) | 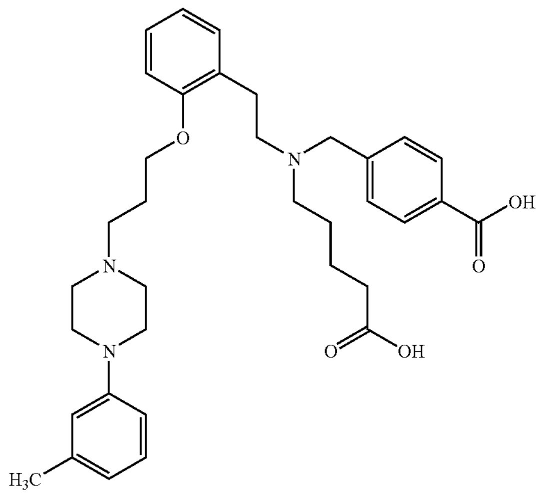 | 1.50 (m, 6H), 2.20 (m, 5H), 2.80-2.50 (m), 3.20 (m), 3.60 (s, 2H), 4.00 (t, 2H), 6.80-7.40 (m, 10H), 7.90 (d, 2H) |
| 202 (from 194 and piperidine) | 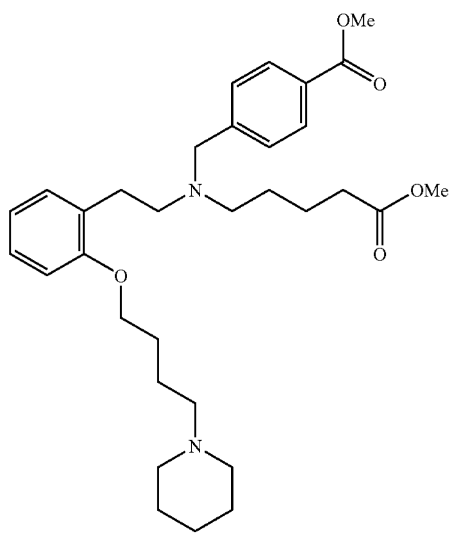 | 1.50 (m, 14H), 2.80-2.10 (m, 14H), 3.60 (m, 5H), 3.90 (m, 5H), 6.80-7.40 (m, 6H), 7.90 (d, 2H) |
| 203 (from 202 by process E) | 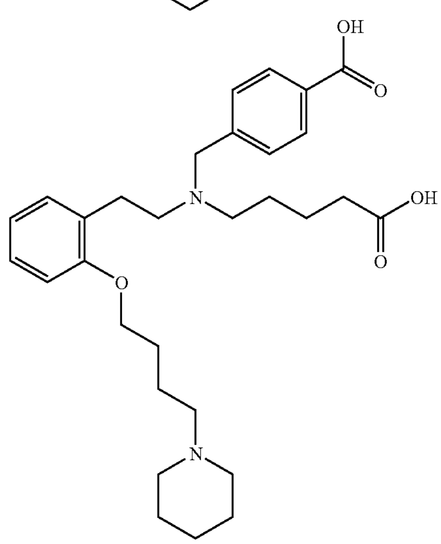 | 1.50 (m, 14H), 2.80-2.10 (m, 14H), 3.60 (s, 2H), 3.90 (t, 2H), 6.80-7.40 (m, 6H), 7.90 (d, 2H) |

-continued

| Example | Structure | Physical data: $^1$H-NMR ($\delta$ in ppm, selection)[1] or LC/MS (mass/retention time [min])[2] |
|---|---|---|
| 204 (from IX and 1,3-dibromo-propane by process D) | 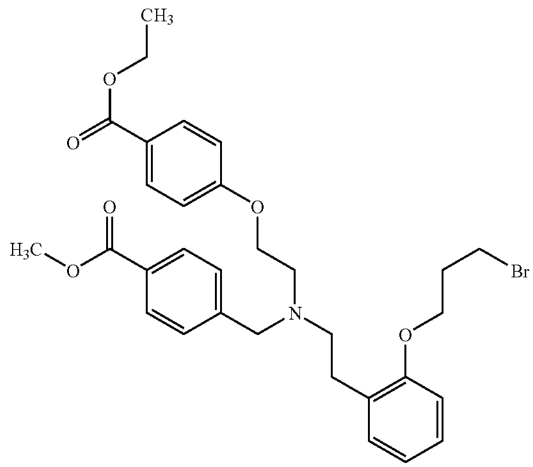 | 1.30 (t, 3H), 2.20 (m, 2H), 2.80 (m, 4H), 3.00 (t, 2H), 3.50 (t, 2H), 3.80 (s, 2H), 3.90 (s, 3H), 4.00 (m, 4H), 4.30 (q, 2H), 6.80-7.40 (m, 8H), 8.00 (m, 4H). |
| 205 (from 204 and N-2-methyl-phenylpiperazine and by process E) | | 652 (M + 1), Rt = 2.53[3] |
| 206 (from 204 and N-phenyl-piperazine and by process E) | 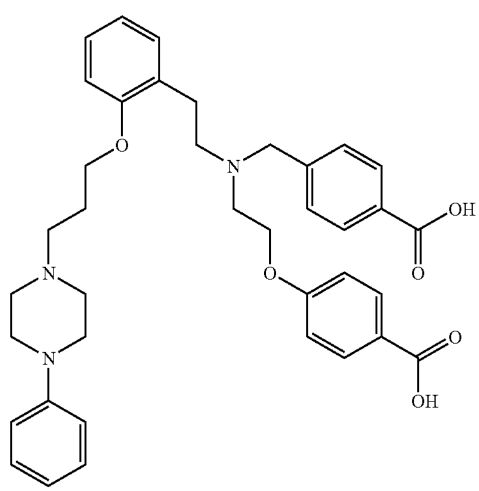 | 638 (M + 1), Rt = 2.39[3] |

-continued

| Example | Structure | Physical data: $^1$H-NMR (δ in ppm, selection)[1] or LC/MS (mass/retention time [min])[2] |
|---|---|---|
| 207 (from 204 and N-4-trifluoro-methylphenyl-piperazine) | 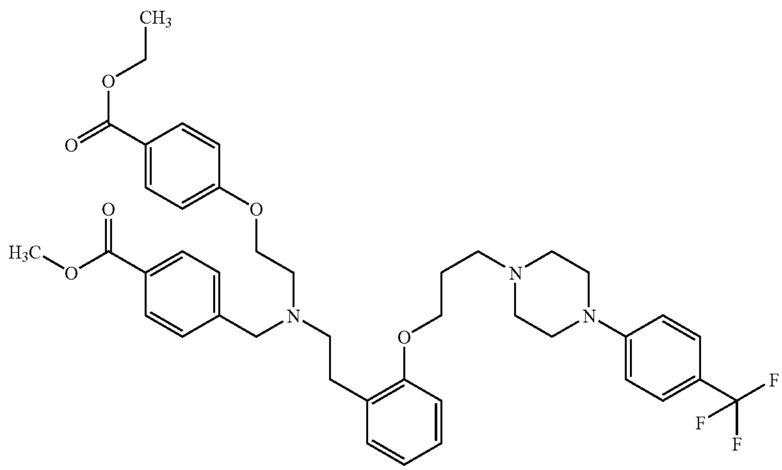 | 1.30 (t, 3H), 1.90 (m, 2H), 2.50 (m, 6H), 2.90 (m, 6H), 3.20 (m, 4H), 4.00 (m, 9H), 4.30 (q, 2H), 6.80-7.40 (m, 12H), 8.00 (m, 4H). |
| 208 (from 207 by process E) | 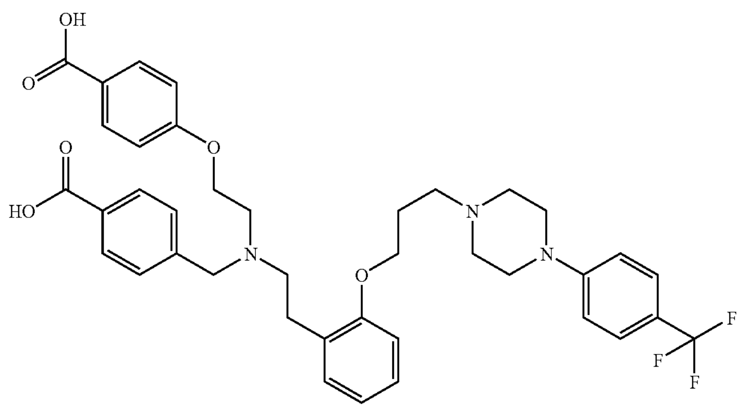 | 706 (M + 1), Rt = 2.64[3] |
| 209 (from 204 and N-2,4-di-fluorophenyl-piperazine) | 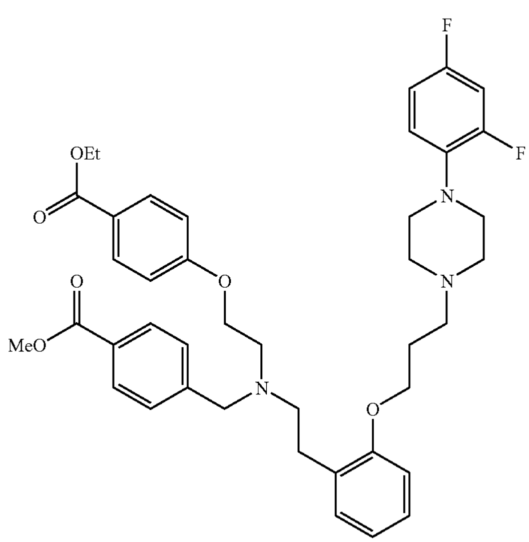 | 1.30 (t, 3H), 1.90 (m, 2H), 2.50 (m, 6H), 2.80 (s, 4H), 3.00 (m, 6H), 4.00 (m, 9H), 4.30 (q, 2H), 6.80-7.40 (m, 11H), 8.00 (m, 4H). |

| Example | Structure | Physical data: $^1$H-NMR (δ in ppm, selection)[1] or LC/MS (mass/retention time [min])[2] |
|---|---|---|
| 210 (from 209 by process E) | 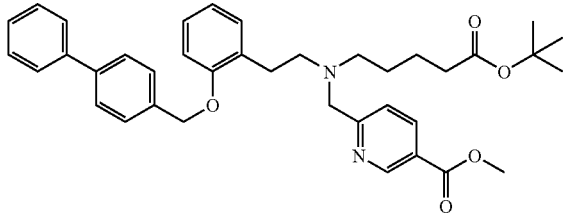 | 674 (M + 1); Rt = 2.60[2] |

[1] NMR conditions: d6-DMSO, 300 MHz
[2] LC/MS conditions: column: Symmetry C18 2.1 * 150 mm; mobile phase: acetonitrile/0.6 g of HCl 30% strength/H$_2$O; gradient: 10% acetonitrile to 90% acetonitrile; flow rate: 0.6 ml/min; detector: UV 210 nm
[3] LC/MS conditions: column: Symmetry C18 2.1 * 50 mm; mobile phase: acetonitrile/H$_2$O (0.1% formic acid); gradient: 10% acetonitrile to 90% acetonitrile; flow rate: 0.5 ml/min; detector: UV 210 nm 211: Methyl 6-{[{2-[2-(1,1'-biphenyl-4-ylmethoxy)phenyl]ethyl}(5-tert-butoxy-5-oxopentyl)-amino]methyl}nicotinate A solution of 132.0 mg (0.29 mmol) of XXa in 3 ml of DMF was admixed with 198.5 mg (1.44 mmol) of potassium carbonate, 121.1 mg (0.32 mmol) of methyl-6-(bromomethyl)nicotinate and a catalytic amount of KI. The mixture was stirred at room temperature for 16 h and the reaction was monitored by thin-layer chromatography. The solution was admixed with water and extracted with ethyl acetate/cyclohexane 1:1. The combined organic phases were dried over Na$_2$SO$_4$ and the solvent was removed. The product was purified chromatographically (silica gel, cyclohexane/ethyl acetate 10:1).

Yield: 55.8%

$^1$H-NMR (300 MHz, CDCl$_3$): δ=1.16-1.58 (m, 4H), 1.40 (s, 9H), 2.11 (t, J=7.2 Hz, 2H), 2.54 (t, J=6.4 Hz, 2H), 2.70-2.81 (m, 2H), 2.82-2.92 (m, 2H), 3.81 (s, 2H), 3.89 (s, 3H), 5.04 (s, 2H), 6.82-7.62 (m, 14H), 8.04-8.17 (m, 1H), 9.02-9.08 (m, 1H).

The following compounds were prepared analogously:

| Example | Structure | Yield (%) | Physical data: $^1$H-NMR (δ in ppm, selection)[1] or LC/MS (mass/retention time [min])[2] |
|---|---|---|---|
| 212 (from XXa and 2-methoxy-carbonyl-benzyl chloride) | 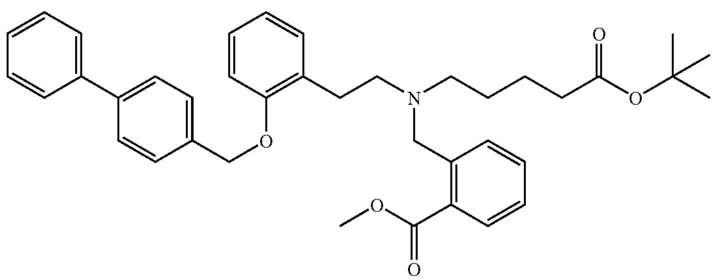 | 66.4 | $^1$H NMR (300 MHz, CDCl$_3$): δ = 1.39 (s, 9H), 1.45-1.52 (m, 4H), 2.07 (t, J = 7.4 Hz, 2H), 2.47 (t, J = 6.6.Hz, 2H), 2.65-2.75 (m, 2H), 2.77-2.87 (m, 2H), 3.81 (s, 3H), 3.90 (s, 2H), 5.05 (s, 2H), 6.78-7.80 (m, 17H). |

-continued

| Example | Structure | Yield (%) | Physical data: ¹H-NMR (δ in ppm, selection)¹⁾ or LC/MS (mass/retention time [min])²⁾ |
|---|---|---|---|
| 213 (from XXa and 3-t-butoxy-carbonyl-benzyl chloride) | | 85.5 | ¹H NMR (300 MHz, CDCl₃): δ = 1.35-1.64 (m, 4H), 1.40 (s, 9H), 1.57 (s, 9H), 2.10 (t, J = 7.2 Hz, 2H), 2.47 (t, J = 6.4 Hz, 2H), 2.66-2.76 (m, 2H), 2.79-2.91 (m, 2H), 3.63 (s, 2H), 5.05 (s, 2H), 6.80-7.92 (m, 17H). |
| 214 (from XXa and 2-methoxy-4-methoxy-carbonyl-benzyl chloride) | | 42.8 | ¹H NMR (300 MHz, CDCl₃): δ 1.31-1.57 (m, 4H), 1.40 (s, 9H), 2.11 (t, J= 7.0 Hz, 2H), 2.51 (t, J = 7.0 Hz, 2H), 2.68-2.78 (m, 2H), 2.81-2.92 (m, 2H), 3.66 (s, 2H), 3.80 (s, 3H), 3.87 (s, 3H), 5.05 (s, 2H), 6.81-7.64 (m, 16H). |
| 215 (from XXa and 3-methoxy-4-methoxycarbonyl-benzyl chloride) | | 55.6 | ¹H NMR (300 MHz, CDCl₃): δ = 1.34-1.61 (m, 4H), 1.40 (s, 9H), 2.03-2.16 (m, 2H), 2.35-2.55 (m, 2H), 2.64-2.76 (m, 2H), 2.77-2.93 (m, 2H), 3.59 (s, 2H), 3.79 (s, 3H), 3.84 (s, 3H), 5.04 (s, 2H), 6.73-7.73 (m, 16H). |
| 216 (from XXa and 4-methoxy-carbonyl-methyl-benzyl chloride) | | 57.7 | ¹H NMR (300 MHz, CDCl₃): δ = 1.34-1.59 (m, 4H), 1.40 (s, 9H), 2.11 (t, J = 7.0 Hz, 2H), 2.46 (t, J = 7.0 Hz, 2H), 2.62-2.74 (m, 2H), 2.78-2.90 (m, 2H), 3.56 (s, 2H), 3.58 (s, 2H), 3.65 (s, 3H), 5.05 (s, 2H), 6.80-7.64 (m, 17H). |

| Example | Structure | Yield (%) | Physical data: $^1$H-NMR (δ in ppm, selection)[1] or LC/MS (mass/retention time [min])[2] |
|---|---|---|---|
| 217 (from XXb and 4-methoxy-carbonyl-benzyl chloride) | 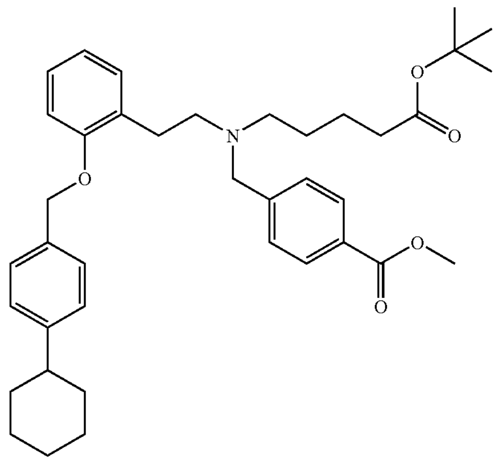 | 50.1 | LC/MS: 4.52 min, m/z = 614 (M + 1). |

218: 5-{{2-[2-(1,1'-Biphenyl-4-ylmethoxy)phenyl]ethyl}[2-methoxy-4-(methoxy-carbonyl)-benzyl]-amino}pentanoic Acid Hydrochloride

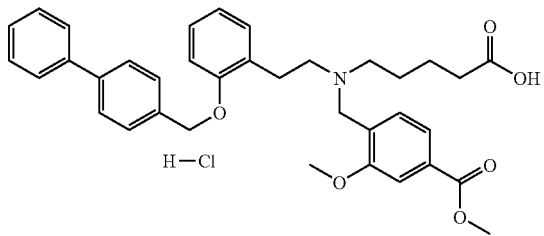

A solution of 96.7 mg (0.15 mmol) of the compound from Ex. 214 in 3 ml of dioxane was mixed with 5 ml of 1 M HCl in dioxane. The mixture was stirred at room temperature and the reaction was monitored by thin-layer chromatography. After the reaction had ended, the solvent was removed and the product was purified chromatographically (silica gel, CH$_2$Cl$_2$/MeOH 10:1).

Yield: 51.8 mg (55.2%)

$^1$H NMR (400 MHz, DMSO-d$_6$): δ=1.37-1.49 (m, 2H), 1.59-1.80 (m, 2H), 2.03-2.26 (m, 2H), 2.95-3.37 (m, 6H), 3.83 (s, 3H), 3.87 (s, 3H), 4.34 (s, 2H), 5.15 (s, 2H), 6.82-7.77 (m, 16H), 9.45 (bs, 1H), 12.08 (bs, 1H).

The following compounds were prepared in an analogous manner, where further hydrolysis of the monoester was achieved in the following manner:

A mixture of 0.078 mmol of monoester, 1 ml of water, 200 µl of 45% strength NaOH and 2 ml of dioxane was stirred at room temperature for 16 h. The mixture was acidified with 1 N HCl and the solvent was removed. The residue was taken up in ethanol and the sodium chloride formed was filtered off. The product was purified chromatographically (preparative thin-layer chromatography, EtOH).

| Example | Structure | Yield (%) | Physical data: $^1$H-NMR (δ in ppm, selection)[1] or LC/MS (mass/retention time [min])[2] |
|---|---|---|---|
| 219 (from XXa and ethyl 5-bromo-pentanoate analogously to 211 and 218) | | 69.4 | $^1$H NMR (300 MHz, DMSO-d$_6$): δ = 1.38-1.77 (m, 8H), 2.21-2.35 (m, 4H), 3.02-3.26 (m, 6H), 3.27-3.60 (m, 2H), 5.02 (s, 2H), 6.64-7.69 (m, 13H), 9,14 (bs, 1H), 12.10 (bs, 2H). |

-continued

| Example | Structure | Yield (%) | Physical data: $^1$H-NMR (δ in ppm, selection)$^{1)}$ or LC/MS (mass/retention time [min])$^{2)}$ |
|---|---|---|---|
| 220 (from 212) | 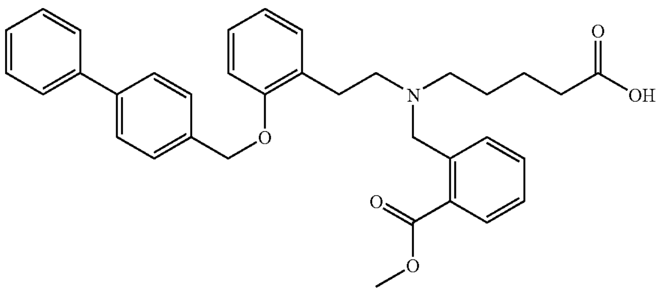 | 77.3 | LC/MS: 3.61 min [m/z = 552 (M + H)] |
| 221 (from 213) | 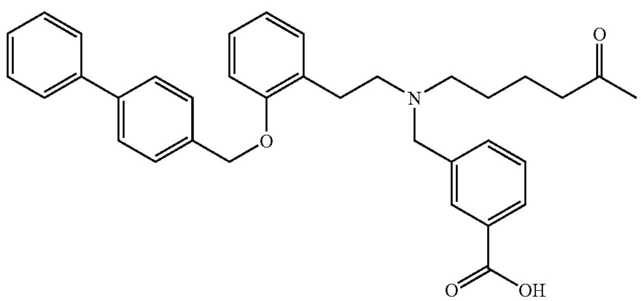 | 39.8 | $^1$H NMR (400 MHz, DMSO-d$_6$): δ = 1.42 (t, J = 7.3 Hz, 2H), 1.58-1.86 (m, 2H), 2.15 (t, J = 7.3 Hz, 2H), 2.86-3.25 (m, 7H), 4.45 (s, 2H), 5.14 (s, 2H), 6.67-8.33 (m, 17H), 12.18 (bs, 1H), 13.12 (bs, 1H). |
| 222 (from 211) | 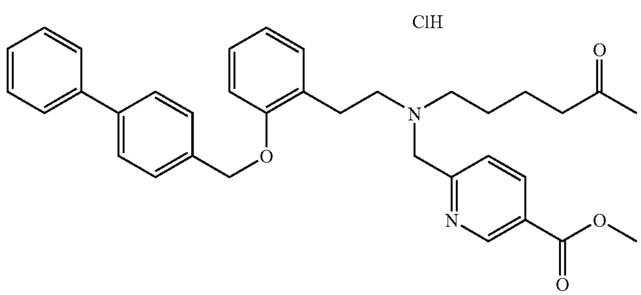 | 44.6 | $^1$H NMR (400 MHz, DMSO-d$_6$): δ = 1.38-1.49 (m, 2H), 1.62-1.75 (m, 2H), 2.17 (t, J = 7.3 Hz, 2H), 3.01-3.11 (m, 2H), 3.12-3.21 (m, 2H), 3.22-3.46 (m, 3H), 3.84 (s, 3H), 4.62 (s, 2H), 5.14 (s, 2H), 6.82-8.39 (m, 16H), 9.08 (bs, 1H). |
| 223 (from 215) | 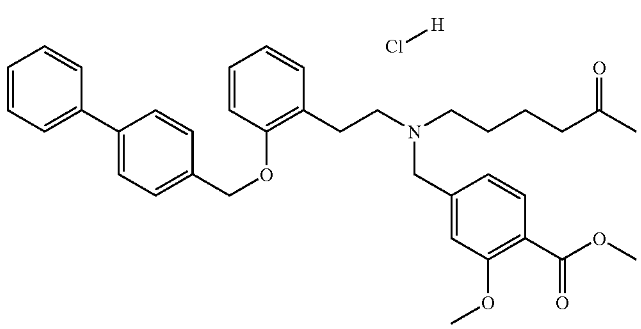 | 32.8 | $^1$H NMR (400 MHz, DMDO-d$_6$): δ = 1.28-1.53 (m, 2H), 1.60-1.83 (m, 2H), 2.08-2.25 (m, 2H), 2.93-3.39 (m, 6H), 3.75 (s, 3H), 3.87 (s, 3H), 4.39 (s, 2H), 5.15 (s, 2H), 6.77-7.80 (m, 16H), 10.26 (bs, 1H), 12.11 (bs, 1H). |

-continued

| Example | Structure | Yield (%) | Physical data: ¹H-NMR (δ in ppm, selection)¹⁾ or LC/MS (mass/retention time [min])²⁾ |
|---|---|---|---|
| 224 (from 216) | 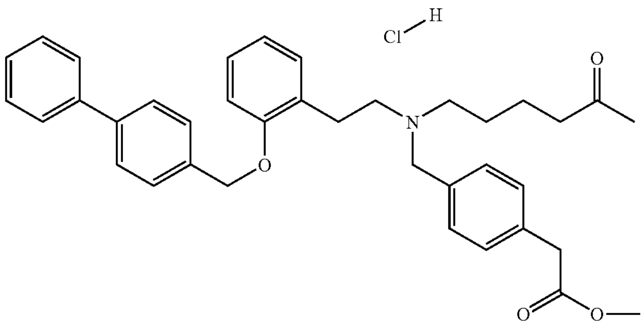 | 48.8 | ¹H NMR (400 MHz, DMSO-d₆): δ = 1.34-1.51 (m, 2H), 1.58-1.80 (m, 2H), 2.16 (t, J = 7.4 Hz, 2H), 2.91-3.23 (m, 6H), 3.58 (s, 3H), 3.68 (s, 2H), 4.33 (s, 2H), 5.15 (s, 2H), 6.82-7.77 (m, 17H), 10.12 (bs, 1H), 12.11 (bs, 1H). |
| 225 (from XXa and 4-methoxy-carbonyl-benzyl chloride analogously to 211 and 218) | | 70.0 | ¹H NMR (400 MHz, DMSO-d₆): δ = 1.36-1.52 (m, 2H), 1.59-1.79 (m, 2H), 2.04-2.24 (m, 2H), 2.89-3.26 (m, 6H), 3.81 (s, 3H), 4.43 (s, 2H), 5.14 (s, 2H), 6.76-8.13 (m, 17H), 10.24 (bs, 1H), 12.09 (bs, 1H). |
| 226 (from 216) | 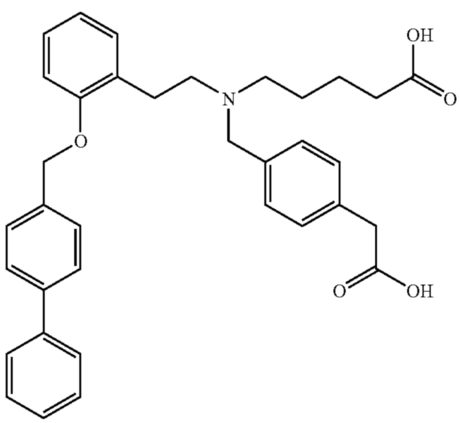 | 100 | LC/MS = 4.09 min, m/z = 552 (M + H). |
| 227 (from 212) | 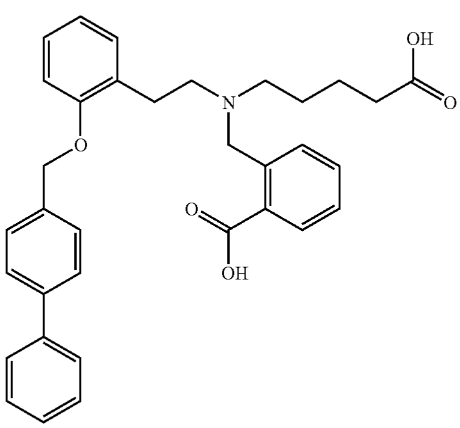 | 76.9 | LC/MS = 3.60 min, m/z = 538 (M + H). |

US 7,781,470 B2

217                                                                                           218

-continued

| Example | Structure | Yield (%) | Physical data:<br>¹H-NMR (δ in ppm, selection)[1] or LC/MS (mass/retention time [min])[2] |
|---|---|---|---|
| 228 (from 211) | 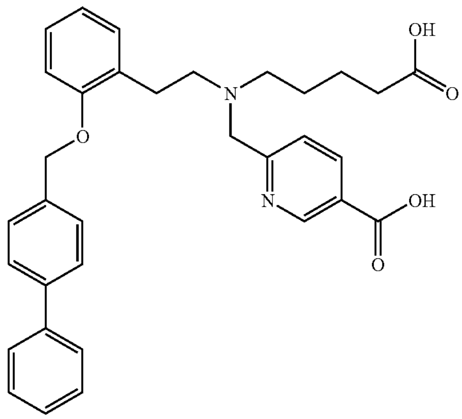 | 78.9 | LC/MS = 3.29 min, m/z = 539 (M + H). |
| 229 (from 214) | 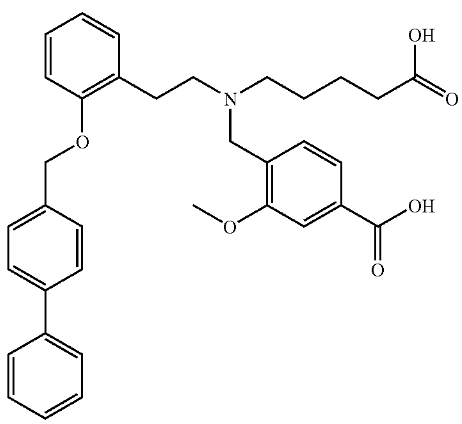 | 76.2 | LC/MS = 3.42 min, m/z = 568 (M + H). |
| 230 (from 215) | 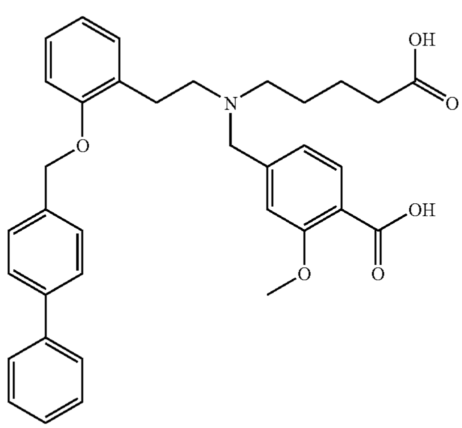 | 79.2 | LC/MS = 3.32 min, m/z = 568 (M + H). |

| Example | Structure | Yield (%) | Physical data: $^1$H-NMR (δ in ppm, selection)[1]) or LC/MS (mass/retention time [min])[2]) |
|---|---|---|---|
| 231 (from 217) | 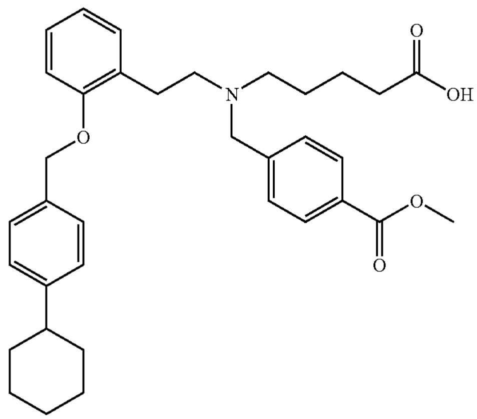 | 76.2 | LC/MS: 3.99 min, m/z = 558 (M + H). |

232: 4-[((4-carboxybutyl){2-[2-({4-[2-(4-hydroxyphenyl)ethyl]benzyl}oxy)phenyl]-ethyl}amino)methyl]benzoic Acid 27 mg (0.037 mmol) of methyl 4-{[{2-[2-({4-[2-(4-{[tert-butyl(dimethyl)-silyl]oxy}phenyl)ethyl]benzyl}oxy)phenyl]ethyl}(5-ethoxy-5-oxopentyl)amino]-methyl}benzoate from XXI are dissolved in 10 ml of THF. 0.03 ml of tetrabutylammonium fluoride (1M solution in THF) are added, and the solution is stirred at RT for 1 hour. The solvents are evaporated under reduced pressure. The residue is dissolved in 2 ml of methanol. 0.05 ml of aqueous sodium hydroxide solution, 45%, and 0.2 ml of dichloromethane are added, and the solution is stirred at RT for 8 hours. The mixture is concentrated, water is added and the solution is acidified using sulphuric acid. The solid is filtered off and dried.

Yield: 20 mg (93% of theory)

$^1$H-NMR (300 MHz, MeOD): δ 1.45 (m, 4H), 2.30 (t, 2H), 2.80 (m, 4H), 3.00-3.40 (m), 4.80 (s, 2H), 5.00 (s, 2H), 6.60 (m, 2H), 6.90-7.30 (10H), 7.50 (d, 2H), 8.00 (d, 2H).

We claim:

1. A compound of the formula (VI)

(VI)

in which
V is O or $S(O)_o$, in which o is 0, 1, or 2;
Q is methylene;
Y is phenyl;
$R^3$ is hydrogen, halogen, straight-chain or branched alkyl, straight-chain or branched halogenoalkyl, straight-chain or branched alkoxy, or alkoxycarbonyl having in each case up to 4 carbon atoms, CN, $NO^2$ or $NR^{19}R^{20}$ in which $R^{19}$ and $R^{20}$ independently of one another are hydrogen, straight-chain or branched alkyl having up to 4 carbon atoms or cycloalkyl having 3 to 8 carbon atoms;
m is an integer from 1 to 4;
W is straight-chain or branched alkylene having up to 6 carbon atoms or straight-chain or branched alkenediyl having up to 6 carbon atoms which may in each case contain a group from the group consisting of O, $S(O)_q$, $NR^{21}$, CO and $CONR^{21}$, or is CO, NHCO or OCO, in which q is 0, 1 or 2, $R^{21}$ is hydrogen, straight-chain or branched alkyl having up to 8 carbon atoms or cycloalkyl having 3 to 8 atoms;
X is straight-chain or branched alkylene having up to 12 carbon atoms or straight-chain or branched alkenediyl having up to 12 carbon atoms which may in each case contain one to three groups from the group consisting of O, $S(O)_r$, $NR^{28}$, CO or $CONR^{29}$, aryl or aryloxy having 6 to 10 carbon atoms, where the aryl radical for its part may be mono- or polysubstituted by halogen, CN, NO2, alkyl, alkoxy, halogenoalkyl or halogenoalkoxy having up to 6 carbon atoms, where optionally any two atoms of the abovementioned chains are attached to one another via an alkyl chain, forming a three- to eight-membered ring, in which r is 0, 1 or 2, $R^{28}$ is hydrogen, alkyl having 1 to 8 carbon atoms or cycloakyl having 3 to 8 carbon atoms, $R^{29}$ is hydrogen, straight-chain or branched alkyl having up to 8 carbon atoms or cycloalkyl having 3 to 8 carbon atoms; and $R^1$ is tetrazolyl, $COOR^{30}$ or $CONR^{31}R^{32}$, in which $R^{30}$ is hydrogen, alkyl having 1 to 8 carbon atoms or cycloalkyl having 3 to 8 carbon atoms, $R^{31}$ and $R^{32}$ independently of one another are each hydrogen, straight-chain or branched alkyl having up to 8 carbon atoms, cycloalkyl having 3 to 8 carbon atoms or a radical of the formula $SO_2R^{33}$, in which $R^{33}$ is straight-chain or branched alkyl having up to 4 carbon atoms or aryl having 6 to 10 carbon atoms, where the aryl radical for its part may be mono- or polysubstituted by halogen, CN, NO2, alkyl, alkoxy, halogenoalkyl or halogenoalkoxy having up to 6 carbon atoms, or a stereoisomer or salt thereof.

\* \* \* \* \*